US012682579B2

(12) United States Patent
Kimball et al.

(10) Patent No.: US 12,682,579 B2
(45) Date of Patent: Jul. 14, 2026

(54) ADAPTATION AND ADJUSTABILITY OR OVERLAID INSTRUMENT INFORMATION FOR SURGICAL SYSTEMS

(71) Applicant: Cilag GmbH International, Zug (CH)

(72) Inventors: Cory G. Kimball, Hamilton, OH (US); Monica L. Z. Rivard, Cincinnati, OH (US); Leonardo N. Rossoni, Rahway, NJ (US); Matthew D. Cowperthwait, Cincinnati, OH (US); Felix J. Bork, Schnürpflingen (DE); Shane R. Adams, Lebanon, OH (US); Taylor W. Aronhalt, Loveland, OH (US); Kevin M. Fiebig, Cincinnati, OH (US); Frederick E. Shelton, IV, Hillsboro, OH (US); Bernhard A. Fuerst, Sunnyvale, CA (US); Risto Kojcev, Santa Clara, CA (US); Brendan J. Oberkircher, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 738 days.

(21) Appl. No.: 17/688,667

(22) Filed: Mar. 7, 2022

(65) Prior Publication Data

US 2022/0331054 A1      Oct. 20, 2022

Related U.S. Application Data

(60) Provisional application No. 63/284,326, filed on Nov. 30, 2021, provisional application No. 63/174,674, filed on Apr. 14, 2021.

(51) Int. Cl.
*G06T 11/00* (2006.01)
*A61B 34/00* (2016.01)
(Continued)

(52) U.S. Cl.
CPC .............. *G06T 11/00* (2013.01); *A61B 34/20* (2016.02); *A61B 34/25* (2016.02); *A61B 34/30* (2016.02);
(Continued)

(58) Field of Classification Search
CPC .............. A61B 2090/365; A61B 34/20; A61B 2090/502; A61B 34/25; A61B 2034/2055;
(Continued)

(56) References Cited

U.S. PATENT DOCUMENTS 4,171,700 A     10/1979  Farin
4,849,752 A      7/1989  Bryant
(Continued)

FOREIGN PATENT DOCUMENTS

CA          3003058 A1     5/2017
CN        112603496 A      4/2021
(Continued)

OTHER PUBLICATIONS

"ATM-MPLS Network Interworking Version 2.0, af-aic-0178.001" ATM Standard, The ATM Forum Technical Committee, published Aug. 2003.
(Continued)

*Primary Examiner* — Alex Kok S Liew
(74) *Attorney, Agent, or Firm* — Condo Roccia Koptiw LLP

(57) ABSTRACT

An augmented reality display system used during a surgical procedure is disclosed. The system includes an imaging device to capture a real image of a surgical area during the surgical procedure. An augmented reality display presents functional overlay data associated with critical operations of a surgical instrument being actively visualized and interactions of the surgical instrument with tissue in the surgical area. The functional data is overlaid onto the real image of
(Continued)

the surgical area. The functional data overlay is a combination of aspects of the critical operations of the surgical instrument and the interaction of the surgical instrument with the tissue in the surgical area. A processor receives functional data from the surgical instrument, determines the overlaid data related to the functional aspect of the surgical instrument, and combines the aspect of the tissue in the surgical area with the functional data received from the surgical instrument.

19 Claims, 64 Drawing Sheets

(51) Int. Cl.

| | |
|---|---|
| *A61B 34/20* | (2016.01) |
| *A61B 34/30* | (2016.01) |
| *A61B 34/32* | (2016.01) |
| *A61B 90/00* | (2016.01) |
| *G06F 3/14* | (2006.01) |
| *G06F 3/147* | (2006.01) |
| *G06T 7/00* | (2017.01) |
| *G06T 7/20* | (2017.01) |
| *G06T 19/00* | (2011.01) |
| *G06V 20/20* | (2022.01) |
| *G08B 21/18* | (2006.01) |
| *G16H 20/40* | (2018.01) |
| *G16H 40/67* | (2018.01) |
| *H04L 9/40* | (2022.01) |
| *H04L 67/12* | (2022.01) |
| *H04W 24/10* | (2009.01) |
| *H04W 76/14* | (2018.01) |
| *A61B 34/10* | (2016.01) |

(52) U.S. Cl.
CPC .............. *A61B 34/32* (2016.02); *A61B 34/76* (2016.02); *A61B 90/36* (2016.02); *A61B 90/361* (2016.02); *A61B 90/37* (2016.02); *A61B 90/39* (2016.02); *G06F 3/14* (2013.01); *G06F 3/1454* (2013.01); *G06F 3/147* (2013.01); *G06T 7/0012* (2013.01); *G06T 7/20* (2013.01); *G06T 19/006* (2013.01); *G06V 20/20* (2022.01); *G08B 21/182* (2013.01); *G16H 20/40* (2018.01); *G16H 40/67* (2018.01); *H04L 63/105* (2013.01); *H04L 67/12* (2013.01); *H04W 24/10* (2013.01); *H04W 76/14* (2018.02); *A61B 2034/102* (2016.02); *A61B 2034/2055* (2016.02); *A61B 2034/2072* (2016.02); *A61B 2034/252* (2016.02); *A61B 2034/254* (2016.02); *A61B 2090/365* (2016.02); *A61B 2090/368* (2016.02); *A61B 2090/371* (2016.02); *A61B 2090/372* (2016.02); *A61B 2090/373* (2016.02); *A61B 2090/3937* (2016.02); *A61B 2090/3975* (2016.02); *G06T 2207/10028* (2013.01); *G06T 2207/30024* (2013.01); *G06T 2210/41* (2013.01)

(58) Field of Classification Search
CPC . A61B 34/30; A61B 90/37; A61B 2034/2065; A61B 2034/2048; A61B 2090/372; A61B 90/36; A61B 2017/00207; A61B 2017/00203; A61B 2034/254; A61B 34/32; A61B 2090/371; A61B 90/361; A61B 90/39; A61B 2034/105; A61B 2090/064; A61B 2090/3937; G06T 19/006; G06T 2210/41; G06T 7/20; G06T 7/70; G06T 7/0012; G06T 2200/24; G06T 11/60; G06T 11/00; G06T 2207/30204; G06T 2207/10028; G06T 2207/30024; G06T 7/73; G06T 2207/10024; G06T 2207/10048; G06T 7/246; G06T 19/003; G06T 2207/30244; G06T 17/00; G06T 17/20; G06T 2207/30004; G06T 19/00; G06T 19/20; G06T 2207/10012; G06F 3/011; G06F 3/14; G06F 3/1454; G06F 3/147; G06F 3/017; G06F 3/016; G06F 3/03545

See application file for complete search history.

(56) References Cited

U.S. PATENT DOCUMENTS

| | | | |
|---|---|---|---|
| D303,787 | S | 10/1989 | Messenger et al. |
| D327,061 | S | 6/1992 | Soren et al. |
| 5,189,277 | A | 2/1993 | Boisvert et al. |
| 5,204,669 | A | 4/1993 | Dorfe et al. |
| 5,318,563 | A | 6/1994 | Malis et al. |
| 5,325,270 | A | 6/1994 | Wenger et al. |
| 5,425,375 | A | 6/1995 | Chin et al. |
| D379,346 | S | 5/1997 | Mieki |
| 5,690,504 | A | 11/1997 | Scanlan et al. |
| 5,693,042 | A | 12/1997 | Boiarski et al. |
| 5,724,468 | A | 3/1998 | Leone et al. |
| 6,049,467 | A | 4/2000 | Tamarkin et al. |
| 6,055,458 | A | 4/2000 | Cochran et al. |
| D431,811 | S | 10/2000 | Nishio et al. |
| 6,179,136 | B1 | 1/2001 | Kluge et al. |
| 6,269,411 | B1 | 7/2001 | Reasoner |
| 6,288,606 | B1 | 9/2001 | Ekman et al. |
| 6,416,471 | B1 | 7/2002 | Kumar et al. |
| 6,501,485 | B1 | 12/2002 | Dash et al. |
| 6,546,270 | B1 | 4/2003 | Goldin et al. |
| 6,584,358 | B2 | 6/2003 | Carter et al. |
| 6,611,793 | B1 | 8/2003 | Burnside et al. |
| 6,731,514 | B2 | 5/2004 | Evans |
| 6,760,218 | B2 | 7/2004 | Fan |
| 6,839,238 | B2 | 1/2005 | Derr et al. |
| 6,843,657 | B2 | 1/2005 | Driscoll et al. |
| 6,913,471 | B2 | 7/2005 | Smith |
| 7,009,511 | B2 | 3/2006 | Mazar et al. |
| 7,044,949 | B2 | 5/2006 | Orszulak et al. |
| 7,074,205 | B1 | 7/2006 | Duffy et al. |
| 7,134,994 | B2 | 11/2006 | Alpert et al. |
| 7,171,784 | B2 | 2/2007 | Eenigenburg |
| 7,217,269 | B2 | 5/2007 | El-Galley et al. |
| 7,252,664 | B2 | 8/2007 | Nasab et al. |
| 7,331,699 | B2 | 2/2008 | Gawalkiewicz et al. |
| 7,344,532 | B2 | 3/2008 | Goble et al. |
| 7,353,068 | B2 | 4/2008 | Tanaka et al. |
| 7,408,439 | B2 | 8/2008 | Wang et al. |
| D579,876 | S | 11/2008 | Novotney et al. |
| D583,328 | S | 12/2008 | Chiang |
| 7,496,418 | B2 | 2/2009 | Kim et al. |
| D589,447 | S | 3/2009 | Sasada et al. |
| 7,500,747 | B2 | 3/2009 | Howell et al. |
| 7,518,502 | B2 | 4/2009 | Austin et al. |
| 7,563,259 | B2 | 7/2009 | Takahashi |
| 7,601,149 | B2 | 10/2009 | DiCarlo et al. |
| 7,637,907 | B2 | 12/2009 | Blaha |
| 7,656,671 | B2 | 2/2010 | Liu et al. |
| 7,757,028 | B2 | 7/2010 | Druke et al. |
| D631,252 | S | 1/2011 | Leslie |
| 7,932,826 | B2 | 4/2011 | Fritchie et al. |
| 7,945,065 | B2 | 5/2011 | Menzl et al. |
| 7,945,342 | B2 | 5/2011 | Tsai et al. |
| 7,982,776 | B2 | 7/2011 | Dunki-Jacobs et al. |
| 7,995,045 | B2 | 8/2011 | Dunki-Jacobs |
| 8,019,094 | B2 | 9/2011 | Hsieh et al. |
| 8,086,008 | B2 | 12/2011 | Coste-maniere et al. |
| D655,678 | S | 3/2012 | Kobayashi et al. |
| D657,368 | S | 4/2012 | Magee et al. |

(56)                    References Cited

U.S. PATENT DOCUMENTS

| | | | |
|---|---|---|---|
| 8,239,066 B2 | 8/2012 | Jennings et al. |
| D667,838 S | 9/2012 | Magee et al. |
| D675,164 S | 1/2013 | Kobayashi et al. |
| D676,392 S | 2/2013 | Gassauer |
| D678,196 S | 3/2013 | Miyauchi et al. |
| D678,304 S | 3/2013 | Yakoub et al. |
| 8,423,182 B2 | 4/2013 | Robinson et al. |
| D687,146 S | 7/2013 | Juzkiw et al. |
| 8,504,136 B1 | 8/2013 | Sun et al. |
| 8,540,709 B2 | 9/2013 | Allen |
| 8,567,393 B2 | 10/2013 | Hickle et al. |
| D704,839 S | 5/2014 | Juzkiw et al. |
| 8,795,001 B1 | 8/2014 | Lam et al. |
| 8,819,581 B2 | 8/2014 | Nakamura et al. |
| D716,333 S | 10/2014 | Chotin et al. |
| 8,917,513 B1 | 12/2014 | Hazzard |
| 8,920,186 B2 | 12/2014 | Shishikura |
| 8,923,012 B2 | 12/2014 | Kaufman et al. |
| 8,968,296 B2 | 3/2015 | McPherson |
| 8,986,288 B2 | 3/2015 | Konishi |
| 9,017,326 B2 | 4/2015 | Dinardo et al. |
| D729,267 S | 5/2015 | Yoo et al. |
| 9,055,870 B2 | 6/2015 | Meador et al. |
| 9,065,394 B2 | 6/2015 | Lim et al. |
| 9,129,054 B2 | 9/2015 | Nawana et al. |
| 9,160,853 B1 | 10/2015 | Daddi et al. |
| 9,168,054 B2 | 10/2015 | Turner et al. |
| 9,168,085 B2 | 10/2015 | Juzkiw et al. |
| 9,168,091 B2 | 10/2015 | Janssen et al. |
| 9,198,711 B2 | 12/2015 | Joseph |
| 9,220,570 B2 | 12/2015 | Kim et al. |
| 9,226,766 B2 | 1/2016 | Aldridge et al. |
| 9,226,791 B2 | 1/2016 | McCarthy et al. |
| 9,237,921 B2 | 1/2016 | Messerly et al. |
| 9,265,429 B2 | 2/2016 | St. Pierre et al. |
| 9,277,961 B2 | 3/2016 | Panescu et al. |
| 9,277,969 B2 | 3/2016 | Brannan et al. |
| 9,281,615 B1 | 3/2016 | Plaza et al. |
| 9,320,646 B2 | 4/2016 | Todd et al. |
| 9,345,481 B2 | 5/2016 | Hall et al. |
| 9,345,900 B2 | 5/2016 | Wu et al. |
| 9,351,653 B1 | 5/2016 | Harrison |
| 9,427,255 B2 | 8/2016 | Griffith et al. |
| 9,463,646 B2 | 10/2016 | Payne et al. |
| 9,474,565 B2 | 10/2016 | Shikhman et al. |
| D772,252 S | 11/2016 | Myers et al. |
| 9,486,271 B2 | 11/2016 | Dunning |
| 9,491,895 B2 | 11/2016 | Steeves et al. |
| 9,503,681 B1 * | 11/2016 | Popescu ................ G06F 40/169 |
| 9,532,827 B2 | 1/2017 | Morgan et al. |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,629,176 B2 | 4/2017 | Guo et al. |
| 9,666,974 B2 | 5/2017 | Bopp |
| 9,713,503 B2 | 7/2017 | Goldschmidt |
| 9,715,271 B2 | 7/2017 | Kaestner |
| 9,750,563 B2 | 9/2017 | Shikhman et al. |
| 9,770,103 B2 | 9/2017 | Cochran et al. |
| 9,773,093 B2 | 9/2017 | Bernini et al. |
| 9,782,214 B2 | 10/2017 | Houser et al. |
| 9,788,907 B1 | 10/2017 | Alvi et al. |
| 9,804,977 B2 | 10/2017 | Ghosh et al. |
| 9,867,670 B2 | 1/2018 | Brannan et al. |
| 9,892,564 B1 | 2/2018 | Cvetko et al. |
| 9,907,196 B2 | 2/2018 | Susini et al. |
| 9,935,794 B1 | 4/2018 | Cao et al. |
| 9,971,395 B2 | 5/2018 | Chenault et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh et al. |
| 10,105,470 B2 | 10/2018 | Reasoner et al. |
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,019 B2 | 1/2019 | Nawana et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,262,453 B2 | 4/2019 | Mountney et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,441,345 B2 | 10/2019 | Aldridge et al. |
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,610,310 B2 | 4/2020 | Todd et al. |
| 10,624,667 B2 | 4/2020 | Faller et al. |
| 10,624,691 B2 | 4/2020 | Wiener et al. |
| 10,675,100 B2 | 6/2020 | Frushour |
| 10,687,884 B2 | 6/2020 | Wiener et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |
| 10,772,673 B2 | 9/2020 | Allen, IV et al. |
| 10,878,966 B2 | 12/2020 | Wolf et al. |
| 10,881,399 B2 | 1/2021 | Shelton, IV et al. |
| 10,898,256 B2 | 1/2021 | Yates et al. |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 10,989,724 B1 | 4/2021 | Holmes et al. |
| 11,000,270 B2 | 5/2021 | Scheib et al. |
| 11,006,100 B1 | 5/2021 | Douglas |
| D924,139 S | 7/2021 | Jayme |
| 11,056,244 B2 | 7/2021 | Shelton, IV et al. |
| 11,058,497 B2 | 7/2021 | Altmann et al. |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |
| 11,083,489 B2 | 8/2021 | Fujii et al. |
| 11,114,199 B2 | 9/2021 | Moctezuma De La Barrera |
| 11,116,587 B2 | 9/2021 | Wolf et al. |
| D939,545 S | 12/2021 | Oberkircher et al. |
| 11,218,822 B2 | 1/2022 | Morgan et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,284,963 B2 | 3/2022 | Shelton, IV et al. |
| 11,296,540 B2 | 4/2022 | Kirleis et al. |
| 11,298,128 B2 | 4/2022 | Messerly et al. |
| 11,304,763 B2 | 4/2022 | Shelton, IV et al. |
| 11,314,846 B1 | 4/2022 | Colin et al. |
| 11,341,726 B2 | 5/2022 | Tsuda et al. |
| 11,350,978 B2 | 6/2022 | Henderson et al. |
| 11,369,366 B2 | 6/2022 | Scheib et al. |
| 11,382,699 B2 | 7/2022 | Wassall et al. |
| 11,382,700 B2 | 7/2022 | Calloway et al. |
| 11,419,604 B2 | 8/2022 | Scheib et al. |
| 11,424,027 B2 | 8/2022 | Shelton, IV |
| 11,432,877 B2 | 9/2022 | Nash et al. |
| 11,464,581 B2 | 10/2022 | Calloway |
| 11,471,206 B2 | 10/2022 | Henderson et al. |

(56)                    References Cited

U.S. PATENT DOCUMENTS

| | | |
|---|---|---|
| 11,478,820 B2 | 10/2022 | Bales, Jr. et al. |
| 11,504,192 B2 | 11/2022 | Shelton, IV et al. |
| 11,510,720 B2 | 11/2022 | Morgan et al. |
| 11,510,750 B2 | 11/2022 | Dulin et al. |
| 11,823,374 B2 | 11/2023 | Schneider et al. |
| 11,836,863 B2 | 12/2023 | Flexman et al. |
| 12,349,861 B2 | 7/2025 | Charles et al. |
| 2001/0029315 A1 | 10/2001 | Sakurai et al. |
| 2003/0078631 A1 | 4/2003 | Nelson et al. |
| 2003/0199794 A1 | 10/2003 | Sakurai et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0111045 A1 | 6/2004 | Sullivan et al. |
| 2004/0164983 A1 | 8/2004 | Khozai |
| 2005/0010209 A1 | 1/2005 | Lee et al. |
| 2005/0013459 A1 | 1/2005 | Maekawa |
| 2005/0113823 A1 | 5/2005 | Reschke et al. |
| 2005/0165390 A1 | 7/2005 | Mauti et al. |
| 2005/0229110 A1 | 10/2005 | Gegner et al. |
| 2005/0251233 A1 | 11/2005 | Kanzius |
| 2006/0082542 A1 | 4/2006 | Morita et al. |
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0256516 A1 | 11/2006 | Cho |
| 2007/0076363 A1 | 4/2007 | Liang et al. |
| 2007/0211930 A1 | 9/2007 | Dolwick et al. |
| 2007/0282321 A1 | 12/2007 | Shah et al. |
| 2008/0072896 A1 | 3/2008 | Setzer et al. |
| 2008/0129465 A1 | 6/2008 | Rao |
| 2008/0249377 A1 | 10/2008 | Molducci et al. |
| 2008/0316304 A1 | 12/2008 | Claus et al. |
| 2009/0036884 A1 | 2/2009 | Gregg et al. |
| 2009/0131929 A1 | 5/2009 | Shimizu |
| 2009/0192524 A1 | 7/2009 | Itkowitz et al. |
| 2009/0216091 A1 | 8/2009 | Arndt |
| 2009/0234352 A1 | 9/2009 | Behnke et al. |
| 2010/0036405 A1 | 2/2010 | Giordano et al. |
| 2010/0042010 A1 | 2/2010 | Dekker et al. |
| 2010/0053213 A1 | 3/2010 | Ishida et al. |
| 2010/0069939 A1 | 3/2010 | Konishi |
| 2010/0076453 A1 | 3/2010 | Morris et al. |
| 2010/0092006 A1 | 4/2010 | Rosen |
| 2010/0120266 A1 | 5/2010 | Rimborg |
| 2010/0198200 A1 | 8/2010 | Horvath |
| 2010/0312239 A1 | 12/2010 | Selig |
| 2011/0105895 A1 | 5/2011 | Kornblau et al. |
| 2011/0118748 A1 | 5/2011 | Itkowitz |
| 2011/0125149 A1 | 5/2011 | El-Galley et al. |
| 2011/0130689 A1 | 6/2011 | Cohen et al. |
| 2011/0190588 A1 | 8/2011 | Mckay |
| 2011/0245630 A1 | 10/2011 | St. Pierre et al. |
| 2011/0273465 A1 | 11/2011 | Konishi et al. |
| 2011/0298814 A1 | 12/2011 | Mathew et al. |
| 2011/0306840 A1 | 12/2011 | Allen et al. |
| 2012/0029304 A1 | 2/2012 | Medina et al. |
| 2012/0082036 A1 | 4/2012 | Abedi et al. |
| 2012/0116380 A1 | 5/2012 | Madan et al. |
| 2012/0132661 A1 | 5/2012 | Gu et al. |
| 2013/0031201 A1 | 1/2013 | Kagan et al. |
| 2013/0038707 A1 | 2/2013 | Cunningham et al. |
| 2013/0176220 A1 | 7/2013 | Merschon et al. |
| 2013/0197357 A1 | 8/2013 | Green et al. |
| 2013/0197503 A1 | 8/2013 | Orszulak |
| 2013/0267975 A1 | 10/2013 | Timm et al. |
| 2013/0268283 A1 | 10/2013 | Vann et al. |
| 2013/0303851 A1 | 11/2013 | Griffith et al. |
| 2013/0321159 A1 | 12/2013 | Schofield et al. |
| 2014/0009894 A1 | 1/2014 | Yu |
| 2014/0052150 A1 | 2/2014 | Taylor et al. |
| 2014/0058714 A1 | 2/2014 | Boyer |
| 2014/0087573 A1 | 3/2014 | Kroeckel |
| 2014/0155721 A1 | 6/2014 | Hauck et al. |
| 2014/0179997 A1 | 6/2014 | Grunberg et al. |
| 2014/0194683 A1 | 7/2014 | Nakaguchi |
| 2014/0221740 A1 | 8/2014 | Kawula et al. |
| 2014/0226572 A1 | 8/2014 | Thota et al. |
| 2014/0262598 A1 | 9/2014 | Miki et al. |
| 2014/0263552 A1 | 9/2014 | Hall et al. |
| 2014/0343358 A1 | 11/2014 | Hameed et al. |
| 2015/0019259 A1 | 1/2015 | Qureshi et al. |
| 2015/0057575 A1 | 2/2015 | Tsusaka et al. |
| 2015/0070388 A1 | 3/2015 | Sheaffer et al. |
| 2015/0190189 A1 | 7/2015 | Yates et al. |
| 2015/0265369 A1 | 9/2015 | Garbey et al. |
| 2015/0272575 A1 | 10/2015 | Leimbach et al. |
| 2015/0289929 A1 | 10/2015 | Toth et al. |
| 2016/0045247 A1 | 2/2016 | Heim et al. |
| 2016/0058286 A1 | 3/2016 | Joshua et al. |
| 2016/0066184 A1 | 3/2016 | Bhargav-Spantzel et al. |
| 2016/0074096 A1 | 3/2016 | Lieu |
| 2016/0120591 A1 | 5/2016 | Smith et al. |
| 2016/0174897 A1 | 6/2016 | Sherman |
| 2016/0225192 A1 | 8/2016 | Jones et al. |
| 2016/0287312 A1 | 10/2016 | Tegg et al. |
| 2016/0287337 A1 | 10/2016 | Aram et al. |
| 2017/0000553 A1 | 1/2017 | Wiener et al. |
| 2017/0090507 A1 | 3/2017 | Wiener et al. |
| 2017/0189096 A1 | 7/2017 | Danziger et al. |
| 2017/0202595 A1 | 7/2017 | Shelton, IV |
| 2017/0209225 A1 | 7/2017 | Wu |
| 2017/0251305 A1 | 8/2017 | Fathollahi |
| 2017/0252091 A1 | 9/2017 | Honda |
| 2017/0258526 A1 | 9/2017 | Lang |
| 2017/0296036 A1 | 10/2017 | Newman |
| 2017/0296213 A1 | 10/2017 | Swensgard et al. |
| 2017/0319259 A1 | 11/2017 | Dunning |
| 2017/0333275 A1 | 11/2017 | Itkowitz et al. |
| 2017/0360466 A1 | 12/2017 | Brown et al. |
| 2017/0367766 A1* | 12/2017 | Mahfouz .............. A61B 8/4472 |
| 2018/0014872 A1 | 1/2018 | Dickerson |
| 2018/0032130 A1 | 2/2018 | Meglan |
| 2018/0042659 A1 | 2/2018 | Rupp et al. |
| 2018/0043037 A1 | 2/2018 | Dalma-Weiszhausz et al. |
| 2018/0049795 A1 | 2/2018 | Swayze et al. |
| 2018/0065248 A1 | 3/2018 | Barral et al. |
| 2018/0078216 A1 | 3/2018 | Baker et al. |
| 2018/0082480 A1 | 3/2018 | White et al. |
| 2018/0092699 A1 | 4/2018 | Finley |
| 2018/0099161 A1 | 4/2018 | Honda |
| 2018/0168741 A1 | 6/2018 | Swayze et al. |
| 2018/0173323 A1 | 6/2018 | Harvey et al. |
| 2018/0221005 A1 | 8/2018 | Hamel et al. |
| 2018/0228528 A1 | 8/2018 | Fraasch et al. |
| 2018/0228555 A1 | 8/2018 | Charron et al. |
| 2018/0235441 A1 | 8/2018 | Huang et al. |
| 2018/0243573 A1 | 8/2018 | Yoder et al. |
| 2018/0262916 A1 | 9/2018 | Polley et al. |
| 2018/0263557 A1 | 9/2018 | Kahlman |
| 2018/0289338 A1 | 10/2018 | Meador et al. |
| 2018/0317826 A1 | 11/2018 | Muhsin et al. |
| 2018/0333207 A1 | 11/2018 | Moctezuma De la Barrera |
| 2018/0368930 A1 | 12/2018 | Esterberg et al. |
| 2019/0006047 A1 | 1/2019 | Gorek et al. |
| 2019/0035153 A1 | 1/2019 | Dange |
| 2019/0038362 A1 | 2/2019 | Nash et al. |
| 2019/0069957 A1 | 3/2019 | Barral et al. |
| 2019/0104919 A1 | 4/2019 | Shelton, IV et al. |
| 2019/0117326 A1 | 4/2019 | Wada |
| 2019/0125361 A1 | 5/2019 | Shelton, IV et al. |
| 2019/0125451 A1 | 5/2019 | Srimohanarajah et al. |
| 2019/0125454 A1 | 5/2019 | Stokes et al. |
| 2019/0125455 A1 | 5/2019 | Shelton, IV et al. |
| 2019/0125459 A1 | 5/2019 | Shelton et al. |
| 2019/0183576 A1 | 6/2019 | Fahim et al. |
| 2019/0183591 A1 | 6/2019 | Johnson et al. |
| 2019/0200844 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0200987 A1 | 7/2019 | Shelton, IV et al. |
| 2019/0201046 A1 | 7/2019 | Shelton, IV et al. |
| 2019/0201102 A1 | 7/2019 | Shelton, IV et al. |
| 2019/0201114 A1* | 7/2019 | Shelton, IV .......... A61B 34/35 |

(56)  References Cited

U.S. PATENT DOCUMENTS

| | | |
|---|---|---|
| 2019/0201116 A1 | 7/2019 | Shelton, IV et al. |
| 2019/0201117 A1 | 7/2019 | Yates et al. |
| 2019/0201127 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201140 A1 | 7/2019 | Yates et al. |
| 2019/0201158 A1 | 7/2019 | Shelton, IV et al. |
| 2019/0205001 A1 | 7/2019 | Messerly et al. |
| 2019/0206004 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206565 A1 | 7/2019 | Shelton, IV |
| 2019/0206569 A1 | 7/2019 | Shelton et al. |
| 2019/0224434 A1 | 7/2019 | Silver et al. |
| 2019/0236840 A1 | 8/2019 | Zuckerman et al. |
| 2019/0247141 A1 | 8/2019 | Batchelor et al. |
| 2019/0278262 A1 | 9/2019 | Taylor et al. |
| 2019/0279524 A1 | 9/2019 | Stoyanov et al. |
| 2019/0282307 A1 | 9/2019 | Azizian et al. |
| 2019/0290297 A1 | 9/2019 | Haider et al. |
| 2019/0348169 A1 | 11/2019 | Gibby et al. |
| 2019/0371012 A1 | 12/2019 | Flexman et al. |
| 2020/0004487 A1 | 1/2020 | Hanajima et al. |
| 2020/0015895 A1 | 1/2020 | Frielinghaus et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015902 A1 | 1/2020 | Scheib et al. |
| 2020/0015906 A1 | 1/2020 | Scheib et al. |
| 2020/0015907 A1 | 1/2020 | Scheib |
| 2020/0015914 A1 | 1/2020 | Scheib et al. |
| 2020/0015924 A1 | 1/2020 | Scheib et al. |
| 2020/0038120 A1 | 2/2020 | Ziraknejad et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078078 A1 | 3/2020 | Henderson et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078083 A1 | 3/2020 | Sprinkle et al. |
| 2020/0078089 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0093357 A1 | 3/2020 | Scott et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0159313 A1 | 5/2020 | Gibby et al. |
| 2020/0237031 A1 | 7/2020 | Daniels et al. |
| 2020/0237452 A1 | 7/2020 | Wolf et al. |
| 2020/0246084 A1 | 8/2020 | Azizian |
| 2020/0268469 A1 | 8/2020 | Wolf et al. |
| 2020/0268472 A1 | 8/2020 | Wolf et al. |
| 2020/0305924 A1 | 10/2020 | Carroll |
| 2020/0305945 A1 | 10/2020 | Morgan et al. |
| 2020/0315707 A1 | 10/2020 | Venkataraman |
| 2020/0315734 A1 | 10/2020 | El Amm |
| 2020/0322516 A1 | 10/2020 | Doser et al. |
| 2020/0342228 A1 | 10/2020 | Prevrhal et al. |
| 2020/0359892 A1 | 11/2020 | Rollins et al. |
| 2020/0384287 A1 | 12/2020 | Hetz |
| 2020/0405529 A1 | 12/2020 | Taylor et al. |
| 2021/0000564 A1 | 1/2021 | Amanatullah et al. |
| 2021/0015343 A1 | 1/2021 | Uyama et al. |
| 2021/0093390 A1 | 4/2021 | Poltaretskyi et al. |
| 2021/0121246 A1 | 4/2021 | Gudalo |
| 2021/0128254 A1 | 5/2021 | Geric et al. |
| 2021/0158779 A1 | 5/2021 | Singh |
| 2021/0169578 A1 | 6/2021 | Calloway et al. |
| 2021/0169581 A1 | 6/2021 | Calloway et al. |
| 2021/0174956 A1 | 6/2021 | Mcginley et al. |
| 2021/0192759 A1 | 6/2021 | Lang |
| 2021/0193681 A1 | 6/2021 | Baek |
| 2021/0196381 A1 | 7/2021 | Eckert et al. |
| 2021/0196383 A1 | 7/2021 | Shelton, IV et al. |
| 2021/0196425 A1 | 7/2021 | Shelton et al. |
| 2021/0203889 A1 | 7/2021 | Fung et al. |
| 2021/0205020 A1 | 7/2021 | Shelton, IV et al. |
| 2021/0212717 A1 | 7/2021 | Yates et al. |
| 2021/0236755 A1 | 8/2021 | King et al. |
| 2021/0259789 A1 | 8/2021 | Wright et al. |
| 2021/0264680 A1 | 8/2021 | Cvetko et al. |
| 2021/0267664 A1 | 9/2021 | Lennartz et al. |
| 2021/0306691 A1 | 9/2021 | Thomas et al. |
| 2021/0307861 A1 | 10/2021 | Hufford et al. |
| 2021/0313052 A1 | 10/2021 | Makrinich et al. |
| 2021/0333864 A1 | 10/2021 | Harvey et al. |
| 2021/0346092 A1 | 11/2021 | Redmond et al. |
| 2021/0369394 A1 | 12/2021 | Braido et al. |
| 2021/0385889 A1 | 12/2021 | Patel |
| 2022/0032442 A1 | 2/2022 | Sheffield et al. |
| 2022/0104896 A1 | 4/2022 | Shelton, IV et al. |
| 2022/0104897 A1 | 4/2022 | Shelton, IV et al. |
| 2022/0104911 A1 | 4/2022 | Shelton, IV et al. |
| 2022/0104912 A1 | 4/2022 | Shelton, IV et al. |
| 2022/0142573 A1 | 5/2022 | Li et al. |
| 2022/0151704 A1 | 5/2022 | Nikou |
| 2022/0155910 A1 | 5/2022 | Jeong |
| 2022/0160428 A1 | 5/2022 | Murray et al. |
| 2022/0188545 A1 | 6/2022 | Nagar et al. |
| 2022/0237878 A1 | 7/2022 | Tartz et al. |
| 2022/0257333 A1 | 8/2022 | Haider |
| 2022/0261056 A1 | 8/2022 | Motoi et al. |
| 2022/0283631 A1 | 9/2022 | Peng |
| 2022/0287676 A1 | 9/2022 | Steines et al. |
| 2022/0313338 A1 | 10/2022 | Carroll et al. |
| 2022/0313341 A1 | 10/2022 | Wiener et al. |
| 2022/0313342 A1 | 10/2022 | Leuck et al. |
| 2022/0313357 A1 | 10/2022 | Geresy et al. |
| 2022/0313369 A1 | 10/2022 | Oberkircher et al. |
| 2022/0313370 A1 | 10/2022 | Morgan et al. |
| 2022/0313371 A1 | 10/2022 | Morgan et al. |
| 2022/0313372 A1 | 10/2022 | Herman et al. |
| 2022/0313373 A1 | 10/2022 | Morgan et al. |
| 2022/0317750 A1 | 10/2022 | Jayme et al. |
| 2022/0317751 A1 | 10/2022 | Samuel et al. |
| 2022/0318179 A1 | 10/2022 | Morgan et al. |
| 2022/0319685 A1 | 10/2022 | Vachon et al. |
| 2022/0319693 A1 | 10/2022 | Oberkircher et al. |
| 2022/0321059 A1 | 10/2022 | Samuel et al. |
| 2022/0322523 A1 | 10/2022 | Jayme et al. |
| 2022/0331013 A1 | 10/2022 | Shelton, IV et al. |
| 2022/0331047 A1 | 10/2022 | Shelton, IV et al. |
| 2022/0331048 A1 | 10/2022 | Shelton, IV et al. |
| 2022/0331049 A1 | 10/2022 | Shelton, IV et al. |
| 2022/0331050 A1 | 10/2022 | Shelton, IV et al. |
| 2022/0331051 A1 | 10/2022 | Shelton, IV et al. |
| 2022/0331052 A1 | 10/2022 | Shelton, IV et al. |
| 2022/0331053 A1 | 10/2022 | Kimball et al. |
| 2022/0331056 A1 | 10/2022 | Shelton, IV et al. |
| 2022/0334787 A1 | 10/2022 | Jogan et al. |
| 2022/0335604 A1 | 10/2022 | Vanosdoll et al. |
| 2022/0335660 A1 | 10/2022 | Shelton, IV et al. |
| 2022/0335696 A1 | 10/2022 | Shelton, IV et al. |
| 2022/0336078 A1 | 10/2022 | Wise et al. |
| 2022/0336097 A1 | 10/2022 | Shelton, IV et al. |
| 2022/0337891 A1 | 10/2022 | Burnley et al. |
| 2022/0338049 A1 | 10/2022 | Ross et al. |
| 2022/0387128 A1 | 12/2022 | Bail et al. |
| 2023/0038130 A1 | 2/2023 | Cvetko et al. |
| 2023/0061534 A1 | 3/2023 | Stopek |
| 2023/0071306 A1 | 3/2023 | Miller et al. |

(56)     References Cited

U.S. PATENT DOCUMENTS

| | | |
|---|---|---|
| 2023/0072423 A1 | 3/2023 | Osborn et al. |
| 2023/0121709 A1 | 4/2023 | Xu et al. |
| 2023/0157757 A1 | 5/2023 | Braido et al. |
| 2023/0157762 A1 | 5/2023 | Braido et al. |
| 2024/0130795 A1 | 4/2024 | Clayton et al. |
| 2024/0138931 A1 | 5/2024 | Lefauconnier |
| 2024/0176441 A1 | 5/2024 | Yang et al. |
| 2024/0325085 A1 | 10/2024 | Ryan et al. |

FOREIGN PATENT DOCUMENTS

| | | |
|---|---|---|
| EP | 0408160 A1 | 1/1991 |
| EP | 0473987 A1 | 3/1992 |
| EP | 0929263 B1 | 7/1999 |
| EP | 1006892 B1 | 6/2009 |
| EP | 2942023 A2 | 11/2015 |
| EP | 3053279 A1 | 8/2016 |
| EP | 3387982 A1 | 10/2018 |
| JP | 2000-271145 A | 10/2000 |
| JP | 2001029353 A | 2/2001 |
| JP | 2006-149560 A | 6/2006 |
| JP | 2007-007041 A | 1/2007 |
| JP | 2007-029232 A | 2/2007 |
| JP | 2021-045341 A | 3/2021 |
| WO | WO-0112089 A1 | 2/2001 |
| WO | WO-2008053485 A1 | 5/2008 |
| WO | 2014/010177 A1 | 1/2014 |
| WO | WO-2014031800 A1 | 2/2014 |
| WO | WO-2014071184 A1 | 5/2014 |
| WO | WO-2015047693 A1 | 4/2015 |
| WO | 2016/013636 A1 | 1/2016 |
| WO | 2016154557 A1 | 9/2016 |
| WO | WO-2017058617 A2 | 4/2017 |
| WO | 2017/099153 A1 | 6/2017 |
| WO | 2017/221367 A1 | 12/2017 |
| WO | WO-2018116247 A1 | 6/2018 |
| WO | WO-2019215354 A1 | 11/2019 |
| WO | 2020112217 A1 | 6/2020 |
| WO | 2020180917 A1 | 9/2020 |
| WO | WO-2021044136 A1 | 3/2021 |
| WO | 2021/146313 A1 | 7/2021 |

OTHER PUBLICATIONS

IEEE Std 802.3-2012 (Revision of IEEE Std 802.Mar. 2008, published Dec. 28, 2012.

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

Zhu et al. "Haptic-feedback smart glove as a creative human-machine interface (HMI) for virtual/augmented reality applications," SCI. ADV, vol. 6, No. 19, May 8, 2020.

Qian, et al., "A Review of Augmented Reality in Robotic-Assisted Surgery", IEEE Transactions on Medical Robotics and Bionics, IEEE, vol. 2, No. 1, pp. 1-16, Feb. 2020.

Yu et al., "Skin-Integrated Wireless Haptic Interfaces for Virtual and Augmented Reality," Nature, vol. 575, pp. 473-479, Nov. 21, 2019.

Li et al., "Wearable Energy Harvesters Generating Electricity From Low-Frequency Human Limb Movement," Microsystems & Nanoengineering (2018), vol. 4(24), 13 pages.

Vávra et al., "Recent Development of Augmented Reality in Surgery: A Review", Journal of Healthcare Engineering, vol. 2017, Article ID 4574172, Aug. 21, 2017, pp. 1-9.

Zherdeva, et al., "Virtual Scalpel Simulation in the VR and AR Environments", Proceedings of SPIE, vol. 11310, Feb. 19, 2020, 7 pages.

International Search Report and Written Opinion received for PCT Application No. PCT/IB2022/053360 mailed on Jul. 4, 2022, 12 pages.

International Search Report and Written Opinion received for PCT Application No. PCT/IB2022/053362 mailed on Jul. 1, 2022, 13 pages.

International Search Report and Written Opinion received for PCT Application No. PCT/IB2022/053363 mailed on Jun. 30, 2022, 14 pages.

International Search Report and Written Opinion received for PCT Application No. PCT/IB2022/053364 mailed on Jul. 8, 2022, 11 pages.

International Search Report and Written Opinion received for PCT Application No. PCT/IB2022/053365 mailed on Jul. 4, 2022, 16 pages.

International Search Report and Written Opinion received for PCT Application No. PCT/IB2022/053369 mailed on Jul. 13, 2022, 12 pages.

International Search Report and Written Opinion received for PCT Application No. PCT/IB2022/053370 mailed on Jul. 15, 2022, 14 pages.

International Search Report and Written Opinion received for PCT Application No. PCT/IB2022/053371 mailed on Jul. 5, 2022, 12 pages.

International Search Report and Written Opinion received for PCT Application No. PCT/IB2022/053375 mailed on Oct. 4, 2022, 22 pages.

International Search Report and Written Opinion received for PCT Application No. PCT/IB2022/053377 mailed on Jun. 22, 2022, 12 pages.

International Search Report and Written Opinion received for PCT Application No. PCT/IB2022/053378 mailed on Jul. 7, 2022, 13 pages.

Invitation to Pay Additional Fees received for PCT Application No. PCT/IB2022/053375 mailed on Jul. 15, 2022, 11 pages.

Kaushik et al., "Emerging Thermal Technology Enabled Augmented Reality", Advanced Functional Materials, vol. 31, No. 39, Feb. 17, 2021., pp. 1-27.

* cited by examiner

Clamping On Metal Or Foreign Object

Alert! Foreign Object

Figure 38:
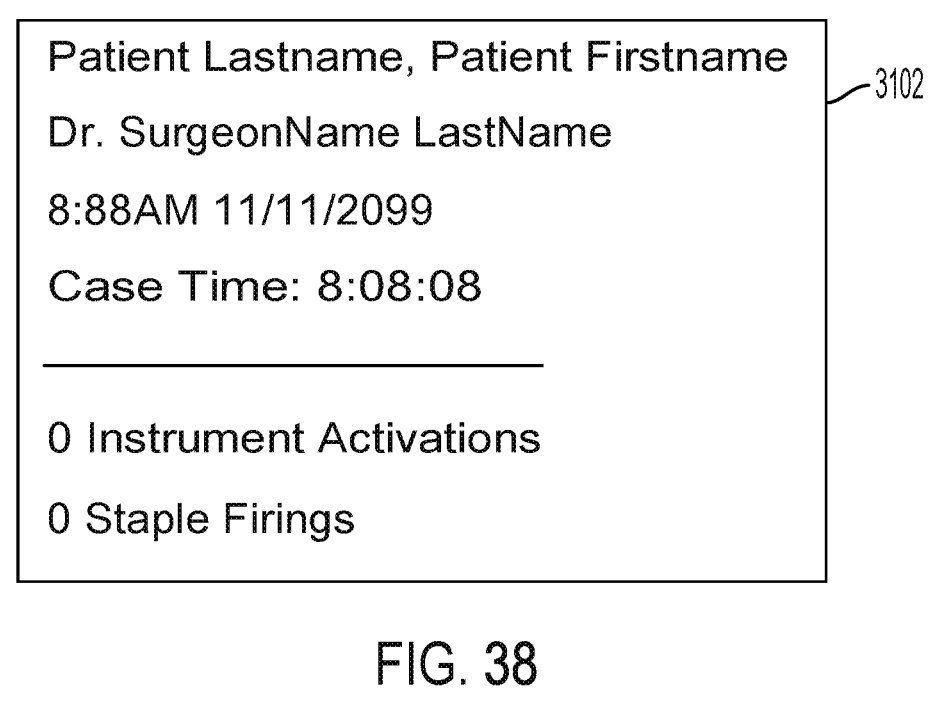

Patient Lastname, Patient Firstname

Dr. SurgeonName LastName

8:88AM 11/11/2099

Case Time: 8:08:08

———————————————

0 Instrument Activations

0 Staple Firings

Device Panel
3106

3132

Device Name

3134

Device
Settings

3136

Device
Supplemental
Feature

3140

3142

Stacked
Configuration

Expanded
Configuration

3144

3150

Activate instrument for 2 seconds to
run test.

3400

Device Panel
4000

4002
Device Panel
Name

4004
Device Panel
Supplemental
Feature

4010

4060

| Category ▾ | Concept ▾ | Description ▾ |
|---|---|---|
| Pairing | ☆ User Selectable Pairing | The user would start a pairing mode on the capital equipment via a touchscreen. The capital equipment would then attempt to identify all valid devices of that type within a region, and the user would simply select the devices that they would like to connect to. Would like to continue broadcasting even after time has elapsed |
| Pairing | ☆ Connect on Powerup | Could enable bluetooth radio on powerup for the surgical device, if not connected to client within time, turn it off. The capital equipment is constantly scanning for new devices and connects to it. |
| Pairing | Connect on Powerup with Button Press | Could enable bluetooth radio on powerup for the surgical device, if not connected to client within time, turn it off. The capital equipment has a pairing button pressed, and once pressed scans / connects to the Surgical device. |
| Pairing | ☆ RFID Token | The user utilizes an RFID card, packaged with each device, as a method for scanning in the new device and pairing with the capital equipment. |

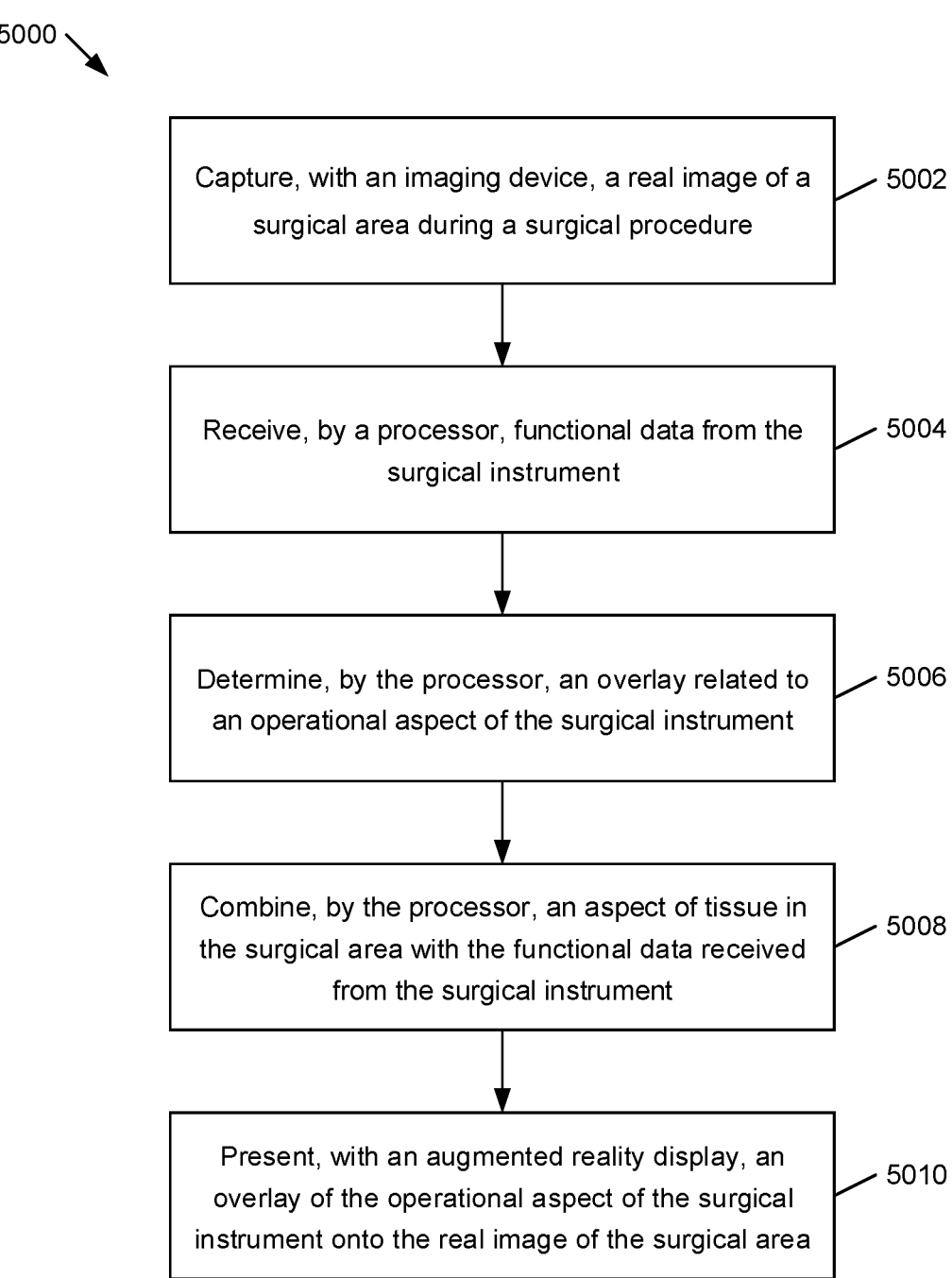

5000

Capture, with an imaging device, a real image of a surgical area during a surgical procedure — 5002

Receive, by a processor, functional data from the surgical instrument — 5004

Determine, by the processor, an overlay related to an operational aspect of the surgical instrument — 5006

Combine, by the processor, an aspect of tissue in the surgical area with the functional data received from the surgical instrument — 5008

Present, with an augmented reality display, an overlay of the operational aspect of the surgical instrument onto the real image of the surgical area — 5010

FIG. 69

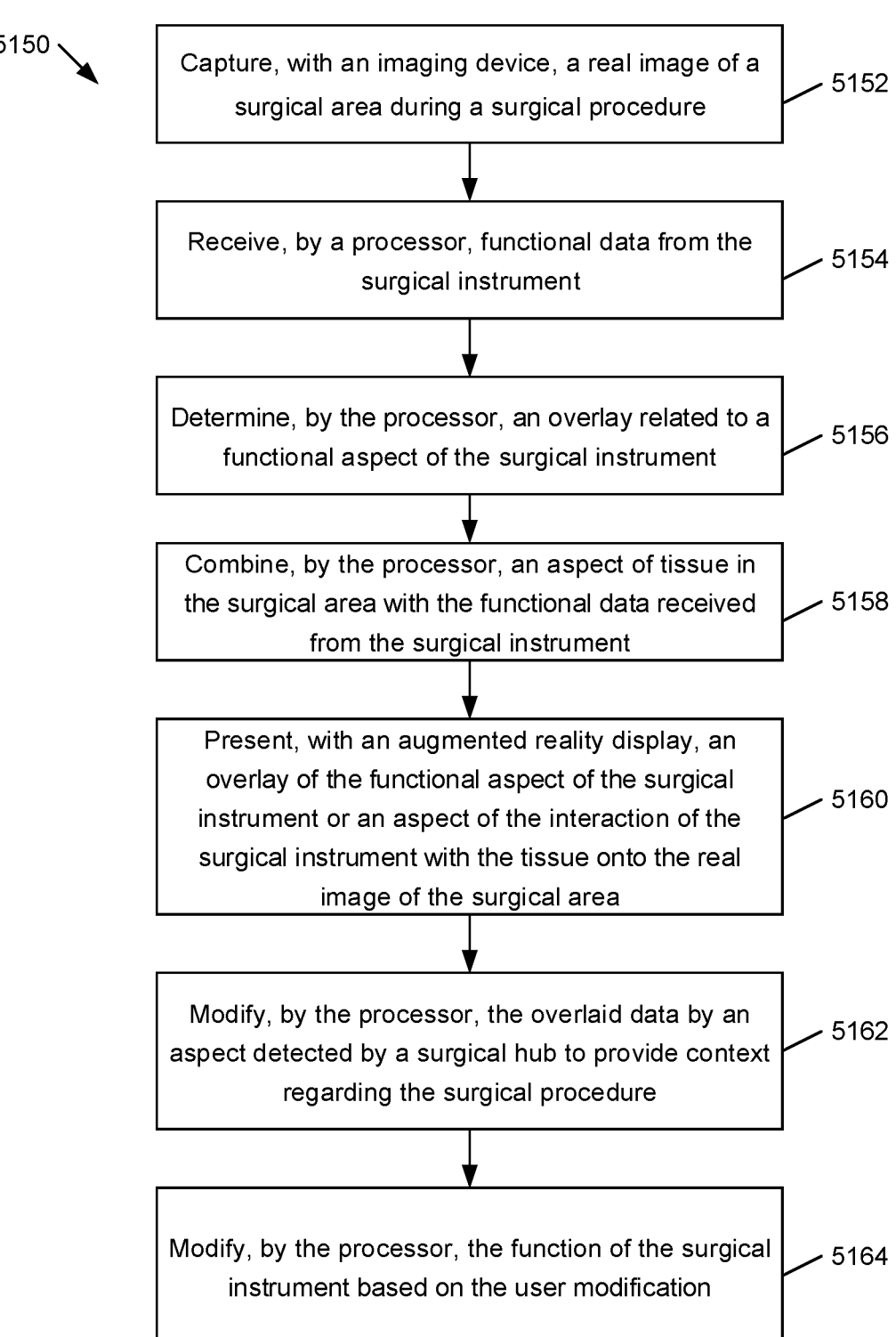

5150

Capture, with an imaging device, a real image of a surgical area during a surgical procedure — 5152

Receive, by a processor, functional data from the surgical instrument — 5154

Determine, by the processor, an overlay related to a functional aspect of the surgical instrument — 5156

Combine, by the processor, an aspect of tissue in the surgical area with the functional data received from the surgical instrument — 5158

Present, with an augmented reality display, an overlay of the functional aspect of the surgical instrument or an aspect of the interaction of the surgical instrument with the tissue onto the real image of the surgical area — 5160

Modify, by the processor, the overlaid data by an aspect detected by a surgical hub to provide context regarding the surgical procedure — 5162

Modify, by the processor, the function of the surgical instrument based on the user modification — 5164

FIG. 71

Staff View Detailed Customization Pop-up

ADAPTATION AND ADJUSTABILITY OR OVERLAID INSTRUMENT INFORMATION FOR SURGICAL SYSTEMS

CROSS-REFERENCE TO RELATED APPLICATIONS

This application claims the benefit under 35 U.S.C. § 119(e) to U.S. Provisional Patent Application No. 63/174,674, titled HEADS UP DISPLAY, filed Apr. 14, 2021 and to U.S. Provisional Patent Application No. 63/284,326, titled INTRAOPERATIVE DISPLAY FOR SURGICAL SYSTEMS, filed Nov. 30, 2021, the disclosure of each of which is herein incorporated by reference in its entirety.

BACKGROUND

This disclosure relates to apparatuses, systems, and methods for providing an augmented reality interactive experience during a surgical procedure. During a surgical procedure it would be desirable to provide an augmented reality interactive experience of a real-world environment where objects that reside in the real world are enhanced by overlaying computer-generated perceptual information, sometimes across multiple sensory modalities, including visual, auditory, haptic, somatosensory, and olfactory. In the context of this disclosure, images of a surgical field and surgical instruments and other objects appearing in the surgical field are enhanced by overlaying computer-generated visual, auditory, haptic, somatosensory, olfactory, or other sensory information onto the real world images of the surgical field and instruments or other objects appearing in the surgical field. The images may be streamed in real time or may be still images.

Real world surgical instruments include a variety of surgical devices. Energy based surgical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices are instruments used to cut and staple tissue in a variety of surgical procedures, including bariatric, thoracic, colorectal, gynecologic, urologic and general surgery.

SUMMARY

In various instances, this disclosure provides an augmented reality display system for use during a surgical procedure. The augmented reality display system comprises an imaging device to capture a real image of a surgical area during the surgical procedure. An augmented reality display presents a functional data overlay associated with critical operations of a surgical instrument being actively visualized and interactions of the surgical instrument with tissue in the surgical area. The functional data is overlaid onto the real image of the surgical area. The functional data overlay is a combination of aspects of the critical operations of the surgical instrument and the interaction of the surgical instrument with the tissue in the surgical area. A processor receives functional data from the surgical instrument, determines the overlaid data related to the functional aspect of the surgical instrument, and combines the aspect of the tissue in the surgical area with the functional data received from the surgical instrument.

In various instances this disclosure provides, an augmented reality display system for use during a surgical procedure. The augmented reality display system comprises an imaging device to capture a real image of a surgical area during the surgical procedure. An augmented reality display presents a functional data overlay associated with parameters of a surgical instrument being actively visualized and interactions of the surgical instrument with tissue in the surgical area. The functional data is overlaid onto the real image of the surgical area, and wherein the functional data overlay is a combination of aspects of the parameters of the surgical instrument and the interaction of the surgical instrument with the tissue in the surgical area. A processor receives functional data from the surgical instrument, determines the overlaid data related to the functional aspect of the surgical instrument, and combines the aspect of the tissue in the surgical area with the functional data received from the surgical instrument.

In various instances, the present disclosure provides a system comprising an augmented reality display system for use during a surgical procedure, The augmented reality display system comprises an imaging device to capture a real image of a surgical area during the surgical procedure. An augmented reality display presents a functional data overlay associated with a surgical instrument; an energy generator coupled to the surgical instrument. The surgical instrument employs radio frequency (RF) energy and ultrasonic energy during a surgical procedure. A surgical hub is coupled to the energy generator and to the augmented reality display. The surgical hub provides a live feed of the surgical area to the augmented reality display to display the live feed of the surgical area. The augmented reality display displays a view of the surgical area, the surgical instrument, and a panel overlay to display information specific to critical operations or parameters of the surgical instrument and interactions of the surgical instrument with tissue if the surgical area.

FIGURES

The various aspects described herein, both as to organization and methods of operation, together with further objects and advantages thereof, may best be understood by reference to the following description, taken in conjunction with the accompanying drawings as follows.

FIG. 38 is a detailed view of the case information panel overlay shown in FIG. 37, according to one aspect of this disclosure.

FIG. 65 is a chart describing pairing a surgical stapler instrument, according to one aspect of this disclosure.

FIG. 69 is a diagram of an augmented reality method employing a surgical instrument and an augmented reality display for use during a surgical procedure, according to one aspect of this disclosure.

FIG. 71 is a diagram of an augmented reality method employing a surgical instrument and an augmented reality display for use during a surgical procedure, according to one aspect of this disclosure.

Corresponding reference characters indicate correspond-ing parts throughout the several views. The exemplifications set out herein illustrate various disclosed embodiments, in one form, and such exemplifications are not to be construed as limiting the scope thereof in any manner.

DESCRIPTION

Figure 1:
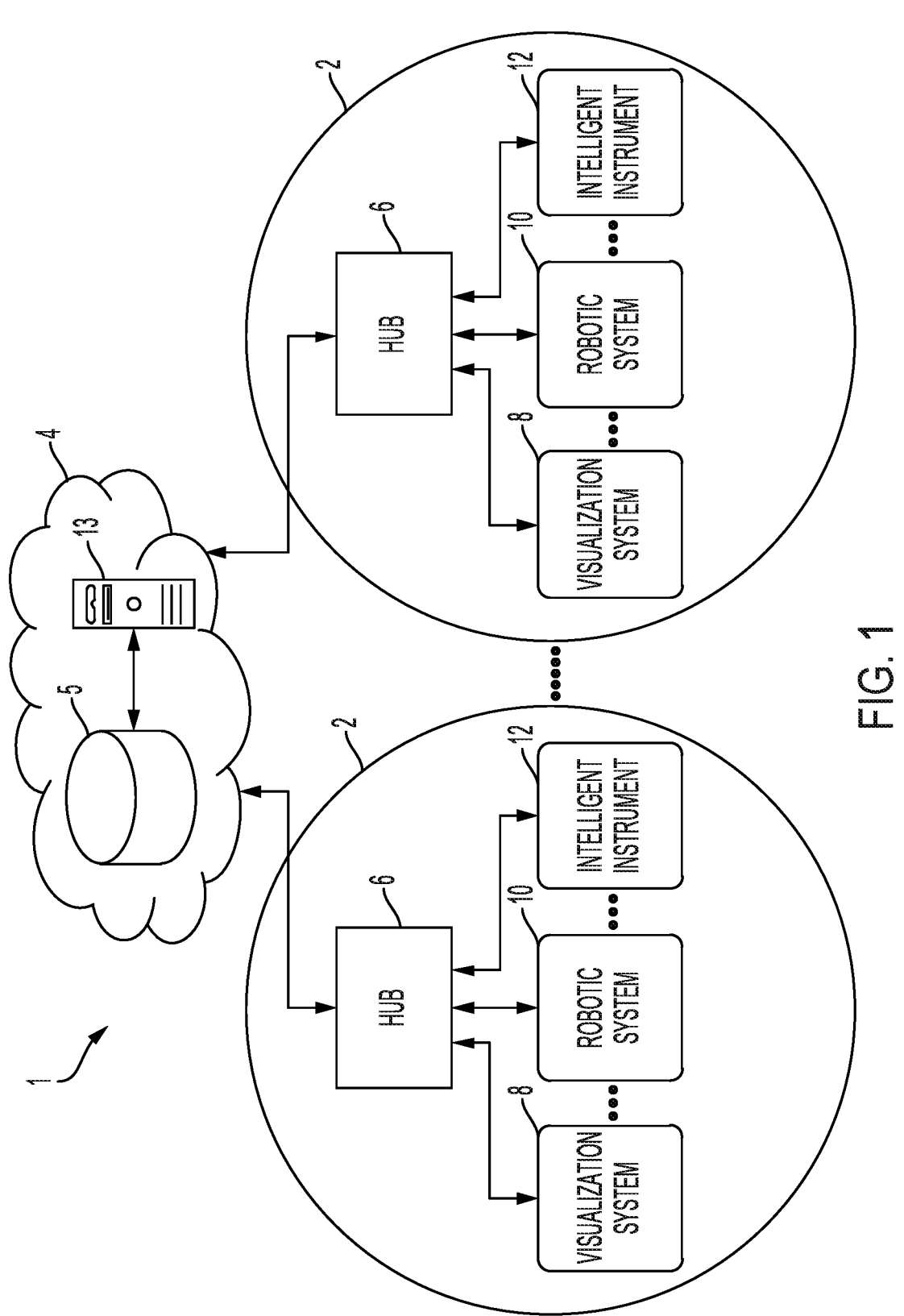
FIG. 1 is a block diagram of a computer-implemented interactive surgical system, according to one aspect of this disclosure.

Applicant of the present application owns the following U.S. patent applications filed concurrently herewith, the disclosures of each of which is herein incorporated by reference in its entirety:

U.S. patent application Ser. No. 17/688,589, titled METHOD FOR INTRAOPERATIVE DISPLAY FOR SURGICAL SYSTEMS;

U.S. patent application Ser. No. 17/688,597, titled Utilization of surgical data values and situational awareness to control the overlay in surgical field view;

U.S. patent application Ser. No. 17/688,605, titled SELECTIVE AND ADJUSTABLE MIXED REALITY OVERLAY IN SURGICAL FIELD VIEW;

U.S. patent application Ser. No. 17/688,615, titled RISK BASED PRIORITIZATION OF DISPLAY ASPECTS IN SURGICAL FIELD VIEW;

U.S. patent application Ser. No. 17,688,626, titled SYSTEMS AND METHODS FOR CONTROLLING SURGICAL DATA OVERLAY;

U.S. patent application Ser. No. 17/688,633, titled SYSTEMS AND METHODS FOR CHANGING DISPLAY OVERLAY OF SURGICAL FIELD VIEW BASED ON TRIGGERING EVENTS;

U.S. patent application Ser. No. 17/688,638, titled CUSTOMIZATION OF OVERLAID DATA AND CONFIGURATION;

U.S. patent application Ser. No. 17/688,638, titled INDICATION OF THE COUPLE PAIR OF REMOTE CONTROLS WITH REMOTE DEVICES FUNCTIONS;

U.S. patent application Ser. No. 17/688,646, titled COOPERATIVE OVERLAYS OF INTERACTING INSTRUMENTS WHICH RESULT IN BOTH OVERLAYS BEING EFFECTED;

U.S. patent application Ser. No. 17/688,651, titled ANTICIPATION OF INTERACTIVE UTILIZATION OF COMMON DATA OVERLAYS BY DIFFERENT USERS;

U.S. patent application Ser. No. 17/688,653, titled MIXING DIRECTLY VISUALIZED WITH RENDERED ELEMENTS TO DISPLAY BLENDED ELEMENTS AND ACTIONS HAPPENING ON-SCREEN AND OFF-SCREEN;

U.S. patent application Ser. No. 17/688,655, titled SYSTEM AND METHOD FOR TRACKING A PORTION OF THE USER AS A PROXY FOR NON-MONITORED INSTRUMENT;

U.S. patent application Ser. No. 17/688,656, titled UTILIZING CONTEXTUAL PARAMETERS OF ONE OR MORE SURGICAL DEVICES TO PREDICT A FREQUENCY INTERVAL FOR DISPLAYING SURGICAL INFORMATION;

U.S. patent application Ser. No. 17/688,660, titled COOPERATION AMONG MULTIPLE DISPLAY SYSTEMS TO PROVIDE A HEALTHCARE USER CUSTOMIZED INFORMATION;

U.S. patent application Ser. No. 17/688,663, titled INTRAOPERATIVE DISPLAY FOR SURGICAL SYSTEMS; and U.S. patent application Ser. No. 17/688,671, titled MIXED REALITY FEEDBACK SYSTEMS THAT COOPERATE TO INCREASE EFFICIENT PERCEPTION OF COMPLEX DATA FEEDS;

Applicant of this application owns the following U.S. patent applications, the disclosure of each of which is herein incorporated by reference in its entirety:

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Publication No. US-2019-0200981-A1;

U.S. patent application Ser. No. 16/209,453, titled METHOD FOR CONTROLLING SMART ENERGY DEVICES, now U.S. Patent Publication No. US-2019-0201046-A1.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to onscreen displays for surgical systems for a variety of energy and surgical stapler based medical devices. Energy based medical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices include and combined surgical staplers with electrosurgical and/or ultrasonic devices. Aspects of the ultrasonic surgical devices can be configured for transecting and/or coagulating tissue during surgical procedures, for example. Aspects of the electrosurgical devices can be configured for transecting, coagulating, sealing, welding and/or desiccating tissue during surgical procedures, for example. Aspects of the surgical stapler devices can be configured for transecting and stapling tissue during surgical procedures and in some aspects, the surgical stapler devices may be configured to delivery RF energy to the tissue during surgical procedures. Electrosurgical devices are configured to deliver therapeutic and/or nontherapeutic RF energy to the tissue. Elements of surgical staplers, electrosurgical, and ultrasonic devices may be used in combination in a single surgical instrument.

In various aspects, the present disclosure provides onscreen displays of real time information to the OR team during a surgical procedure. In accordance with various aspects of the present disclosure, many new and unique onscreen displays are provided to display onscreen a variety of visual information feedback to the OR team. According to the present disclosure, visual information may comprise one or more than one of various visual media with or without sound. Generally, visual information comprises still photography, motion picture photography, video or audio recording, graphic arts, visual aids, models, display, visual presentation services, and the support processes. The visual information can be communicated on any number of display options such as the primary OR screen, the energy or surgical stapler device itself, a tablet, augmented reality glasses, among others, for example.

In various aspects, the present disclosure provides a large list of potential options to communicate visual information in real time to the OR team, without overwhelming the OR team with too much visual information. For example, in various aspects, the present disclosure provides onscreen displays of visual information to enable the surgeon, or other members of the OR team, to selectively activate onscreen displays such as icons surrounding the screen option to manage a wealth of visual information. One or a combination of factors can be used to determine the active display, these may include energy based (e.g., electrosurgical, ultrasonic) or mechanical based (e.g., staplers) surgical devices in use, the estimated risk associated with a given display, the experience level of the surgeon and the surgeons' choice among other things. In other aspect, the visual information may comprises rich data overlaid or superimposed into the surgical field of view to manage the visual information. In various aspects described hereinbelow, comprise superimposed imagery that requires video analysis and tracking to properly overlay the data. Visual information data communicated in this manner, as opposed to static icons, may provide additional useful visual information in a more concise and easy to understand way to the OR team.

In various aspects, the present disclosure provides techniques for selectively activating onscreen displays such as icons surrounding the screen to manage visual information during a surgical procedure. In other aspects, the present disclosure provides techniques for determining the active display using one or a combination of factors. In various aspects, the techniques according to the resent disclosure may comprise selecting the energy based or mechanical based surgical device in use as the active display, estimating risk associated with a given display, utilizing the experience level of the surgeon or OR team making the selection, among other things.

In other aspects, the techniques according to the present disclosure may comprise overlaying or superimposing rich data onto the surgical field of view to manage the visual information. A number of the display arrangements described by the present disclosure involve overlaying various visual representations of surgical data onto a livestream of a surgical field. As used herein the term overlay comprises a translucent overlay, a partial overlay, and/or a moving overlay. Graphical overlays may be in the form of a transparent graphic, semitransparent graphic, or opaque graphic, or a combination of transparent, semitransparent, and opaque elements or effects. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values. The graphical overlays are rendered on top of the active display monitor to convey important information quickly and efficiently to the OR team.

In other aspects, the techniques according to the present disclosure may comprise superimposing imagery that requires analyzing video and tracking for properly overlaying the visual information data. In other aspects, the techniques according to the present disclosure may comprise communicating rich visual information, as opposed to simple static icons, to provide additional visual information to the OR team in a more concise and easy to understand manner. In other aspects, the visual overlays may be used in combination with audible and/or somatosensory overlays such as thermal, chemical, and mechanical devices, and combinations thereof.

The following description is directed generally to apparatuses, systems, and methods that provide an augmented reality (AR) interactive experience during a surgical procedure. In this context, images of a surgical field and surgical instruments and other objects appearing in the surgical field are enhanced by overlaying computer-generated visual, auditory, haptic, somatosensory, olfactory, or other sensory information onto the real world images of the surgical field, instruments, and/or other objects appearing in the surgical field. The images may be streamed in real time or may be still images. Augmented reality is a technology for rendering and displaying virtual or "augmented" virtual objects, data, or visual effects overlaid on a real environment. The real environment may include a surgical field. The virtual objects overlaid on the real environment may be represented as anchored or in a set position relative to one or more aspects of the real environment. In a non-limiting example, if a real world object exits the real environment field of view, a virtual object anchored to the real world object would also exit the augmented reality field of view.

A number of the display arrangements described by the present disclosure involve overlaying various visual representations of surgical data onto a livestream of a surgical field. As used herein the term overlaying comprises a translucent overlay, a partial overlay, and/or a moving overlay. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values.

As described herein AR is an enhanced version of the real physical world that is achieved through the use of digital visual elements, sound, or other sensory stimuli delivered via technology. Virtual Reality (VR) is a computer-generated environment with scenes and objects that appear to be real, making the user feel they are immersed in their surroundings. This environment is perceived through a device known as a Virtual Reality headset or helmet. Mixed reality (MR) and AR are both considered immersive technologies, but they aren't the same. MR is an extension of Mixed reality that allows real and virtual elements to interact in an environment. While AR adds digital elements to a live view often by using a camera, an MR experience combines elements of both AR and VR, where real-world and digital objects interact.

In an AR environment, one or more computer-generated virtual objects may be displayed along with one or more real (i.e., so-called "real world") elements. For example, a real-time image or video of a surrounding environment may be shown on a computer screen display with one or more overlaying virtual objects. Such virtual objects may provide complementary information relating to the environment or generally enhance a user's perception and engagement with the environment. Conversely, the real-time image or video of the surrounding environment may additionally or alternatively enhance a user's engagement with the virtual objects shown on the display.

The apparatuses, systems, and methods in the context of this disclosure enhance images received from one or more imaging devices during a surgical procedure. The imaging devices may include a variety of scopes used during non-invasive and minimally invasive surgical procedures, an AR device, and/or a camera to provide images during open surgical procedures. The images may be streamed in real time or may be still images. The apparatuses, systems, and methods provide an augmented reality interactive experience by enhancing images of the real world surgical environment by overlaying virtual objects or representations of data and/or real objects onto the real surgical environment. The augmented reality experience may be viewed on a display and/or an AR device that allows a user to view the overlaid virtual objects onto the real world surgical environment. The display may be located in the operating room or remote from the operating room. AR devices are worn on the head of the surgeon or other operating room personnel and typically include two stereo-display lenses or screens, including one for each eye of the user. Natural light is permitted to pass through the two transparent or semi-transparent display lenses such that aspects of the real environment are visible while also projecting light to make virtual objects visible to the user of the AR device.

Two or more displays and AR devices may be used in a coordinated manner, for example with a first display or AR device controlling one or more additional displays or AR devices in a system with defined roles. For example, when activating display or an AR device, a user may select a role (e.g., surgeon, surgical assistant, nurse, etc., during a surgical procedure) and the display or AR device may display information relevant to that role. For example, a surgical assistant may have a virtual representation of an instrument displayed that the surgeon needs to perform for a next step of a surgical procedure. A surgeon's focus on the current step may see different information displayed than the surgical assistant.

Although there are many known onscreen displays and alerts, this disclosure provides many new and unique augmented reality interactive experiences during a surgical procedure. Such augmented reality interactive experiences include visual, auditory, haptic, somatosensory, olfactory, or other sensory feedback information to the surgical team inside or outside the operating room. The virtual feedback information overlaid onto the real world surgical environment may be provided to an operating room (OR) team, including personnel inside the OR including, without limitation, the operating surgeon, assistants to the surgeon, a scrub person, an anesthesiologist and a circulating nurse, among others, for example. The virtual feedback information can be communicated on any number of display options such as a primary OR screen display, an AR device, the energy or surgical stapler instrument, a tablet, augmented reality glasses, device etc.

FIG. 1 depicts a computer-implemented interactive surgical system 1 that includes one or more surgical systems 2 and a cloud-based system 4. The cloud-based system 4 may include a remote server 13 coupled to a storage device 5. Each surgical system 2 includes at least one surgical hub 6 in communication with the cloud 4. For example, the surgical system 2 may include a visualization system 8, a robotic system 10, and handheld intelligent surgical instruments 12, each configured to communicate with one another and/or the hub 6. In some aspects, a surgical system 2 may include an M number of hubs 6, an N number of visualization systems 8, an O number of robotic systems 10, and a P number of handheld intelligent surgical instruments 12, where M, N, O, and P are integers greater than or equal to one. The computer-implemented interactive surgical system 1 may be configured to provide an augmented reality interactive experience during a surgical procedure as described herein.

Figure 2:
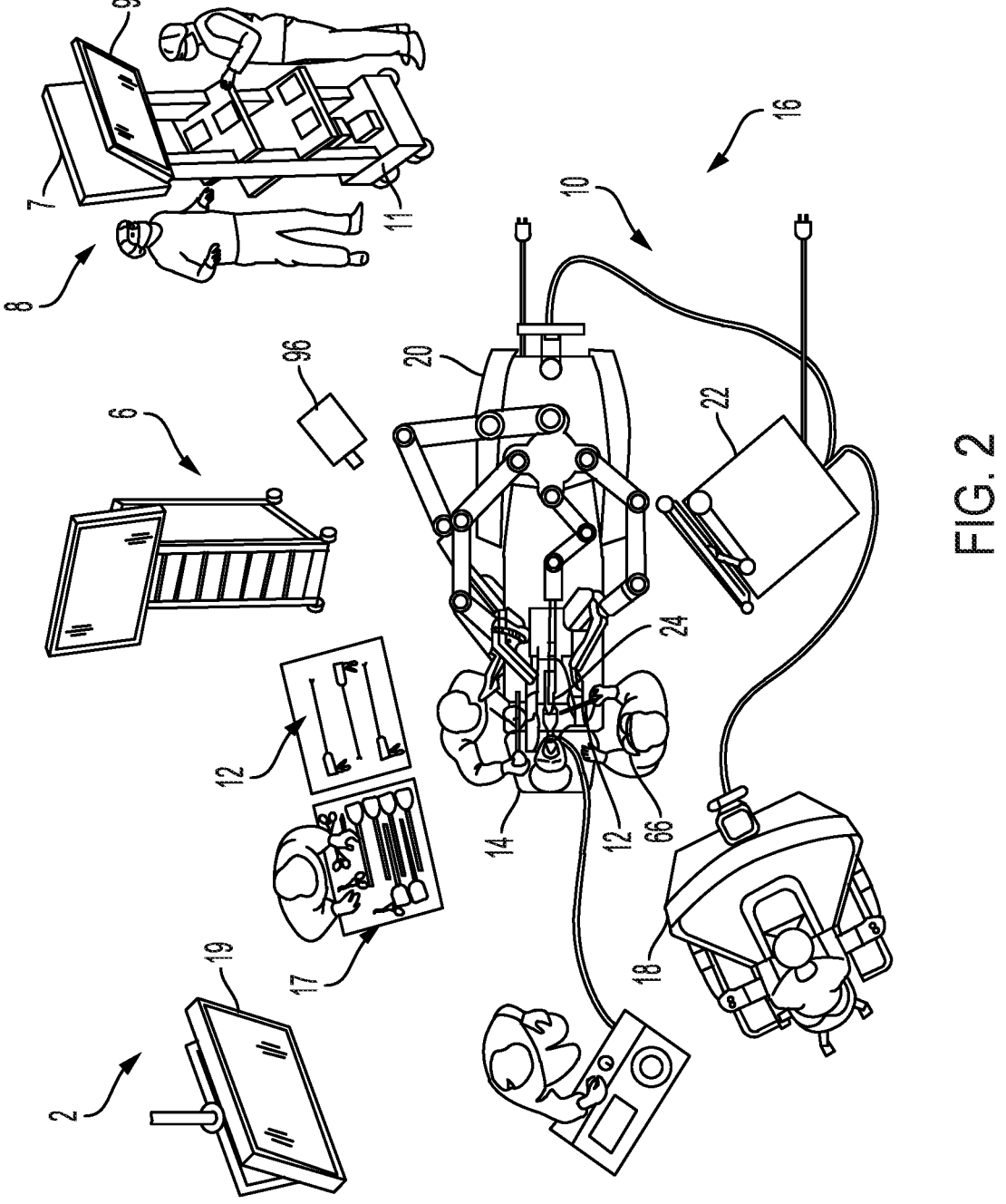
FIG. 2 is a surgical system being used to perform a surgical procedure in an operating room, according to one aspect of this disclosure.

FIG. 2 depicts an example of a surgical system 2 to perform a surgical procedure on a patient lying down on an operating table 14 in a surgical operating room 16. A robotic system 10 is used in the surgical procedure as a part of the surgical system 2. The robotic system 10 includes a surgeon's console 18, a patient side cart 20 (surgical robot), and a surgical robotic hub 22. The patient side cart 20 can manipulate at least one removably coupled surgical tool 17 through a minimally invasive incision in the body of the patient while the surgeon views the surgical site through the surgeon's console 18 or an augmented reality (AR) device 66 worn by the surgeon. An image (e.g., still or live streamed in real time) of the surgical site during a minimally invasive procedure can be obtained by a medical imaging device 24. The patient side cart 20 can manipulate the imaging device 24 to orient the imaging device 24. An image of an open surgical procedure can be obtained by a medical imaging device 96. The robotic hub 22 processes the images of the surgical site for subsequent display on the surgeon's console 18 or the AR device 66 worn by the surgeon, or other person in the surgical operating room 16.

The optical components of the imaging device 24, 96 or AR device 66 may include one or more illumination sources and/or one or more lenses. The one or more illumination sources may be directed to illuminate portions of the surgical field. One or more image sensors may receive light reflected or refracted from tissue and instruments in the surgical field.

In various aspects, the imaging device 24 is configured for use in a minimally invasive surgical procedure. Examples of imaging devices suitable for use with this disclosure include, but not limited to, an arthroscope, angioscope, broncho-scope, choledochoscope, colonoscope, cytoscope, duodeno-scope, enteroscope, esophagogastro-duodenoscope (gastro-scope), endoscope, laryngoscope, nasopharyngo-neproscope, sigmoidoscope, thoracoscope, and ureteroscope. In various aspects, the imaging device 96 is configured for use in an open (invasive) surgical procedure.

In various aspects, the visualization system 8 includes one or more imaging sensors, one or more image-processing units, one or more storage arrays, and one or more displays that are strategically arranged with respect to the sterile field. In one aspect, the visualization system 8 includes an interface for HL7, PACS, and EMR. In one aspect, the imaging device 24 may employ multi-spectrum monitoring to discriminate topography and underlying structures. A multi-spectral image captures image data within specific wavelength ranges in the electromagnetic spectrum. Wavelengths are separated by filters or instruments sensitive to particular wavelengths, including light from frequencies beyond the visible light range, e.g., IR and ultraviolet. Spectral imaging can extract information not visible to the human eye. Multi-spectrum monitoring can relocate a surgical field after a surgical task is completed to perform tests on the treated tissue.

FIG. 2 depicts a primary display 19 positioned in the sterile field to be visible to an operator at the operating table 14. A visualization tower 11 is positioned outside the sterile field and includes a first non-sterile display 7 and a second non-sterile display 9, which face away from each other. The visualization system 8, guided by the hub 6, is configured to utilize the displays 7, 9, 19 to coordinate information flow to operators inside and outside the sterile field. For example, the hub 6 may cause the visualization system 8 to display AR images of the surgical site, as recorded by an imaging device 24, 96 on a non-sterile display 7, 9, or through the AR device 66, while maintaining a live feed of the surgical site on the primary display 19 or the AR device 66. The non-sterile display 7, 9 can permit a non-sterile operator to perform a diagnostic step relevant to the surgical procedure, for example.

Figure 3:
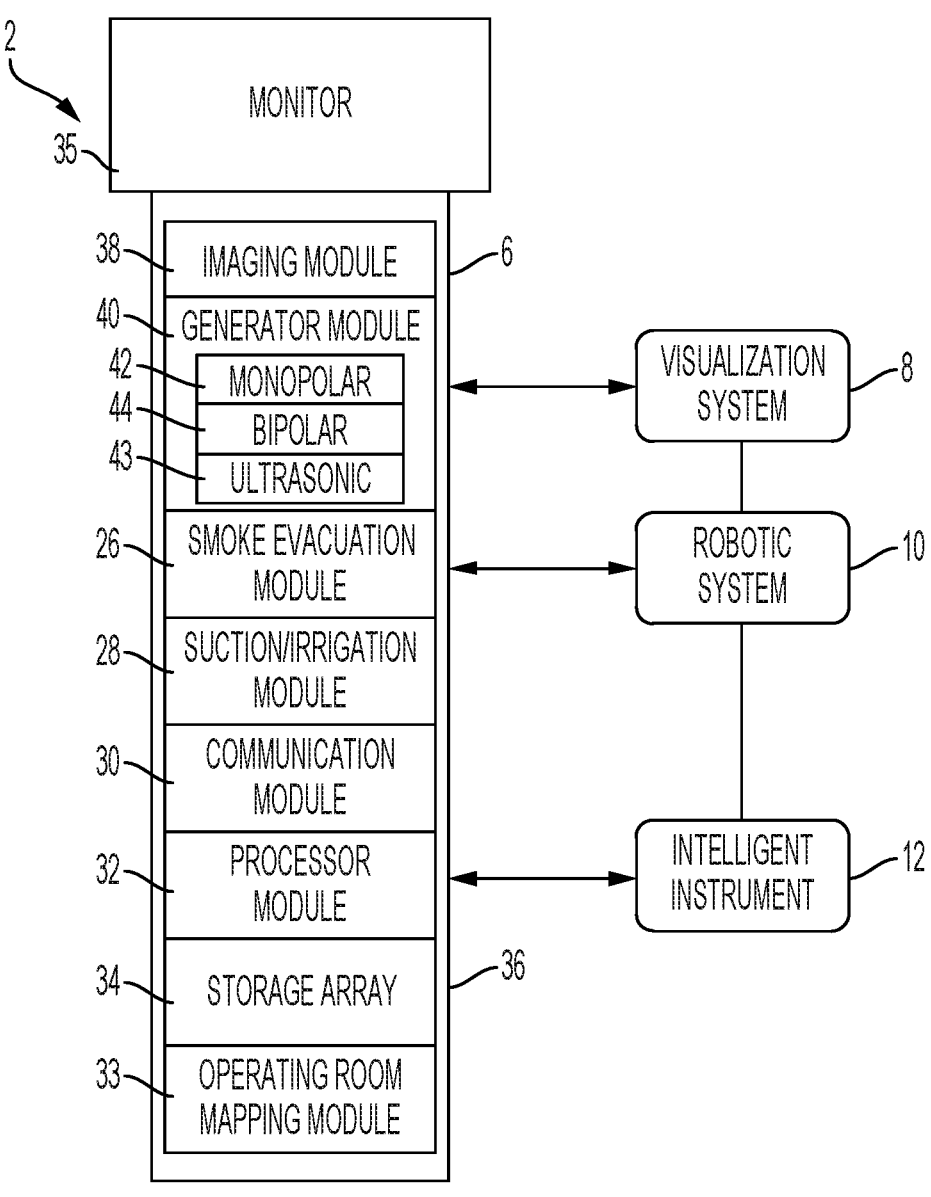
FIG. 3 is a surgical hub paired with a visualization system, a robotic system, and an intelligent instrument, according to one aspect of this disclosure.
Figure 10:
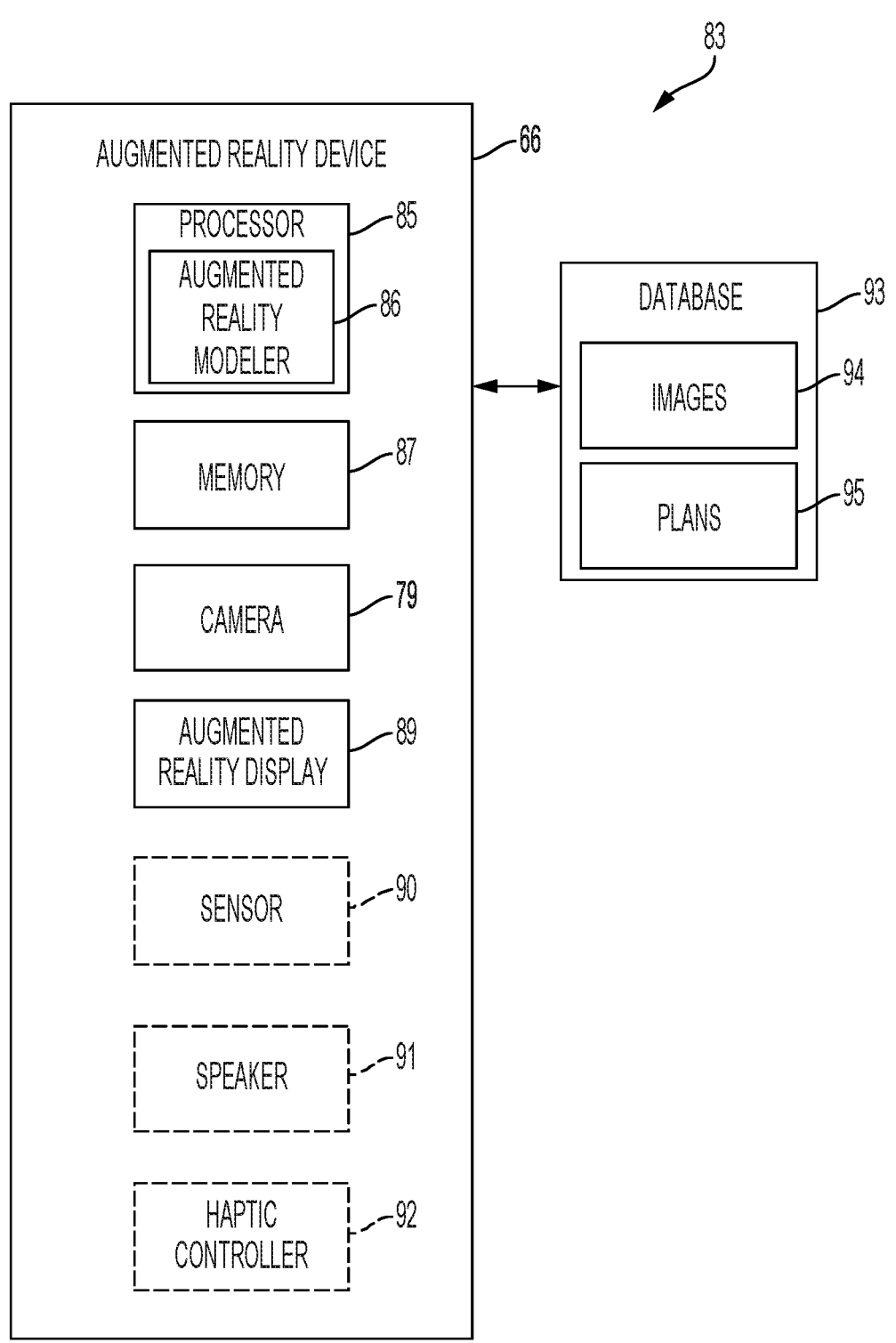
FIG. 10 illustrates a system for augmenting surgical instrument information using an augmented reality display, according to one aspect of this disclosure.

FIG. 3 depicts a hub 6 in communication with a visualization system 8, a robotic system 10, and a handheld intelligent surgical instrument 12. The hub 6 includes a hub display 35, an imaging module 38, a generator module 40, a communication module 30, a processor module 32, a storage array 34, and an operating room mapping module 33. The hub 6 further includes a smoke evacuation module 26 and/or a suction/irrigation module 28. In various aspects, the imaging module 38 comprises an AR device 66 and the processor module 32 comprises an integrated video processor and an augmented reality modeler (e.g., as shown in FIG. 10). A modular light source may be adapted for use with various imaging devices. In various examples, multiple imaging devices may be placed at different positions in the surgical field to provide multiple views (e.g., non-invasive, minimally invasive, invasive or open surgical procedures). The imaging module 38 can be configured to switch between the imaging devices to provide an optimal view. In various aspects, the imaging module 38 can be configured to integrate the images from the different imaging devices and provide an augmented reality interactive experience during a surgical procedure as described herein.

Figure 4:
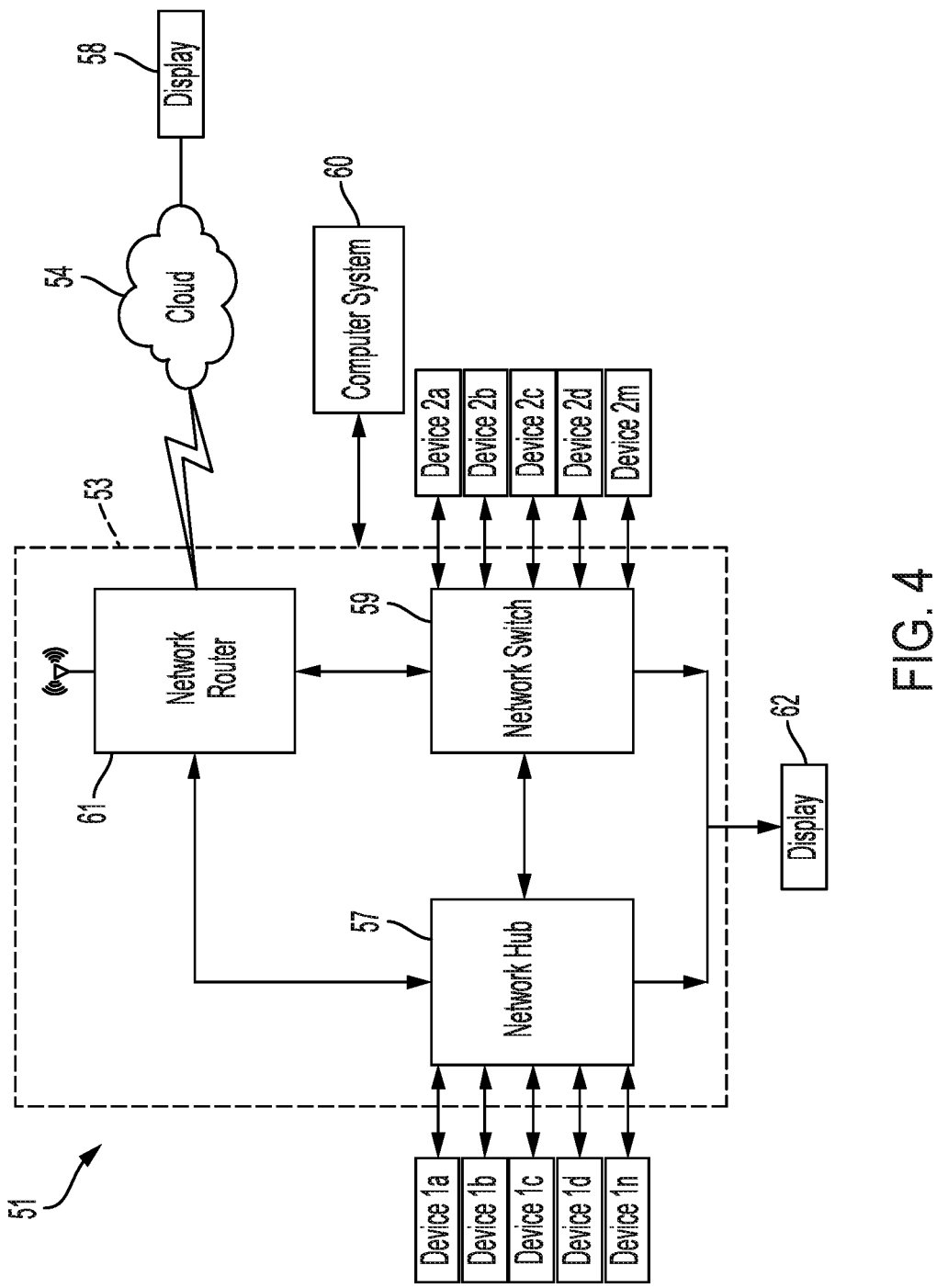
FIG. 4 illustrates a surgical data network comprising a modular communication hub configured to connect modular devices located in one or more operating theaters of a healthcare facility, or any room in a healthcare facility specially equipped for surgical operations, to the cloud, according to one aspect of this disclosure.

FIG. 4 shows a surgical data network 51 comprising a modular communication hub 53 configured to connect modular devices located in one or more operating theaters/rooms of a healthcare facility to a cloud-based system. The cloud 54 may include a remote server 63 (FIG. 5) coupled to a storage device 55. The modular communication hub 53 comprises a network hub 57 and/or a network switch 59 in communication with a network router 61. The modular communication hub 53 is coupled to a local computer system 60 to process data. Modular devices 1a-1n in the operating theater may be coupled to the modular communication hub 53. The network hub 57 and/or the network switch 59 may be coupled to a network router 61 to connect the devices 1a-1n to the cloud 54 or the local computer system 60. Data associated with the devices 1a-1n may be transferred to cloud-based computers via the router for remote data processing and manipulation. The operating theater devices 1a-1n may be connected to the modular communication hub 53 over a wired channel or a wireless channel. The surgical data network 51 environment may be employed to provide an augmented reality interactive experience during a surgical procedure as described herein and in particular providing augmented images if the surgical field to one or more than one remote display 58.

Figure 5:
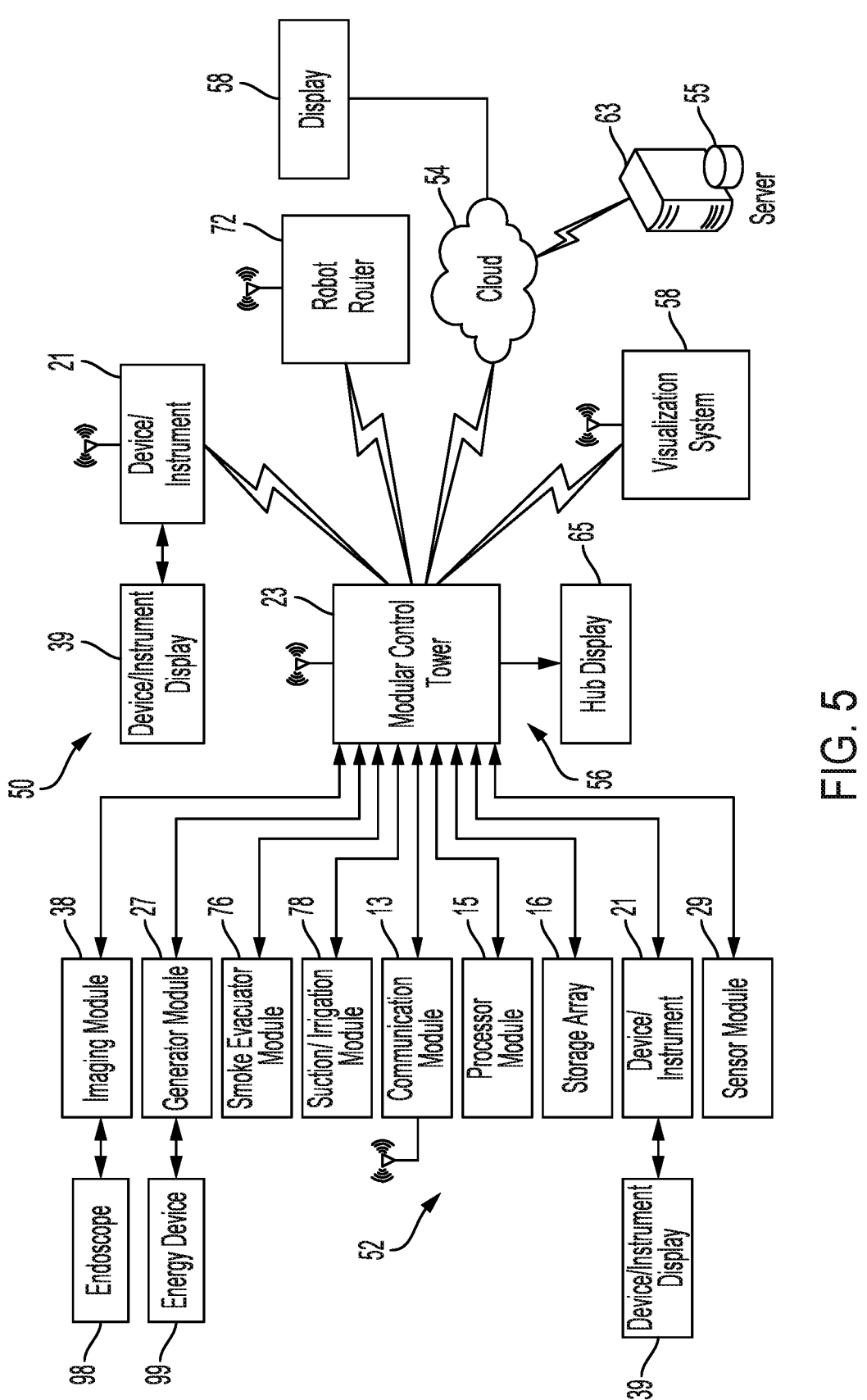
FIG. 5 illustrates a computer-implemented interactive surgical system, according to one aspect of this disclosure.
Figure 6:
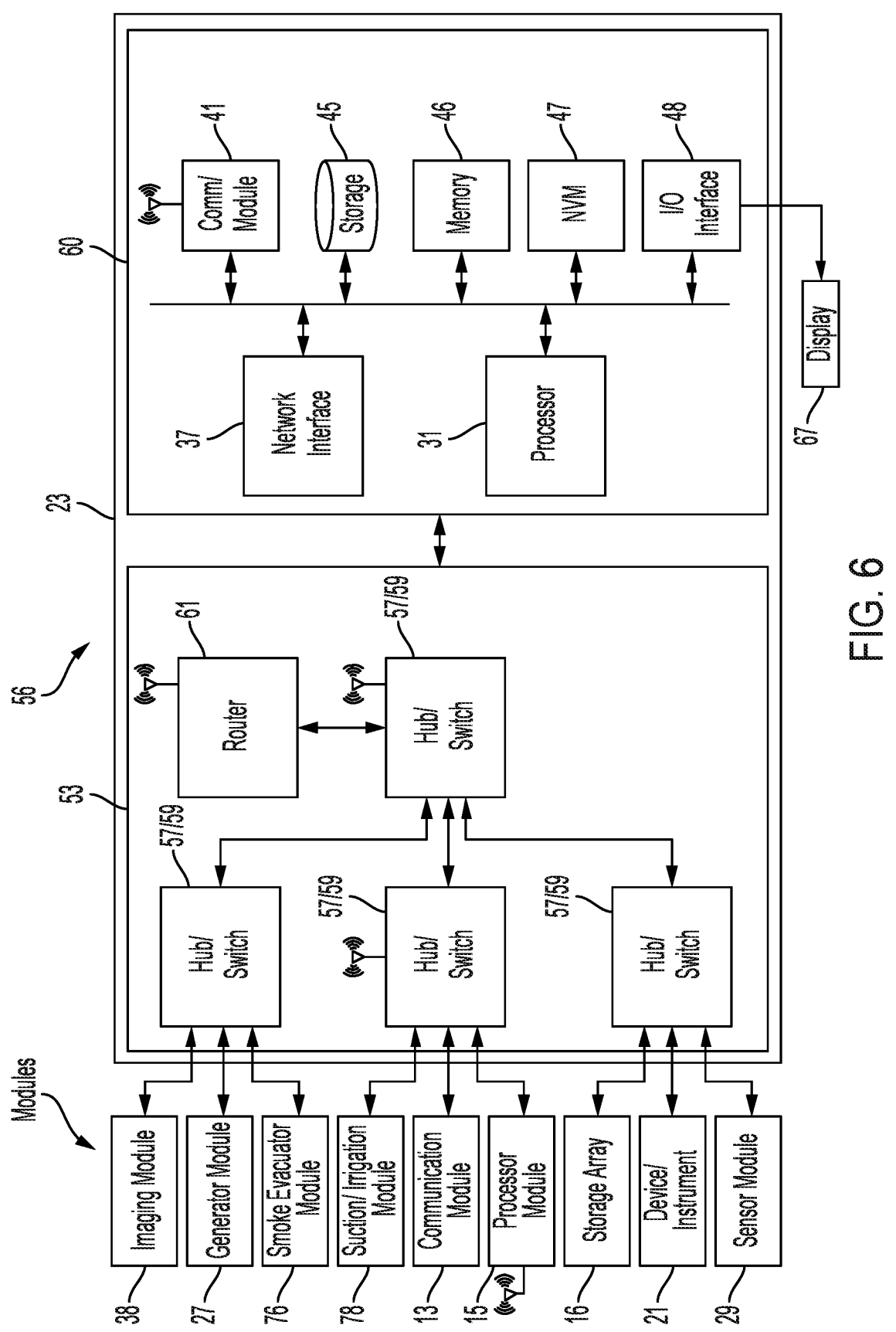
FIG. 6 illustrates a surgical hub comprising a plurality of modules coupled to the modular control tower, according to one aspect of this disclosure.

FIG. 5 illustrates a computer-implemented interactive surgical system 50. The computer-implemented interactive surgical system 50 is similar in many respects to the computer-implemented interactive surgical system 1. The computer-implemented interactive surgical system 50 includes one or more surgical systems 52, which are similar in many respects to the surgical systems 2. Each surgical system 52 includes at least one surgical hub 56 in communication with a cloud 54 that may include a remote server 63. In one aspect, the computer-implemented interactive surgical system 50 comprises a modular control tower 23 connected to multiple operating theater devices such as, for example, intelligent surgical instruments, robots, and other computerized devices located in the operating theater. As shown in FIG. 6, the modular control tower 23 comprises a modular communication hub 53 coupled to a computer system 60.

Back to FIG. 5, the modular control tower 23 is coupled to an imaging module 38 that is coupled to an endoscope 98, a generator module 27 that is coupled to an energy device 99, a smoke evacuator module 76, a suction/irrigation module 78, a communication module 13, a processor module 15, a storage array 16, a smart device/instrument 21 optionally coupled to a display 39, and a sensor module 29. The operating theater devices are coupled to cloud computing resources such as server 63, data storage 55, and displays 58 via the modular control tower 23. A robot hub 72 also may be connected to the modular control tower 23 and to the servers 63, data storage 55, and displays 58. The devices/instruments 21, visualization systems 58, among others, may be coupled to the modular control tower 23 via wired or wireless communication standards or protocols, as described herein. The modular control tower 23 may be coupled to a hub display 65 (e.g., monitor, screen) to display augmented images received comprising overlaid virtual objects on the real surgical field received from the imaging module 38, device/instrument display 39, and/or other visualization systems 58. The hub display 65 also may display data received from devices connected to the modular control tower 23 in conjunction with images and overlaid images.

FIG. 6 illustrates a surgical hub 56 comprising a plurality of modules coupled to the modular control tower 23. The modular control tower 23 comprises a modular communication hub 53, e.g., a network connectivity device, and a computer system 60 to provide local processing, visualization, and imaging of augmented surgical information, for example. The modular communication hub 53 may be connected in a tiered configuration to expand the number of modules (e.g., devices) that may be connected to the modular communication hub 53 and transfer data associated with the modules to the computer system 60, cloud computing resources, or both. Each of the network hubs/switches 57, 59 in the modular communication hub 53 may include three downstream ports and one upstream port. The upstream network hub/switch 57, 59 is connected to a processor 31 to provide a communication connection to the cloud computing resources and a local display 67. Communication to the cloud 54 may be made either through a wired or a wireless communication channel.

The computer system 60 comprises a processor 31 and a network interface 37. The processor 31 is coupled to a communication module 41, storage 45, memory 46, non-volatile memory 47, and input/output interface 48 via a system bus. The system bus can be any of several types of bus structure(s) including the memory bus or memory controller, a peripheral bus or external bus, and/or a local bus using any variety of available bus architectures.

The processor 31 comprises an augmented reality modeler (e.g., as shown in FIG. 10) and may be implemented as a single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital convert-ers (ADCs) with 12 analog input channels, details of which are available for the product datasheet.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes ran-dom-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SL-DRAM), and direct Rambus RAM (DRRAM).

The computer system 60 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

In various aspects, the computer system 60 of FIG. 6, the imaging module 38 and/or visualization system 58, and/or the processor module 15 of FIGS. 4-6, may comprise an image processor, image-processing engine, graphics pro-cessing unit (GPU), media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor archi-tecture.

Figure 7:
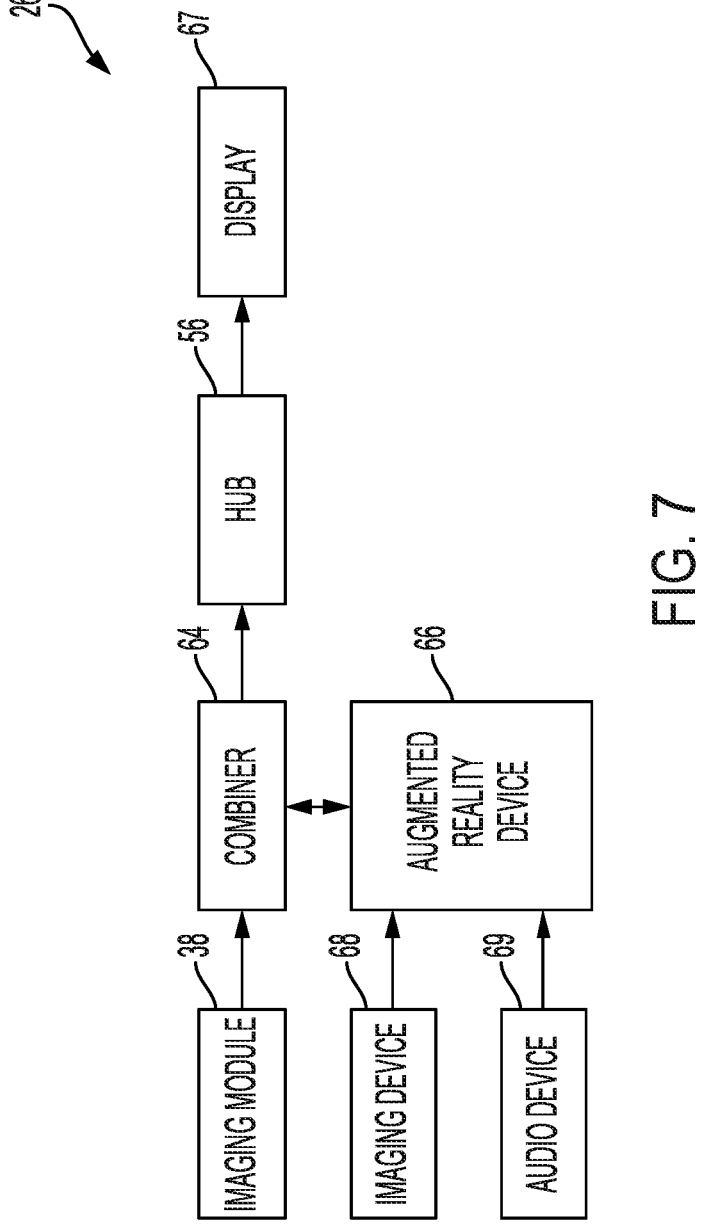
FIG. 7 illustrates an augmented reality (AR) system comprising an intermediate signal combiner positioned in the communication path between an imaging module and a surgical hub display, according to one aspect of this disclosure.

FIG. 7 illustrates an augmented reality system 263 com-prising an intermediate signal combiner 64 positioned in the communication path between an imaging module 38 and a surgical hub display 67. The signal combiner 64 combines audio and/or image data received from an imaging module 38 and/or an AR device 66. The surgical hub 56 receives the combined data from the combiner 64 and overlays the data provided to the display 67, where the overlaid data is displayed. The imaging device 68 may be a digital video camera and the audio device 69 may be a microphone. The signal combiner 64 may comprise a wireless heads-up display adapter to couple to the AR device 66 placed into the communication path of the display 67 to a console allowing the surgical hub 56 to overlay data on the display 67.

Figure 8:
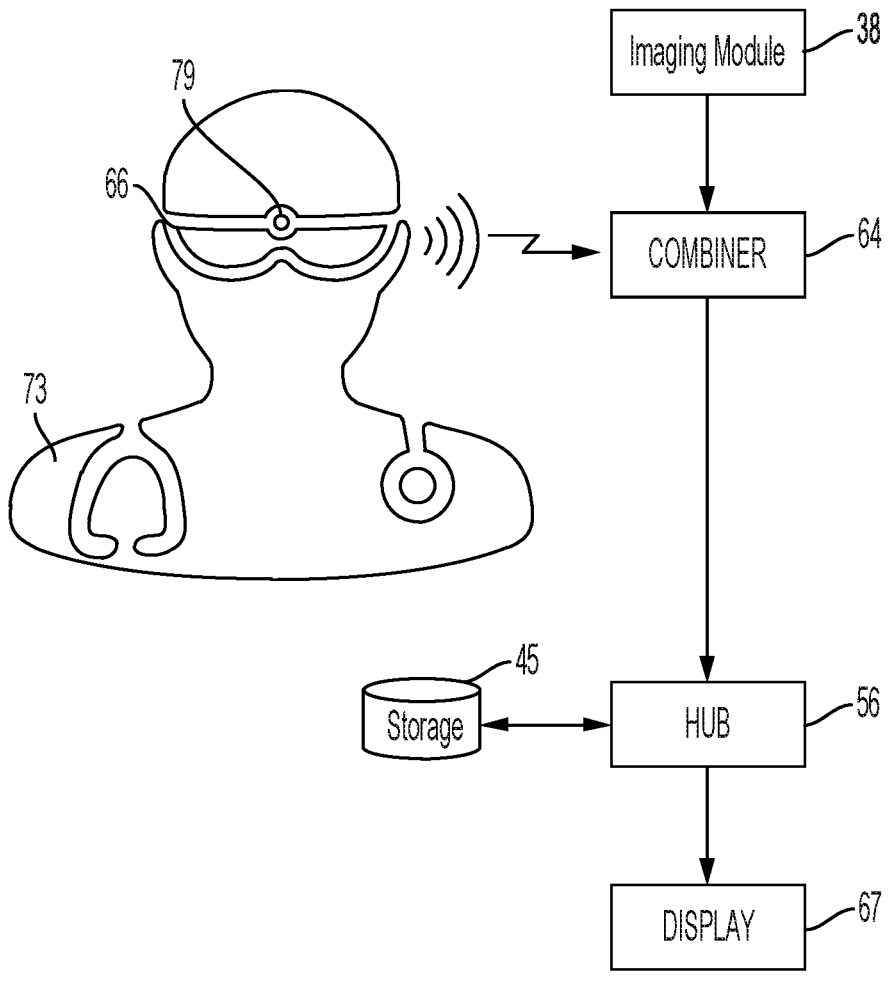
FIG. 8 illustrates an augmented reality (AR) system comprising an intermediate signal combiner positioned in the communication path between an imaging module and a surgical hub display, according to one aspect of this disclosure.

FIG. 8 illustrates an augmented reality (AR) system comprising an intermediate signal combiner positioned in the communication path between an imaging module and a surgical hub display. FIG. 8 illustrates an AR device 66 worn by a surgeon 73 to communicate data to the surgical hub 56. Peripheral information of the AR device 66 does not include active video. Rather, the peripheral information includes only device settings, or signals that do not have same demands of refresh rates. Interaction may augment the surgeon's 73 information based on linkage with preoperative computerized tomography (CT) or other data linked in the surgical hub 56. The AR device 66 can identify structure—ask whether instrument is touching a nerve, vessel, or adhesion, for example. The AR device 66 may include pre-operative scan data, an optical view, tissue interrogation properties acquired throughout procedure, and/or processing in the surgical hub 56 used to provide an answer. The surgeon 73 can dictate notes to the AR device 66 to be saved with patient data in the hub storage 45 for later use in report or in follow up.

The AR device 66 worn by the surgeon 73 links to the surgical hub 56 with audio and visual information to avoid the need for overlays, and allows customization of displayed information around periphery of view. The AR device 66 provides signals from devices (e.g., instruments), answers queries about device settings, or positional information linked with video to identify quadrant or position. The AR device 66 has audio control and audio feedback from the AR device 66. The AR device 66 is able to interact with other systems in the operating theater and have feedback and interaction available wherever the surgeon 73 is viewing. For example, the AR device 66 may receive voice or gesture initiated commands and queries from a surgeon, and the AR device 66 may provide feedback in the form of one or more modalities including audio, visual, or haptic touch.

Figure 9:
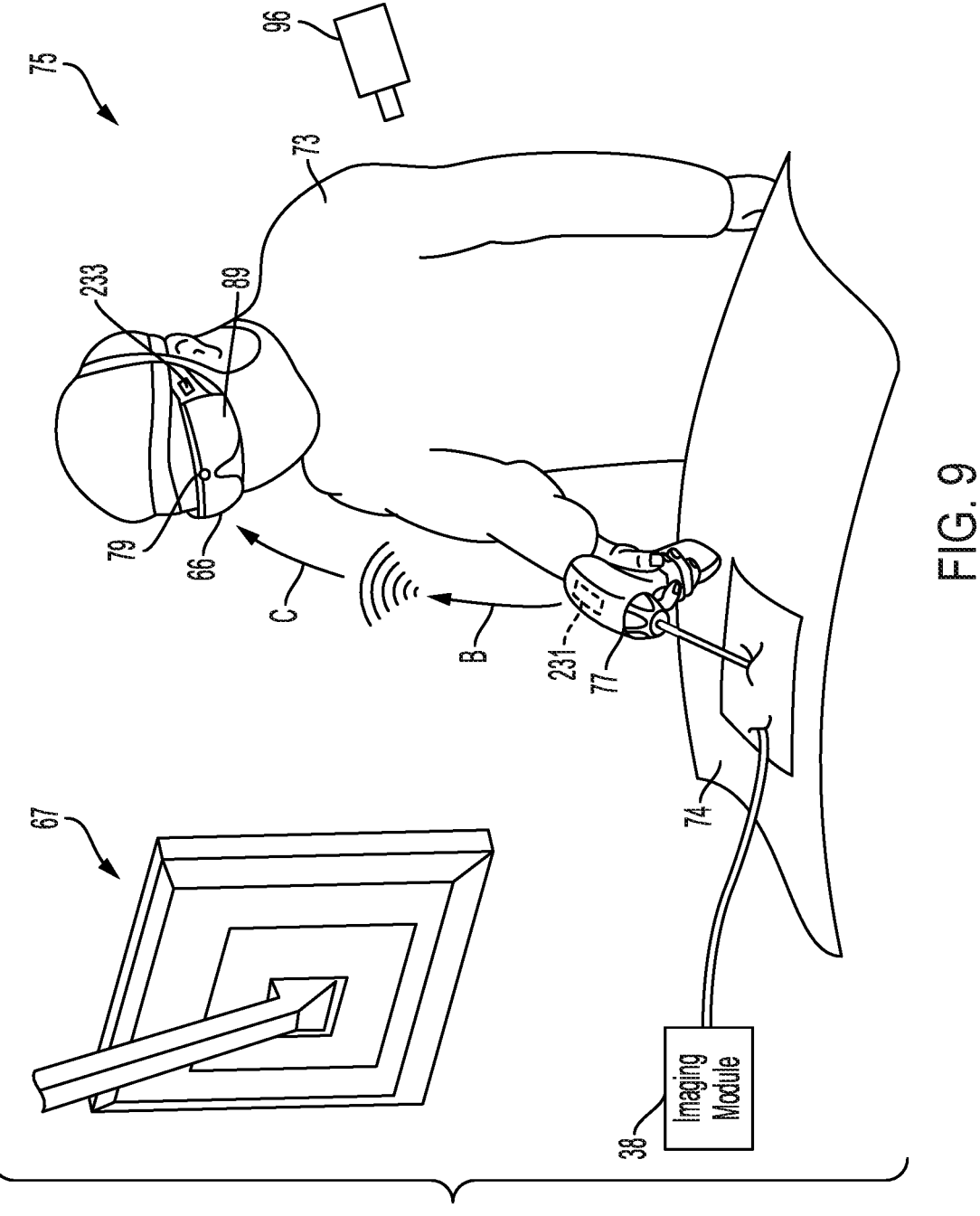
FIG. 9 illustrates an augmented reality (AR) device worn by a surgeon to communicate data to the surgical hub, according to one aspect of this disclosure.

FIG. 9 illustrates a surgeon 73 wearing an AR device 66, a patient 74, and may include a camera 96 in an operating room 75. The AR device 66 worn by the surgeon 73 may be used to present to the surgeon 73 a virtual object overlaid on a real time image of the surgical field through augmented reality display 89 or through the hub connected display 67. The real time image may include a portion of a surgical instrument 77. The virtual object may not be visible to others within the operating room 75 (e.g., surgical assistant or nurse), though they also may wear AR devices 66. Even if another person is viewing the operating room 75 with an AR device 66, the person may not be able to see the virtual object or may be able to see the virtual object in a shared augmented reality with the surgeon 73, or may be able to see a modified version of the virtual object (e.g., according to customizations unique to the surgeon 73) or may see dif-ferent virtual objects.

A virtual object and/or data may be configured to appear on a portion of a surgical instrument 77 or in a surgical field of view captured by an imaging module 38, an imaging device 68 during minimally invasive surgical procedures, and/or the camera 96 during open surgical procedures. In the illustrated example, the imaging module 38 is a laparoscopic camera that provides a live feed of a surgical area during a minimally invasive surgical procedure. An AR system may present virtual objects that are fixed to a real object without regard to a perspective of a viewer or viewers of the AR system (e.g., the surgeon 73). For example, a virtual object may be visible to a viewer of the AR system inside the operating room 75 and not visible to a viewer of the AR system outside the operating room 75. The virtual object may be displayed to the viewer outside the operating room 75 when the viewer enters the operating room 75. The augmented image may be displayed on the surgical hub display 67 or the augmented reality display 89.

The AR device 66 may include one or more screens or lens, such as a single screen or two screens (e.g., one per eye of a user). The screens may allow light to pass through the screens such that aspects of the real environment are visible while displaying the virtual object. The virtual object may be made visible to the surgeon 73 by projecting light. A virtual object may appear to have a degree of transparency or may be opaque (i.e., blocking aspects of the real environment).

An AR system may be viewable to one or more viewers, and may include differences among views available for the one or more viewers while retaining some aspects as universal among the views. For example, a heads-up display may change between two views while virtual objects and/or data may be fixed to a real object or area in both views. Aspects such as a color of an object, lighting, or other changes may be made among the views without changing a fixed position of at least one virtual object.

A user may see a virtual object and/or data presented in an AR system as opaque or as including some level of transparency. In an example, the user may interact with the virtual object, such as by moving the virtual object from a first position to a second position. For example, the user may move an object with his or her hand. This may be done in the AR system virtually by determining that the hand has moved into a position coincident or adjacent to the object (e.g., using one or more cameras, which may be mounted on the AR device 66, such as AR device camera 79 or separate 96, and which may be static or may be controlled to move), and causing the object to move in response. Virtual aspects may include virtual representations of real world objects or may include visual effects, such as lighting effects, etc. The AR system may include rules to govern the behavior of virtual objects, such as subjecting a virtual object to gravity or friction, or may include other predefined rules that defy real world physical constraints (e.g., floating objects, perpetual motion, etc.). The AR device 66 may include a camera 79 on the AR device 66 (not to be confused with the camera 96, separate from the AR device 66). The AR device camera 79 or the camera 96 may include an infrared camera, an infrared filter, a visible light filter, a plurality of cameras, a depth camera, etc. The AR device 66 may project virtual items over a representation of a real environment, which may be viewed by a user.

The AR device 66 may be used in the operating room 75 during a surgical procedure, for example performed by the surgeon 73 on the patient 74. The AR device 66 may project or display virtual objects, such as a virtual object during the surgical procedure to augment the surgeon's vision. The surgeon 73 may view a virtual object using the AR device 66, a remote controller for the AR device 66, or may interact with a virtual object, for example, using a hand to "interact" with a virtual object or a gesture recognized by the camera 79 of the AR device 66. A virtual object may augment a surgical tool such as the surgical instrument 77. For example, the virtual object may appear (to the surgeon 73 viewing the virtual object through the AR device 66) to be coupled with or remain a fixed distance from the surgical instrument 77. In another example, the virtual object may be used to guide the surgical instrument 77, and may appear to be fixed to the patient 74. In certain examples, a virtual object may react to movements of other virtual or real-world objects in the surgical field. For example, the virtual object may be altered when a surgeon is manipulating a surgical instrument in proximity to the virtual object.

The augmented reality display system imaging device 38 capture a real image of a surgical area during a surgical procedure. An augmented reality display 89, 67 presents an overlay of an operational aspect of the surgical instrument 77 onto the real image of the surgical area. The surgical instrument 77 includes communications circuitry 231 to communicate operational aspects and functional data from the surgical instrument 77 to the AR device 66 via communication communications circuitry 233 on the AR device 66.

Although the surgical instrument 77 and the AR device 66 are shown in RF wireless communication between circuits 231, 233 as indicated by arrows B, C, other communication techniques may employed (e.g., wired, ultrasonic, infrared, etc.). The overlay is related to the operational aspect of the surgical instrument 77 being actively visualized. The overlay combines aspects of tissue interaction in the surgical area with functional data from the surgical instrument 77. A processor portion of the AR device 66 is configured to receive the operational aspects and functional data from the surgical instrument 77, determine the overlay related to the operation of the surgical instrument 77, and combine the aspect of the tissue in the surgical area with the functional data from the surgical instrument 77. The augmented images indicate alerts relative to device performance considerations, alerts of incompatible usage, alerts on incomplete capture. Incompatible usage includes tissue out range conditions and tissue incorrectly balanced within the jaws of the end effector. Additional augmented images provide an indication of collateral events including indication of tissue tension and indication of foreign object detection. Other augmented images indicate device status overlays and instrument indication.

FIG. 10 illustrates a system 83 for augmenting images of a surgical field with information using an AR display 89, in accordance with at least one aspect of this disclosure. The system 83 may be used to perform the techniques described hereinbelow, for example, by using the processor 85. The system 83 includes one aspect of an AR device 66 that may be in communication with a database 93. The AR device 66 includes a processor 85, memory 87, an AR display 89, and a camera 79. The AR device 66 may include a sensor 90, a speaker 91, and/or a haptic controller 92. The database 93 may include image storage 94 or preoperative plan storage 95.

The processor 85 of the AR device 66 includes an augmented reality modeler 86. The augmented reality modeler 86 may be used by the processor 85 to create the augmented reality environment. For example, the augmented reality modeler 86 may receive images of the instrument in a surgical field, such as from the camera 79 or sensor 90, and create the augmented reality environment to fit within a display image of the surgical field of view. In another example, physical objects and/or date may be overlaid on the surgical field of view and/or the surgical instruments images and the augmented reality modeler 86 may use physical objects and data to present the augmented reality display of virtual object s and/or data in the augmented reality environment. For example, the augmented reality modeler 86 may use or detect an instrument at a surgical site of the patient and present a virtual object and/or data on the surgical instrument and/or an image of the surgical site in the surgical field of view captured by the camera 79. The AR display 89 may display the AR environment overlaid on a real environment. The display 89 may show a virtual object and/or data, using the AR device 66, such as in a fixed position in the AR environment.

The AR device 66 may include a sensor 90, such as an infrared sensor. The camera 79 or the sensor 90 may be used to detect movement, such as a gesture by a surgeon or other user, that may be interpreted by the processor 85 as attempted or intended interaction by the user with the virtual target. The processor 85 may identify an object in a real environment, such as through processing information received using the camera 79. In other aspects, the sensor 90 may be a tactile, audible, chemical, or thermal sensor to generate corresponding signals that may combined with various data feeds to create the augmented environment. The sensor 90 may include binaural audio sensors (spatial sound), inertial measurement (accelerometer, gyroscope, magnetometer) sensors, environmental sensors, depth camera sensors, hand and eye tracking sensors, and voice command recognition functions.

The AR display 89, for example during a surgical procedure, may present, such as within a surgical field while permitting the surgical field to be viewed through the AR display 89, a virtual feature corresponding to a physical feature hidden by an anatomical aspect of a patient. The virtual feature may have a virtual position or orientation corresponding to a first physical position or orientation of the physical feature. In an example, the virtual position or orientation of the virtual feature may include an offset from the first physical position or orientation of the physical feature. The offset may include a predetermined distance from the augmented reality display, a relative distance from the augmented reality display to the anatomical aspect, or the like.

In one example, the AR device 66 may be an individual AR device. In one aspect, the AR device 66 may be a HoloLens 2 AR device manufactured by Microsoft of Redmond, Wash. This AR device 66 includes a visor with lenses and binaural audio features (spatial sound), inertial measurement (accelerometer, gyroscope, magnetometer), environmental sensors, depth camera, and video camera, hand and eye tracking, and voice command recognition functions. It provides an improved field of view with high resolution by using mirrors to direct waveguides in front of wearer's eyes. Images can be enlarged by changing angles of mirrors. It also provides eye tracking to recognize users and adjust lens widths for specific users.

In another example, the AR device 66 may be a Snapchat Spectacles 3 AR device. This AR device provides the ability to capture paired images and recreate 3D depth mapping, add in virtual effects, and replay 3D videos. The AR device includes two HD cameras to capture 3D photos and videos at 60 fps—while four built-in microphones record immersive, high-fidelity audio. Images from both cameras combine to build out a geometric map of the real world around the user to provide a new sense of depth perception. Photos and videos may be wirelessly synchronized to external display devices.

In yet another example, the AR device 66 may be a Glass 2 AR device by Google. This AR device provides inertial measurement (accelerometer, gyroscope, magnetometer) information overlaid on lens (out of view) to supplement information.

In another example, the AR device 66 may be an Echo Frames AR device by Amazon. This AR device does not have cameras/displays. A microphone and speaker are linked to Alexa. This AR device provides less functionality than a heads-up display.

In yet another example, the AR device 66 may be a Focals AR device by North (Google). This AR device provides notification pusher/smartwatch analog; inertial measurement, screen overlay of information (weather, calendar, messages), voice control (Alexa) integration. This AR device provides basic heads-up display functionality.

In another example, the AR device 66 may be an Nreal AR device. This AR device includes spatial sound, two environmental cameras, a photo camera, IMU (accelerometer, gyroscope), ambient light sensor, proximity sensor functionality. A nebula projects application information on lenses. In various other examples, the AR device 66 may be any one of the following commercially available AR devices:

Magic Leap 1, Epson Moverio, Vuzix Blade AR, ZenFone AR, Microsoft AR glasses prototype, EyeTap to create collinear light to that of the environment directly into the retina. A beam splitter makes the same light seen by the eye available to the computer to process and overlay information, for example. AR visualization systems include HUD, contact lenses, glasses, virtual reality (VR) headsets, virtual retinal display, on in operating room displays, and/or smart contact lenses (bionic lenses).

Multi-user interfaces for the AR device 66 include virtual retinal displays such as raster displays drawn directly on retinas instead of on a screen in front of the eye, smart televisions, smart phones, and/or spatial displays such as Sony spatial display systems.

Other AR technology may include, for example, AR capture devices and software applications, AR creation devices and software applications, and AR cloud devices and software applications. AR capture devices and software applications include, for example, Apple Polycam app, Ubiquity 6 (Mirrorworld using Display.land app)—users can scan and get 3d image of real world (to create 3D model). AR creation devices and software applications include, for example, Adobe Aero, Vuforia, ARToolKit, Google ARCore, Apple ARKit, MAXST, Aurasma, Zappar, Blippar. AR cloud devices and software applications include, for example, Facebook, Google (world geometry, objection recognition, predictive data), Amazon AR Cloud (commerce), Microsoft Azure, Samsung Project Whare, Niantic, Magic Leap.

One aspect of the following disclosure describes various overlays of surgical instrument operational aspects or functions onto a live video stream of a surgical area as visualized through a laparoscopic camera surgical field of view during a minimally invasive surgical procedure. The overlay is related to the operation of one of the surgical instruments or devices being actively visualized. The overlays combine aspects of tissue/organ interaction with functional data received from surgical instruments used in the surgical procedure. Surgical instruments may include graspers, clamps, staplers, ultrasonic, RF, or combination of each of these instruments. In regard to graspers and clamps, aspects of tissue parameters may include incomplete capture of the tissue along with the status of the clamp or magnitude of the clamp. In regard to a surgical stapler, aspects of tissue parameters may include tissue capture location, tissue compression, clamping, or firing sufficiency of a surgical stapler. In regard to advanced energy devices, such ultrasonic or RF devices, aspects of tissue parameters may include impedance, cautery status, bleeding magnitude, and aspects of instrument function may include energy level, timing, clamp pressure, among others, for examples. The augmented images shown in FIGS. 11-35 hereinbelow may be viewed on a local display, a remote display, and/or an AR device as described hereinabove in connection with FIGS. 1-10. Although the augmented images are described as being visualized through a laparoscopic camera during a minimally invasive surgical procedure, the images may be captured during non-invasive and invasive (e.g., open) surgical procedures without limiting the scope of this disclosure in this context. These aspects are described hereinbelow.

Figure 11:
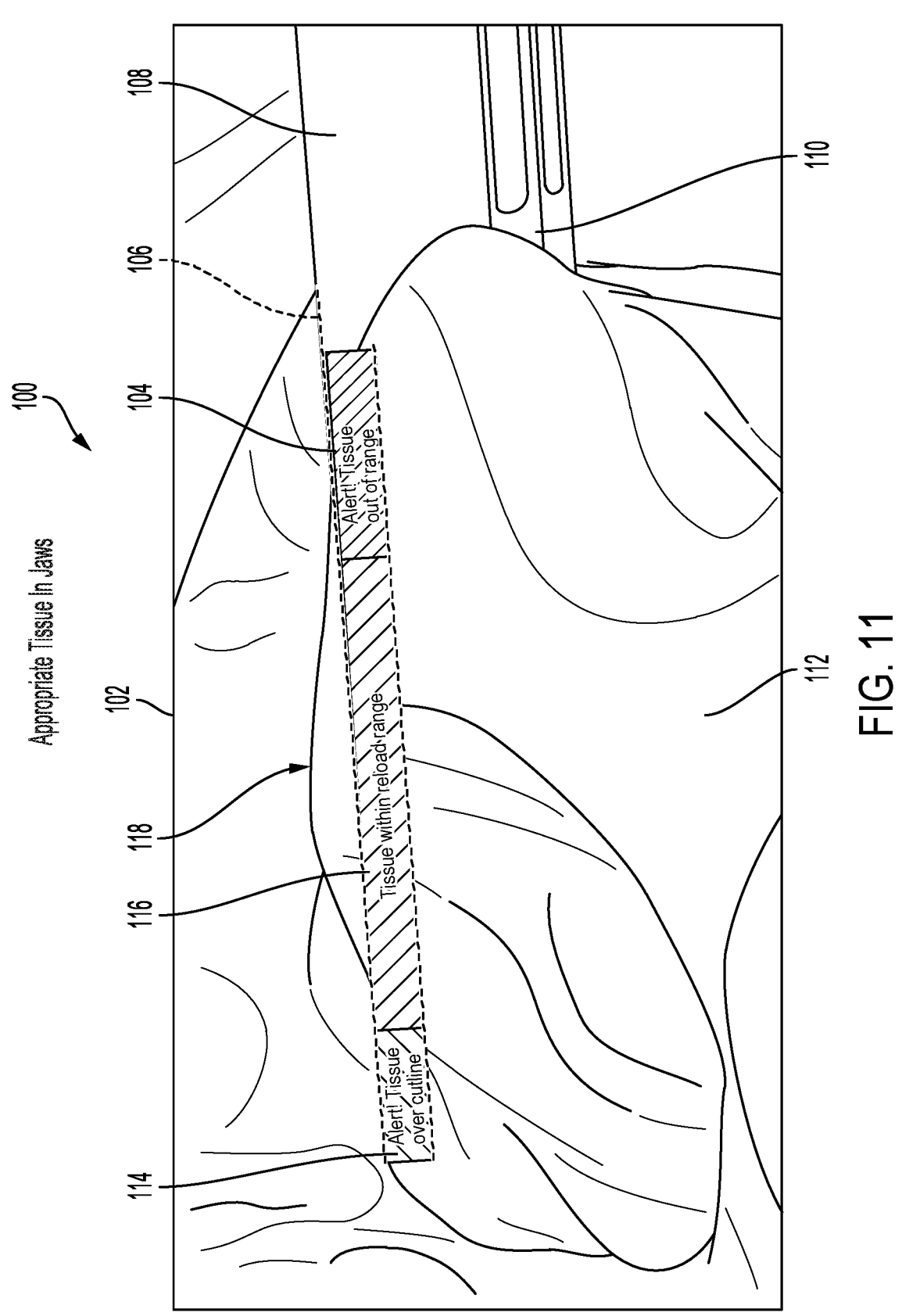
FIG. 11 is an augmented image of a live feed of a surgical area visualized through a laparoscopic camera during a minimally invasive surgical procedure indicating appropriate tissue captured between jaws of a surgical instrument end effector as a tissue aspect, according to one aspect of this disclosure.
Figure 75:
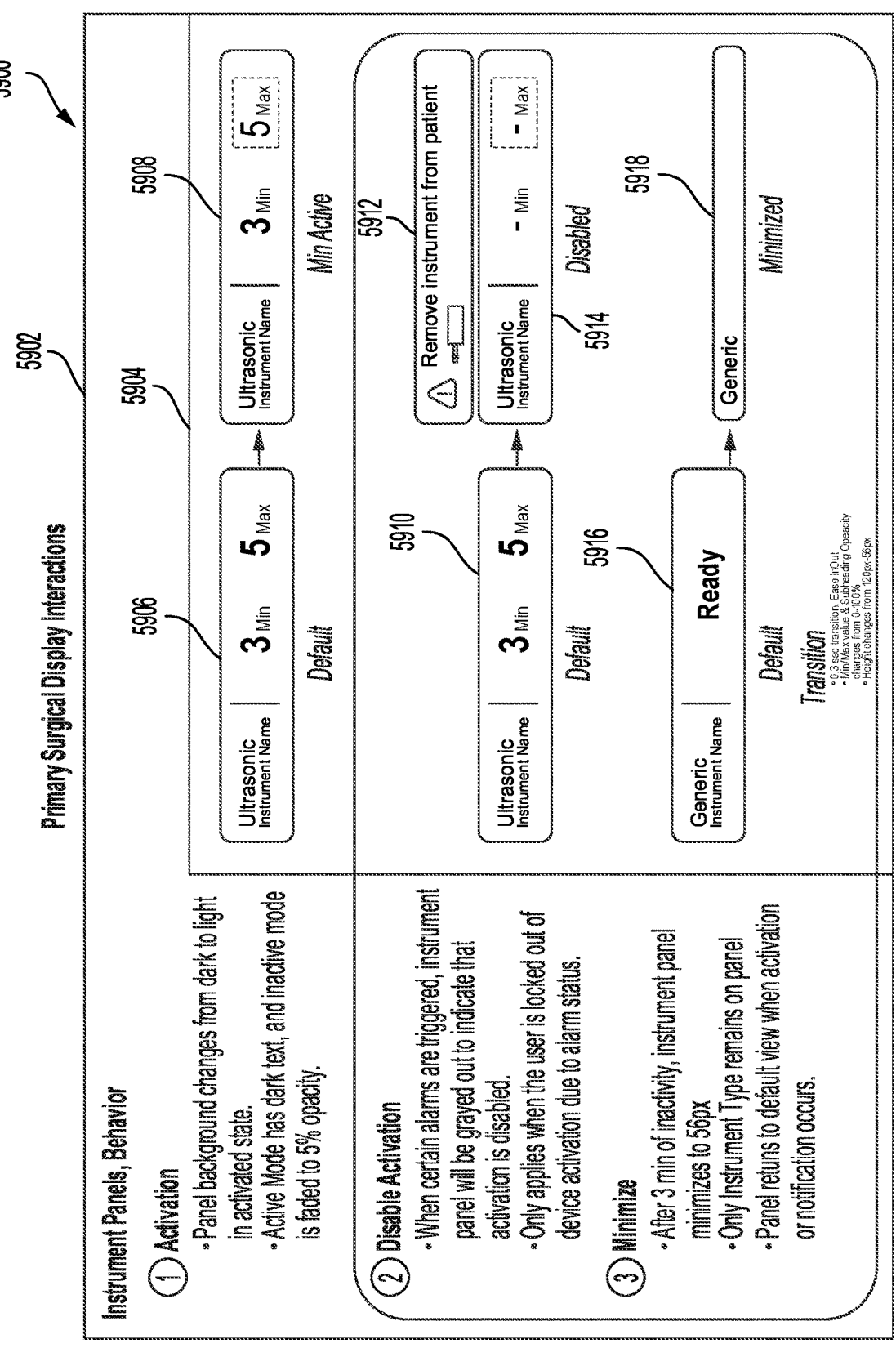
FIG. 75 is an image of a primary surgical display inter-actions screen displaying primary surgical display interac-tions, according to one aspect of this disclosure.

FIGS. 11-75 describe various augmented images visualized through a laparoscopic camera during a minimally invasive surgical procedure. An augmented reality display system is used during a surgical procedure. The augmented reality display system comprises an imaging device to capture a real image of a surgical area during the surgical procedure, an augmented reality display to present an overlay of an operational aspect of a surgical instrument onto the real image of the surgical area, and a processor. The overlay is related to the operational aspect of the surgical instrument being actively visualized. The overlay combines aspects of tissue interaction in the surgical area with functional data from the surgical instrument. The processor is configured to receive the functional data for the surgical instrument, determine the overlay related to the operation of the surgical instrument, and combine the aspect of the tissue in the surgical area with the functional data from the surgical instrument. The augmented images indicate alerts relative to device performance considerations, alerts of incompatible usage, alerts on incomplete capture. Incompatible usage includes tissue out range conditions and tissue incorrectly balanced within the jaws of the end effector. Additional augmented images provide an indication of collateral events including indication of tissue tension and indication of foreign object detection. Other augmented images indicate device status overlays and instrument indication.

FIGS. 11-75 also describe functional overlays of instrument critical operations or parameters to clearly represent the surgical stapler, energy device, or aspects of its interaction. In one aspect, the overlaid data is adjusted by an aspect detected by the surgical hub to modify the overlay from the information merely detected by the source instrument to add context. In another aspect, the displays may be adjusted or modified by the user and as a result also result in modifications of the surgical instrument being monitored operation.

FIG. 11 is an augmented image 100 of a live feed of a surgical area 118 as visualized through a laparoscopic camera during a minimally invasive surgical procedure indicating appropriate tissue 112 captured between jaws 110 of a surgical instrument end effector 108. The operational aspect of the surgical instrument is clamping the tissue 112 between the jaws 110 of the end effector 108. The aspect of the tissue 112 is appropriate capture of the tissue 112 between the jaws 110 of the end effector 108. The laparoscopic field of view 102 of the surgical area 118 shows a surgical instrument end effector 108 grasping tissue 112 in its jaws 110. The augmented image 100 shows a virtual graphical alert overlay 106 superimposed on the anvil 110 of the end effector 108. The virtual superimposed graphical alert overlay 106 indicates the amount of tissue grasped in the end effector 108 jaws 110 to inform the OR team of staple cartridge reload selection for stapling, overloading tissue for energy, etc. A first superimposed alert 104 informs that the tissue 112 grasped with the jaws 110 at the proximal end of the end effector 108 is out of range. A second superimposed alert 116 informs that the tissue 112 grasped with the jaws 110 at the medial portion of the end effector 108 is within reload range. A third superimposed alert 114 informs that the tissue 112 grasped with the jaws at the distal end of the end effector 108 is over the cut line. The superimposed graphical alert overlay 106 apply to energy based surgical instruments, surgical stapler instruments, manipulation tools, and the like.

Figure 12:
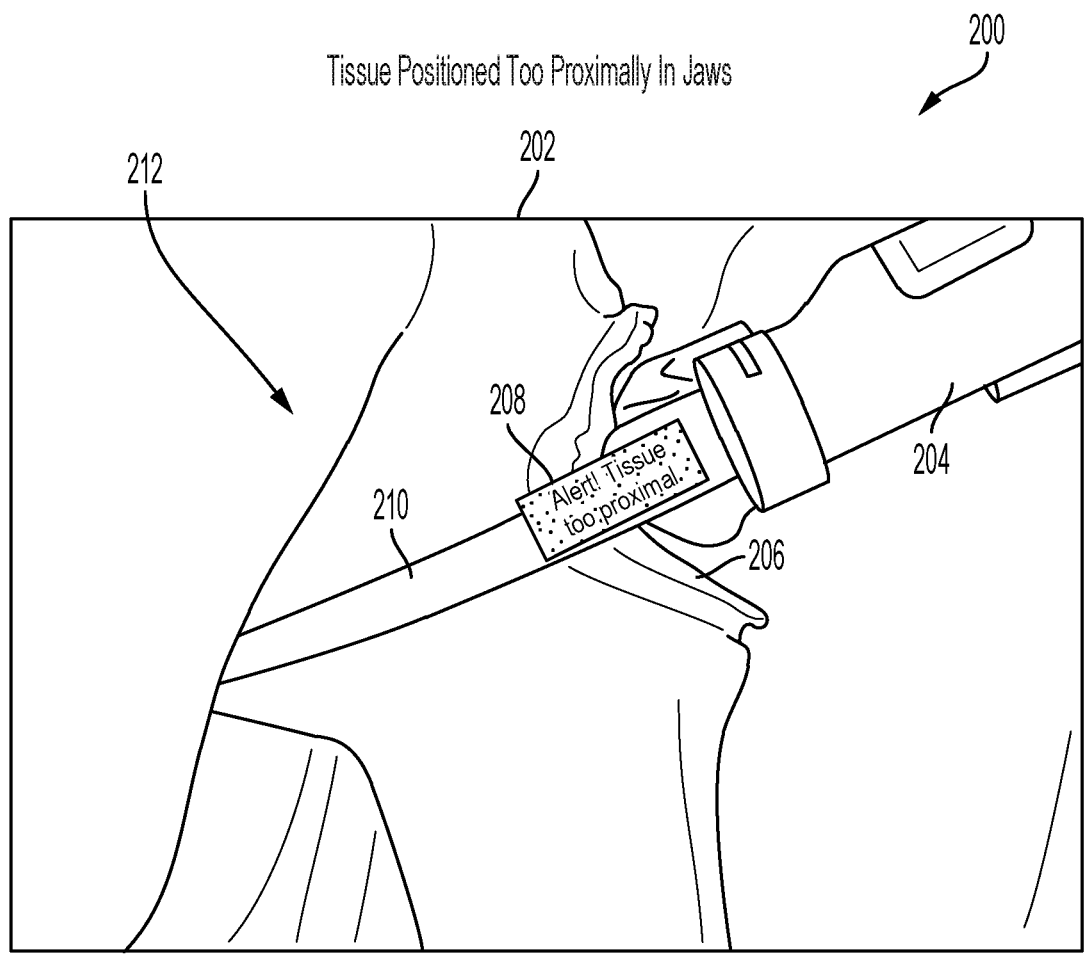
FIG. 12 is an augmented image of a live feed of a surgical area visualized through a laparoscopic camera during a minimally invasive surgical procedure indicating tissue position proximally captured between of a surgical instrument end effector as a tissue aspect, according to one aspect of this disclosure.

FIG. 12 is an augmented image 200 of a live feed of a surgical area 212 as visualized through a laparoscopic camera during a minimally invasive surgical procedure indicating tissue 206 position proximally captured between jaws 210 of a surgical instrument end effector 204 as a tissue aspect. Aspects of the tissue include incorrectly captured or positioned tissue 206 between the jaws 210 of the end effector 204. The laparoscopic field of view 202 of the surgical area 212 shows the surgical instrument end effector 204 grasping tissue 206 between the jaws 210 of the end effector 204. The augmented image 200 shows a graphical alert overlay 208 superimposed on one of the jaws 210 of the end effector 204 to indicate that the tissue 206 is grasped excessively proximally 206 with the jaws 210 of the end effector 204. Although the superimposed alert 208 applies primarily to energy based surgical instruments, for example, similar alerts may be superimposed in surgical stapler instruments.

Figure 13:
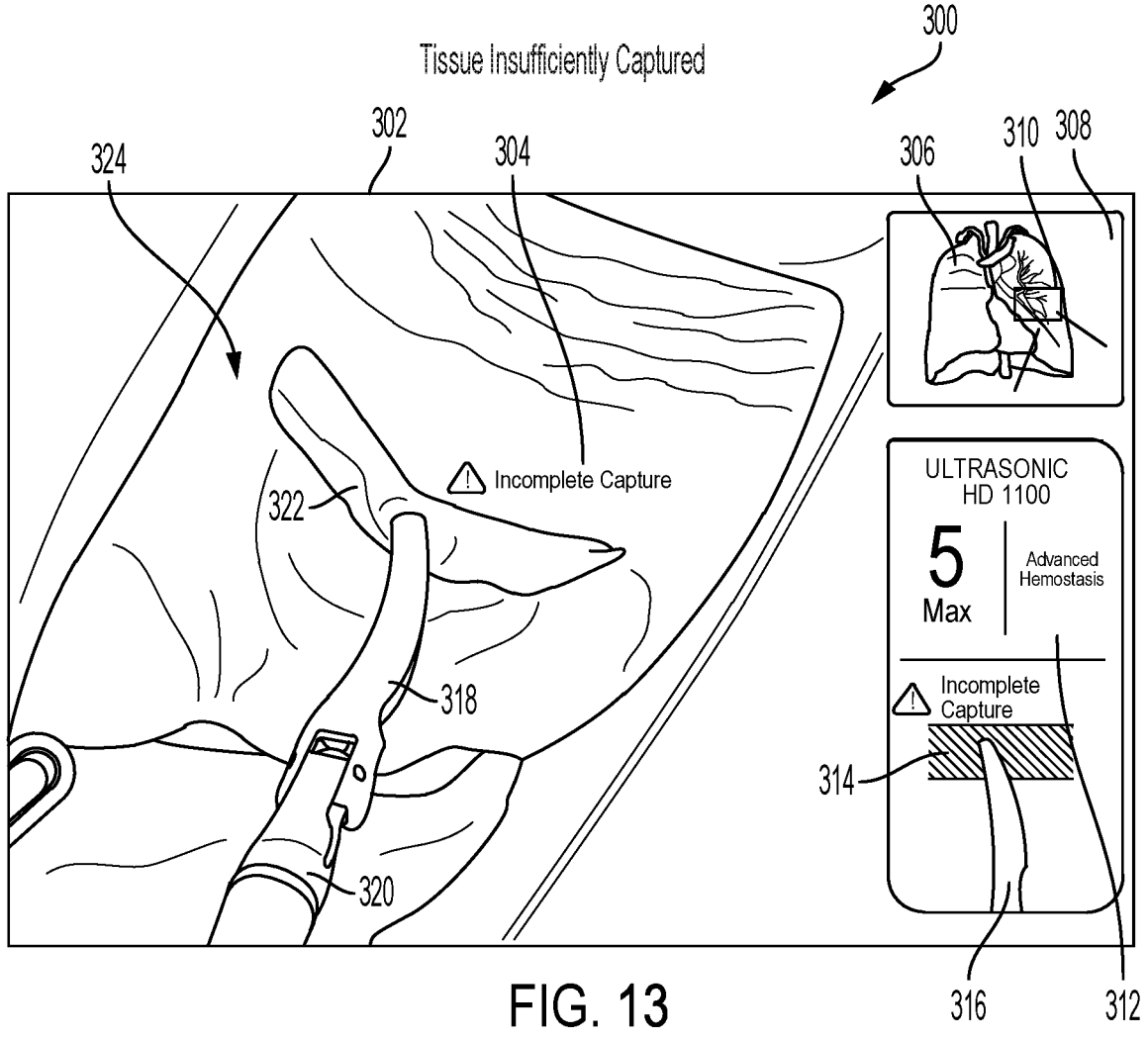
FIG. 13 is an augmented image of a live feed of a surgical area as visualized through a laparoscopic camera during a minimally invasive surgical procedure indicating tissue insufficiently captured between jaws of a surgical instrument end effector as a tissue aspect, according to one aspect of this disclosure.

FIG. 13 is an augmented image 300 of a live feed of a surgical area 324 as visualized through a laparoscopic camera during a minimally invasive surgical procedure indicating tissue 322 insufficiently captured between the jaws 318 of a surgical instrument end effector 320 as a tissue aspect. The laparoscopic field of view 302 of the surgical area 324 shows a surgical instrument end effector 320 grasping tissue 322 with the jaws 318 of the end effector 320. The augmented image 300 shows a graphical alert overlay 304 superimposed on the image of the surgical area 324 to indicate insufficiently captured tissue 322 relative to the end of cut in the jaws 318 of the end effector 320.

The augmented image 300 also comprises a first sub image 308 showing a graphic image 306 of the general anatomy superimposed on or adjacent to the surgical field of view 302 and a reference frame 310 of the actual anatomy superimposed on or adjacent to the surgical field of view 302. The augmented image 300 also comprises a second sub image 312 showing the type of surgical instrument in use, the energy level if applicable, and the current surgical procedure. The second sub image 312 may be superimposed on or located adjacent to the surgical field of view 302. The augmented image 300 shows an ultrasonic surgical instrument being used in a surgical procedure at an energy level set to 5 Max to achieve advanced hemostasis. A graphic image 316 of the surgical instrument is shown superimposed on a graphic image 314 of the incomplete tissue capture alert overlay 304. Accordingly, the augmented image 300 provides several virtual objects that inform the OR team of insufficiently captured tissue 322 relative to the end of cut. The superimposed incomplete tissue capture alert overlay 304 applies to energy based surgical instruments as well as surgical stapler instruments, and the like.

Figure 14:
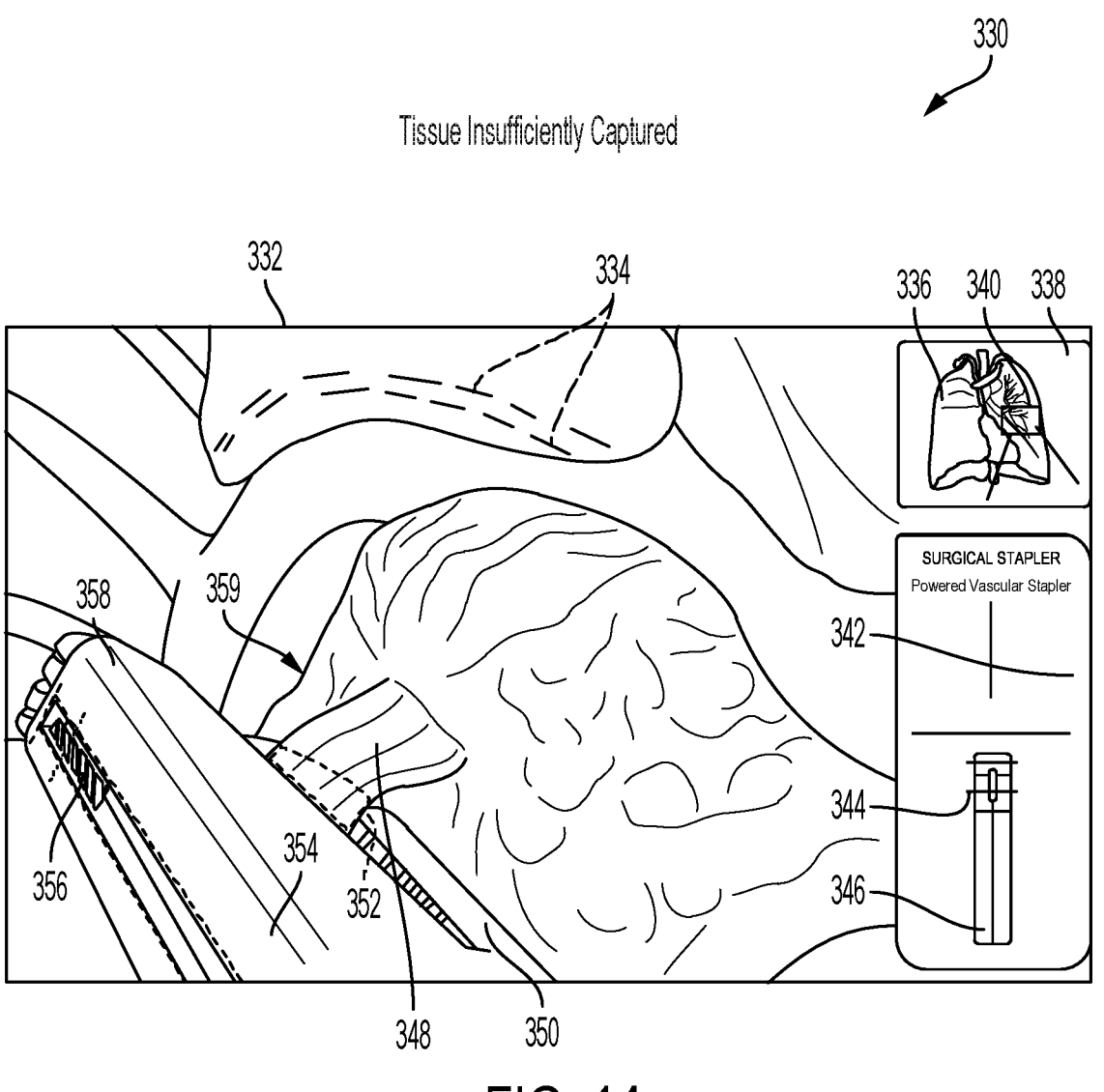
FIG. 14 is another augmented image of a live feed of a surgical area as visualized through a laparoscopic camera during a minimally invasive surgical procedure indicating tissue insufficiently captured between jaws of a surgical instrument end effector as a tissue aspect, according to one aspect of this disclosure.

FIG. 14 is another augmented image 330 of a live feed of a surgical area 359 as visualized through a laparoscopic camera during a minimally invasive surgical procedure indicating tissue 348 insufficiently captured between jaws 358 of a surgical instrument end effector 354 as a tissue aspect. The laparoscopic field of view 332 of the surgical area 359 shows a surgical instrument end effector 354 with insufficiently captured tissue 352 relative to the end of cut in the jaws 359, 358 of the end effector 354. The augmented image 330 shows a graphical alert overlay 352 superimposed on the tissue 348 to indicate incomplete tissue capture. In the illustrated example, a jaw 358, e.g., anvil, of the end effector 354 includes a series of light emitting diode (LED) indicators 356 to indicate the position of tissue 352 grasped with the jaws 350, 358 of the end effector 354. Also shown in the surgical field of view 332 are two rows of staples 334 in a previously stapled portion of tissue 352.

The augmented image 330 comprises a first sub image 338 showing a graphic image 336 of the general anatomy illustrated in the laparoscopic field of view 332 and a reference frame 340 of the actual anatomy shown in the laparoscopic field of view 332. The augmented image 330 comprises a second sub image 342 showing the type of instrument being used and the surgical procedure. In the illustrated example, a powered vascular surgical stapler is being used in a vascular surgical procedure. Also shown in the second sub image 342 is a graphic image of the stapler cartridge 346 of the powered surgical stapler and a graphic 344 superimposed on the graphic image of the stapler cartridge 346 to indicate the cut line of the powered surgical stapler.

Figure 15:
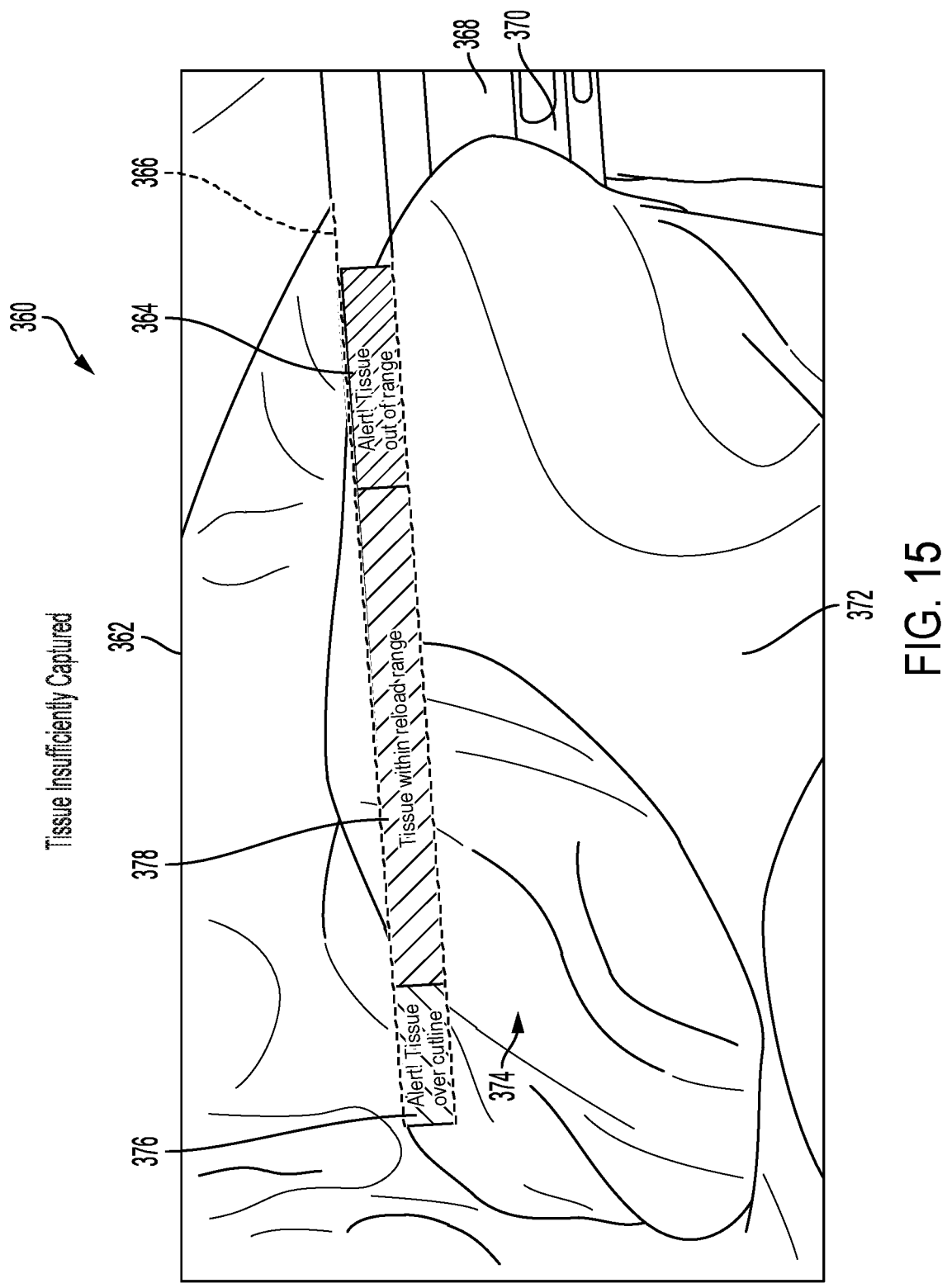
FIG. 15 is another augmented image of a live feed of a surgical area as visualized through a laparoscopic camera during a minimally invasive surgical procedure indicating tissue insufficiently captured between jaws of a surgical instrument end effector as a tissue aspect, according to one aspect of this disclosure.

FIG. 15 is another augmented image 360 of a live feed of a surgical area 374 as visualized through a laparoscopic camera during a minimally invasive surgical procedure indicating insufficiently captured tissue 372 between jaws 370 of a surgical instrument end effector 368 as a tissue aspect. The laparoscopic field of view 362 of a surgical area 374 shows a surgical instrument end effector 368 with insufficiently captured tissue 372 relative to the end of cut in the jaws 370 of the end effector 368. The augmented image 360 shows a graphical alert overlay 366 superimposed on the anvil of the end effector 368 to indicate incomplete tissue capture. A first superimposed alert 364 informs that the tissue 372 grasped at the proximal end of the jaws 370 of the end effector 368 is out of range. A second superimposed alert 378 informs that the tissue 372 grasped at the medial portion of the jaws 370 of the end effector 368 is within reload range. A third superimposed alert 376 informs that the tissue 372 grasped at the distal end of the jaws 370 in the end effector 368 is over the cut line.

Figure 16:
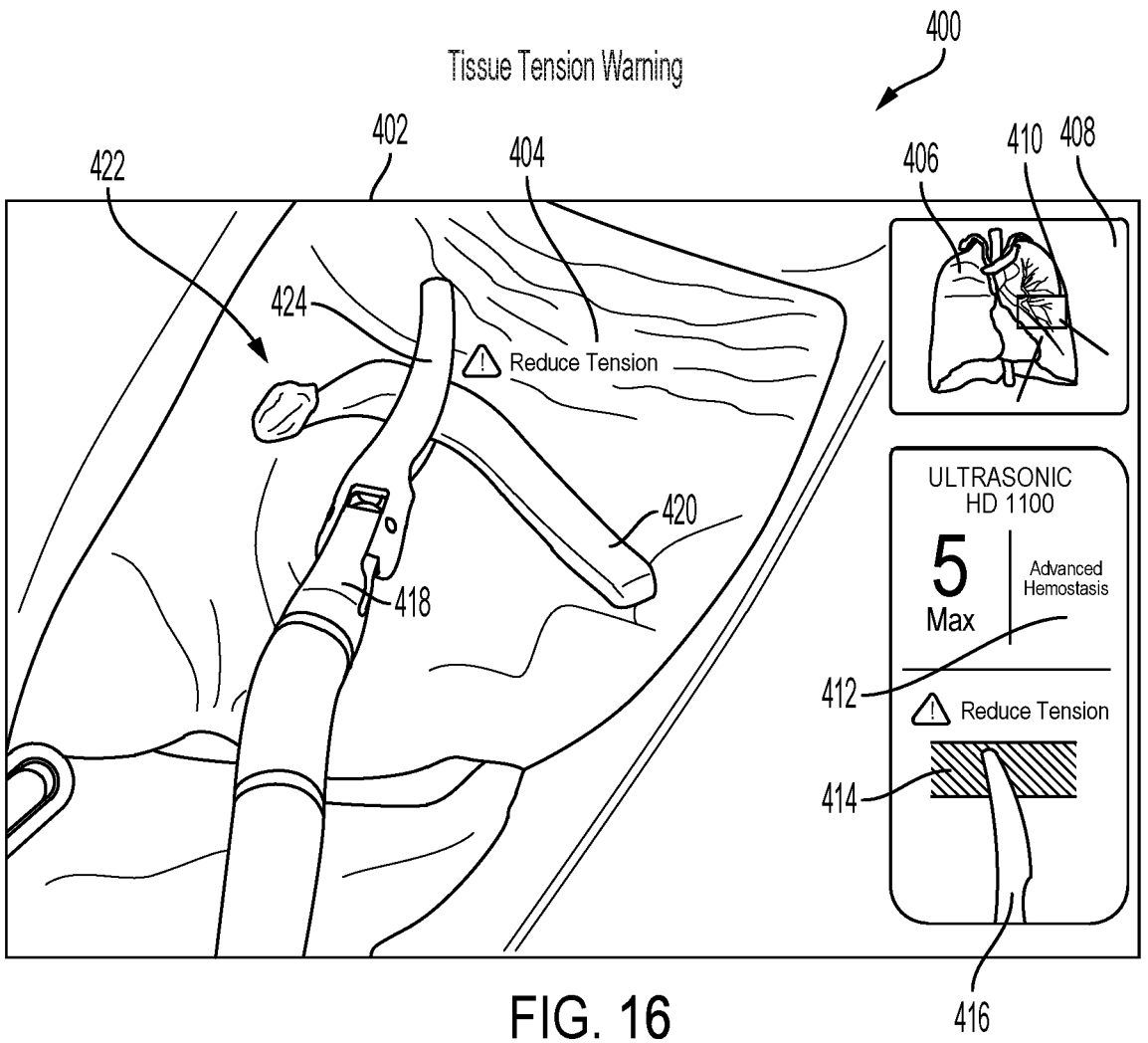
FIG. 16 is an augmented image of a live feed of a surgical area as visualized through a laparoscopic camera during a minimally invasive surgical procedure indicating tissue tension as a tissue aspect, according to at least one aspect of this disclosure.

FIG. 16 is an augmented image 400 of a live feed of a surgical area 422 as visualized through a laparoscopic camera during a minimally invasive surgical procedure indicating tissue 420 tension as a tissue aspect. The laparoscopic field of view 402 shows tissue 420 grasped between the jaws 424 of a surgical instrument end effector 418. The augmented image 400 shows a graphical alert overlay 404 superimposed in the surgical area 422 and a coloration of the tissue 420 to warn that the grasped tissue 420 is under tension. The superimposed tissue tension alert 404 and coloration of the tissue 420 grasped with the jaws 424 of the end effector 418 informs that the grasped tissue 420 is under tension. The superimposed tissue tension alert overlay 404 and coloration of tissue 420 under tension applies to energy based surgical instruments, surgical stapler instruments, as well as manipulation tools.

The augmented image 400 comprises a first sub image 408 showing a graphic image 406 of the general anatomy illustrated in the laparoscopic field of view 402 and a reference frame 410 of the actual anatomy shown in the laparoscopic field of view 402. The augmented image 400 also comprises a second sub image 412 showing the type of surgical instrument in use, the energy level being applied, if applicable, and the current surgical procedure. The augmented image 400 shows an ultrasonic surgical instrument being used in a surgical procedure at an energy level of 5 Max to achieve advanced hemostasis. A graphic image 416 of the surgical instrument is shown superimposed on a graphic image 414 of the reduce tension alert overlay 404. Accordingly, the augmented image 400 provides several options for informing the OR team to reduce the tension of the captured tissue 420 relative to the end of cut. The superimposed reduce tension alert overlay 404 applies to energy based surgical instruments as well as surgical stapler instruments, and the like.

Figure 17:
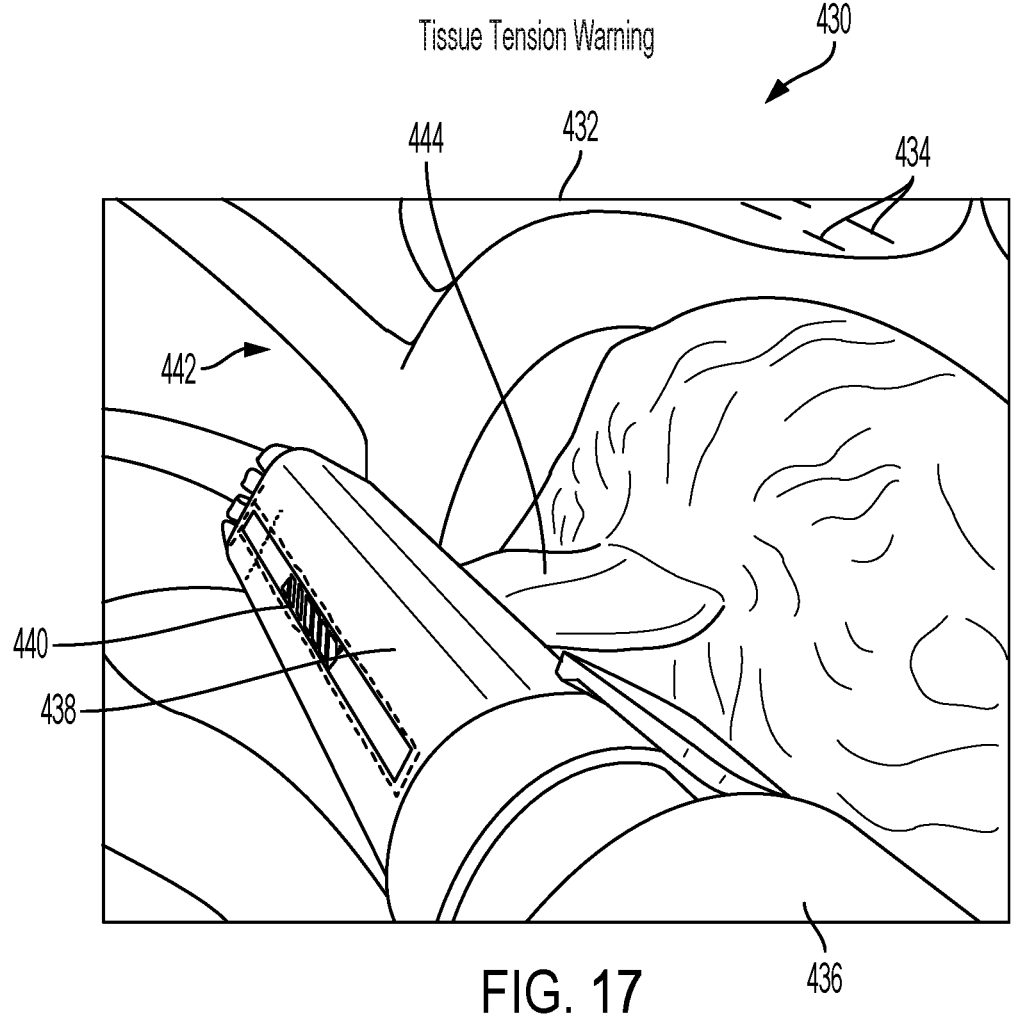
FIG. 17 is another augmented image of a live feed of a surgical area as visualized through a laparoscopic camera during a minimally invasive surgical procedure indicating tissue tension as a tissue aspect, according to one aspect of this disclosure.

FIG. 17 is another augmented image 430 of a live feed of a surgical area 442 as visualized through a laparoscopic camera during a minimally invasive surgical procedure indicating tissue 444 tension as a tissue aspect. The laparoscopic field of view 432 shows a surgical instrument end effector 436 grasping tissue 444 between the jaws 438 of the end effector 436. In the augmented image 430, coloration is added to the grasped tissue 444 to indicate that the grasped tissue 444 is under tension. Tissue 444 grasped with the jaws 438 of the end effector 436 is colored to indicate that the tissue 444 is under tension. Also shown in the laparoscopic field of view 432 are rows of previously applied staples 434. Also shown is a set of LEDs 440 to indicate the position of the tissue 444 grasped with the jaws 438 of the end effector 436.

Figure 18:
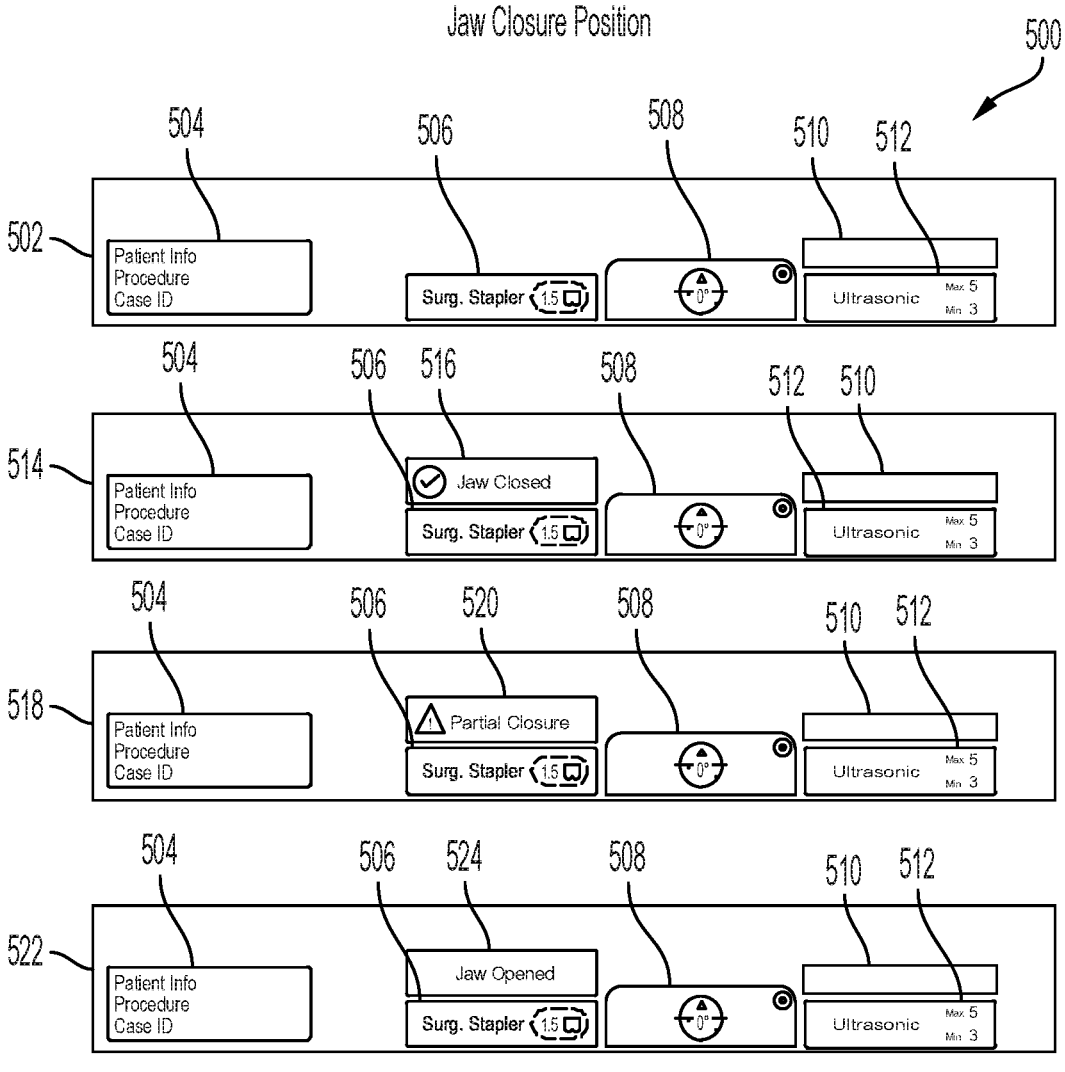
FIG. 18 is a plurality of graphic images indicating jaw closure position as an operational aspect of a surgical instrument as shown in FIGS. 11-17, according to one aspect of this disclosure.

FIG. 18 is a plurality of graphic images 500 indicating jaw closure position as an operational aspect of a surgical instrument as shown in FIGS. 11-17. The plurality of graphic images 500 comprise static graphics and alerts overlaid on the image of the surgical area and/or overlaid on the jaw of the end effector itself. The superimposed graphic images 500 apply to energy based surgical instruments, stapler based surgical instruments, manipulation tools, and the like.

A first image 502 comprises a first graphical overlay 504 showing the Patient Information, Procedure, and Case ID. A second graphical overlay 506 informs the type of surgical stapler instrument under use in the surgical procedure, e.g., a surgical stapler with a closed staple height of 1.5 mm as shown. A third graphical overlay 508 informs of the degree of articulation of the surgical stapler A fourth graphical overlay 510 is a pop-up error display. Finally, a fifth graphical overlay 512 informs of the energy surgical instrument under use in the surgical procedure, e.g., ultrasonic instrument operating between energy levels of 3 Min to 5 Max.

A second image 514 includes all of the graphical overlays 506, 508, 510, 512 explained in the description of the first image 502 with the addition of a sixth graphical overlay 516 that informs of the jaw of the surgical stapler being closed.

A third image 518 includes all of the graphical overlays 506, 508, 510, 512 explained in the description of the first image 502 with the addition of a sixth graphical overlay 520 that informs of the jaw of the surgical stapler being partially closed.

A fourth image 522 includes all of the graphical overlays 506, 508, 510, 512 explained in the description of the first image 502 with the addition of a sixth graphical overlay 524 that informs of the jaw of the surgical stapler being open.

Figure 19:
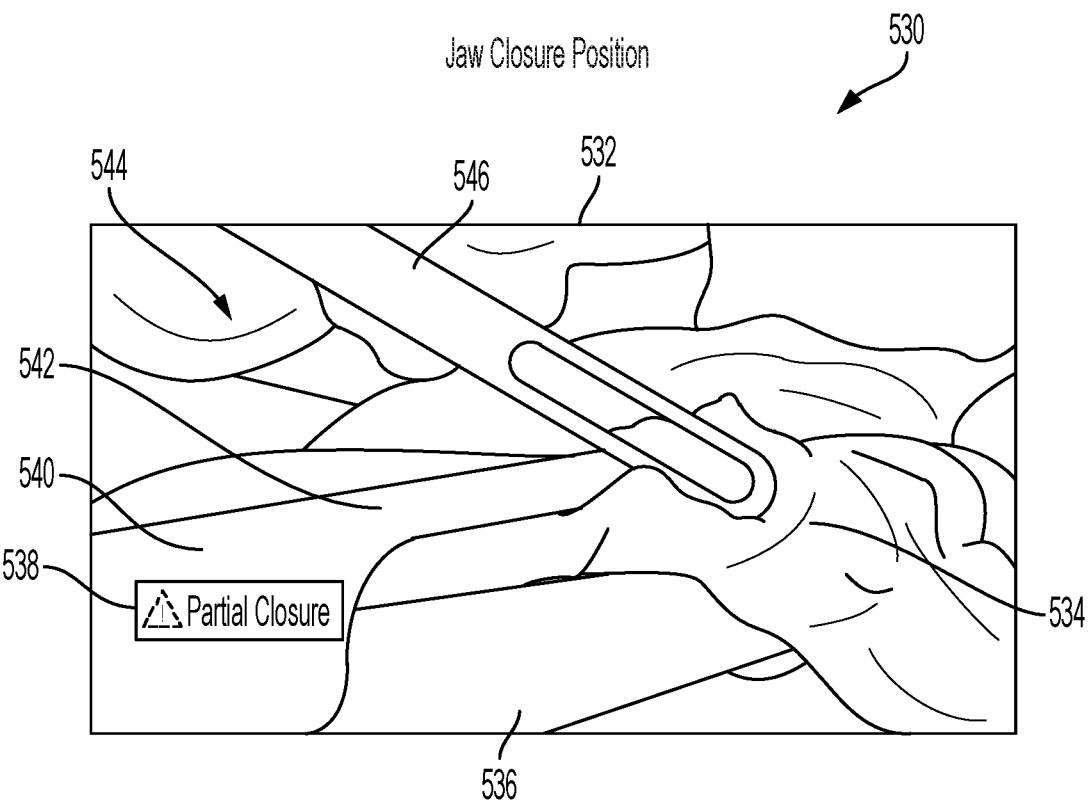
FIG. 19 is an augmented image of a live feed of a surgical area as visualized through a laparoscopic camera during a minimally invasive surgical procedure indicating jaw closure position as an operational aspect of a surgical instrument, according to one aspect of this disclosure.

FIG. 19 is an augmented image 530 of a live feed of a surgical area 544 as visualized through a laparoscopic camera during a minimally invasive surgical procedure indicating jaw 536, 542 closure position as an operational aspect of a surgical instrument. The laparoscopic field of view 532 shows a partially closed surgical instrument end effector 540 with tissue 534 grasped between the jaws 536, 542 of the end effector 540 and a tissue manipulation tool 546 used to assist the tissue grasping process. The augmented image 530 shows a graphical alert overlay 538 superimposed on the end effector 540 indicating partial closure.

Figure 20:
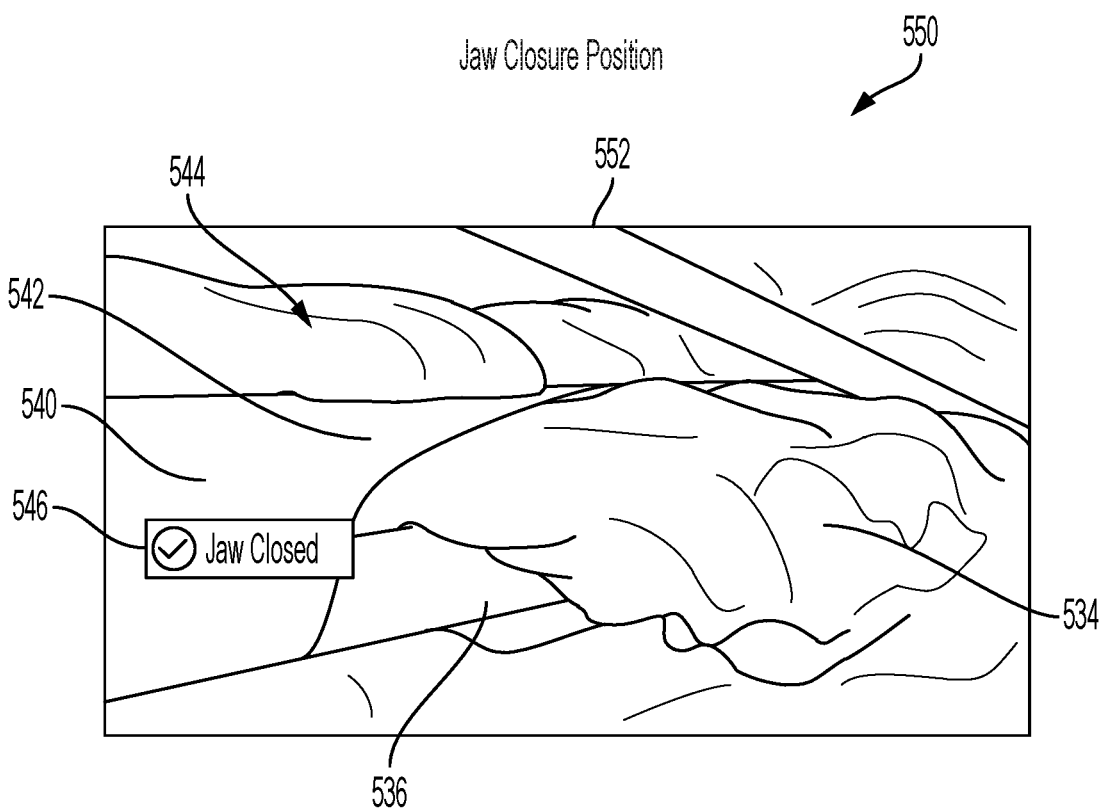
FIG. 20 is an augmented image of a live feed of the surgical area shown in FIG. 19 showing a fully closed surgical instrument end effector and a graphical alert overlay showing jaw closed position superimposed on the end effector, according to one aspect of this disclosure.

FIG. 20 is an augmented image 550 of a live feed of the surgical area 544 shown in FIG. 19 showing a fully closed surgical instrument end effector 540 and a graphical alert overlay 546 showing jaw closed position superimposed on the end effector 540. The laparoscopic field of view of the surgical area 544 shows tissue 534 grasped in the jaws 536, 542 of the end effector 540.

Figure 21:
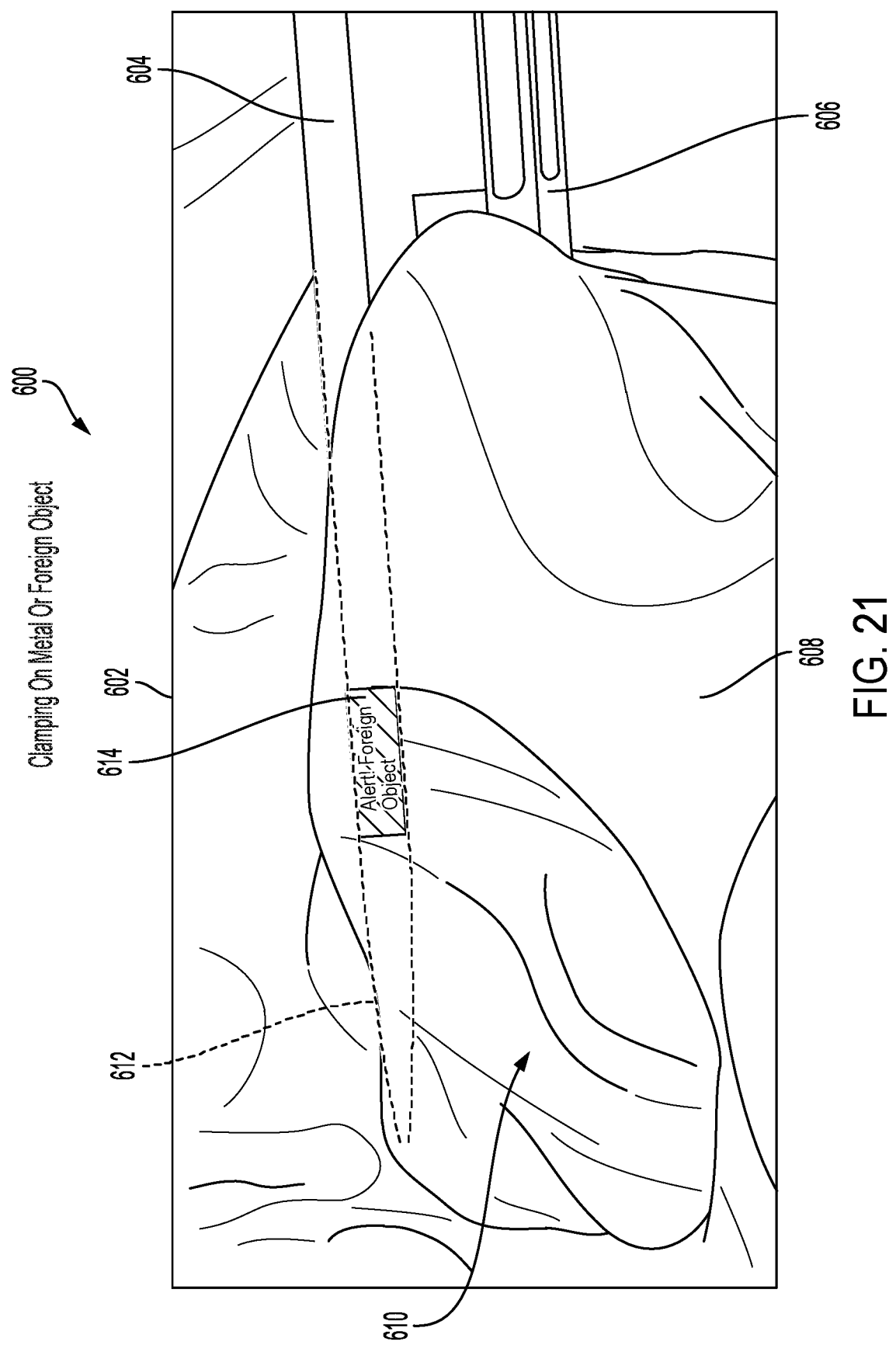
FIG. 21 is an augmented image of a live feed of a surgical area as visualized through a laparoscopic camera during a minimally invasive surgical procedure indicating clamping on metal or foreign object as an operational aspect of a surgical instrument, according to one aspect of this disclosure.

FIG. 21 is an augmented image 600 of a live feed of a surgical area 610 as visualized through a laparoscopic camera during a minimally invasive surgical procedure indicating clamping on metal or foreign object as an operational aspect of a surgical instrument. The laparoscopic field of view 602 of the surgical area 610 shows the surgical instrument end effector 604 clamped on a metal or foreign object embedded in the tissue 608. The augmented image 600 shows a graphical alert overlay 614 superimposed on a graphical overlay 612 of an upper jaw 606 of the end effector 604 showing a foreign object clamped between the jaws of the end effector 604.

Figure 22:
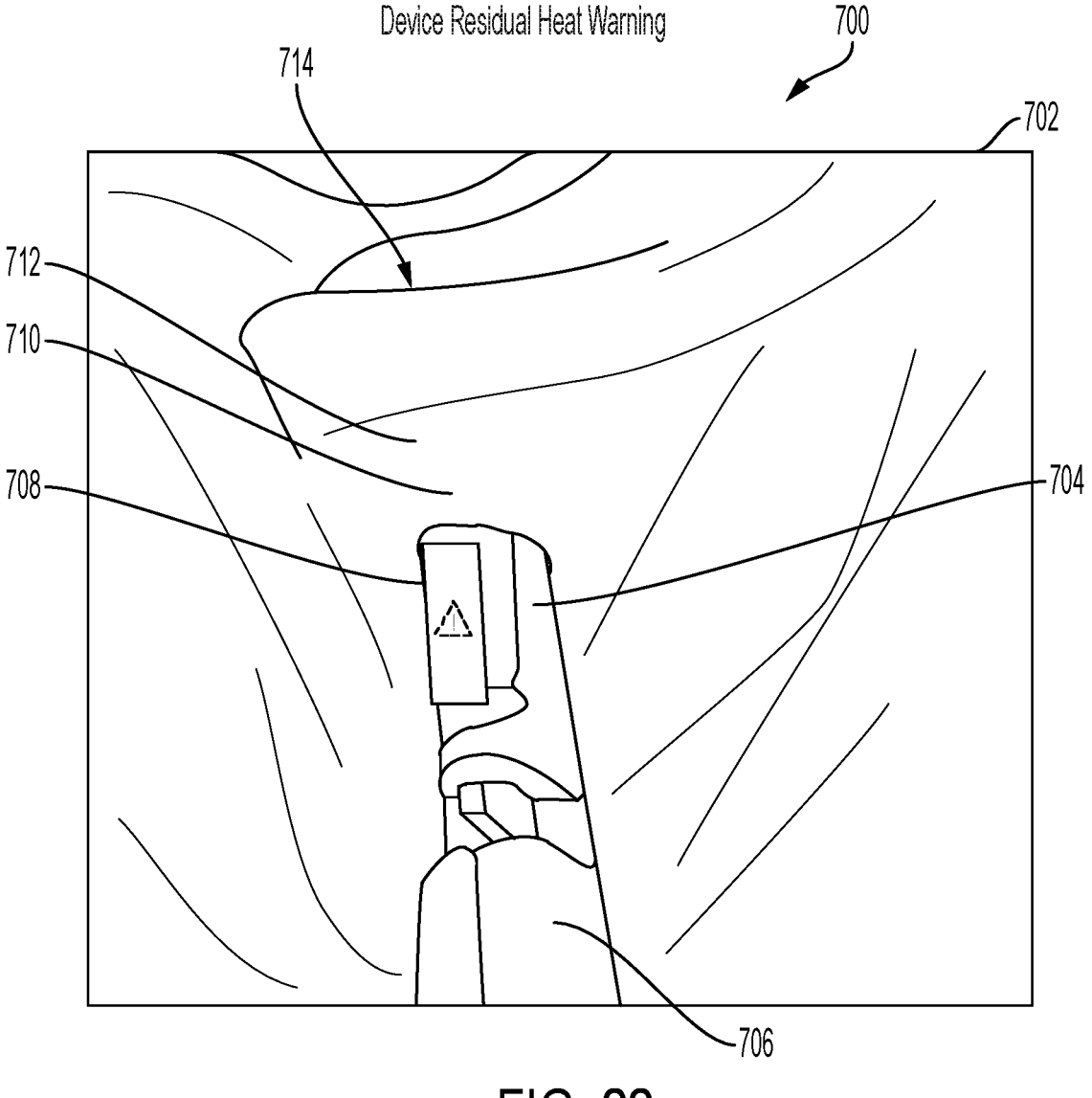
FIG. 22 is an augmented image of a live feed of a surgical area as visualized through a laparoscopic camera during a minimally invasive surgical procedure indicating device residual heat warning where overheating is an operational aspect of a surgical instrument, according to one aspect of this disclosure.

FIG. 22 is an augmented image 700 of a live feed of a surgical area 714 as visualized through a laparoscopic camera during a minimally invasive surgical procedure indicating device residual heat warning where overheating is an operational aspect of a surgical instrument. The laparoscopic field of view of the surgical area 714 shows a surgical instrument end effector 706 with tissue 710 clamped between an ultrasonic blade 710 and a clamp arm 704. The end effector 706 shows a hot ultrasonic blade 710. The augmented image 700 includes a graphical alert overlay 708 superimposed on the hot ultrasonic blade 710. The graphical alert overlay 708 warns the user that the ultrasonic blade 710 is building up residual heat, which will be transferred to the surrounding tissue 712 captured between the ultrasonic blade 710 and a clamp arm 704 pivotally coupled thereto.

Figure 23:
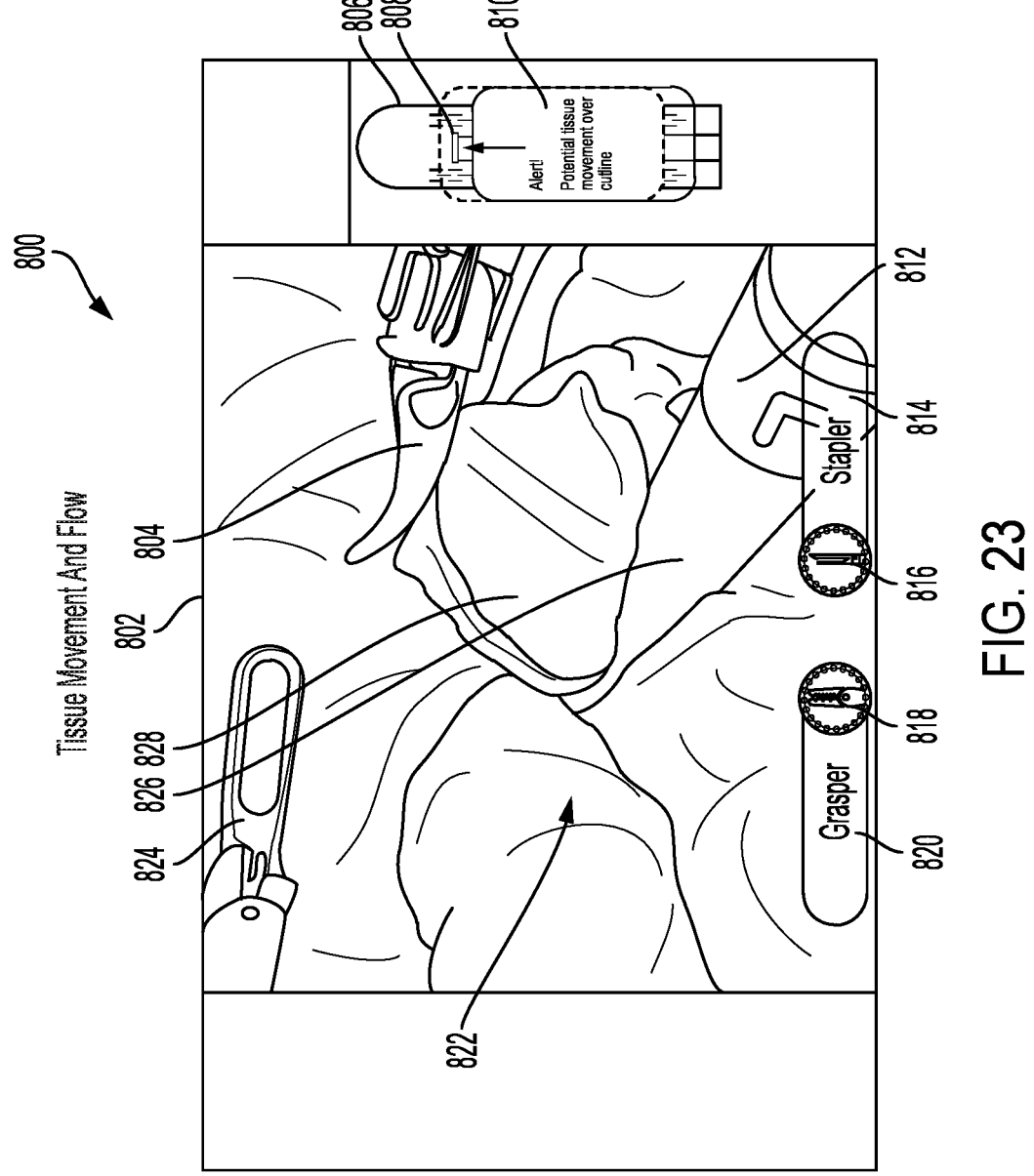
FIG. 23 is an augmented image of a live feed of a surgical area as visualized through a laparoscopic camera during a minimally invasive surgical procedure indicating tissue movement and flow is a tissue aspect, according to one aspect of this disclosure.

FIG. 23 is an augmented image 800 of a live feed of a surgical area 822 as visualized through a laparoscopic camera during a minimally invasive surgical procedure indicating tissue 828 movement and flow as a tissue aspect. The laparoscopic view of the surgical area 822 shows the movement and flow of tissue 828 relative to tissue graspers 804, 824 and a surgical instrument end effector 812 with the tissue 828 grasped in the jaws 824 of the end effector 812 and the jaws of the tissue graspers 804, 824. The augmented image 800 shows graphical images 814, 820 overlaid on surgical area 822. The first graphical image 814 includes an icon 816 of a surgical stapler and text identifying the surgical instrument as a "stapler." The second image 820 includes an icon of a grasper 818. A sub image 810 alerts the OR team (e.g., the surgeon) of potential tissue movement over the cutline 808 displayed over an outline of the stapler cartridge 806.

Figure 24:
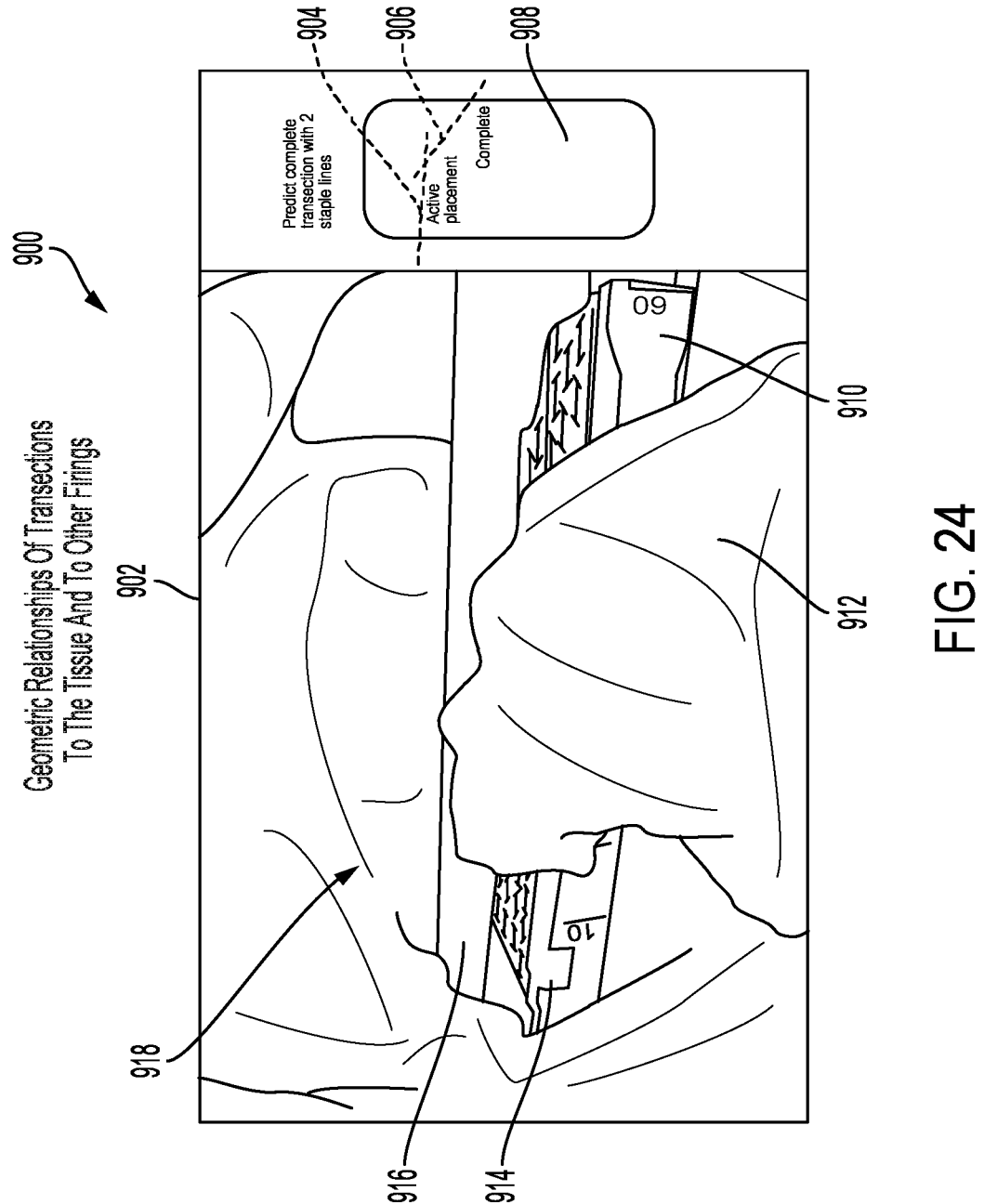
FIG. 24 is an augmented image of a live feed of a surgical area as visualized through a laparoscopic camera during a minimally invasive surgical procedure indicating the geometric relationship of the transections to tissue and other firings is a tissue aspect, according to one aspect of this disclosure.

FIG. 24 is an augmented image 900 of a live feed of a surgical area 918 as visualized through a laparoscopic camera during a minimally invasive surgical procedure indicating the geometric relationship of the transections to tissue 912 and other firings as a tissue aspect. The laparoscopic view of the surgical area 918 shows a surgical instrument end effector 910 and the geometric relationships of transections to the tissue 912 grasped between the jaws 914, 916 of the end effector 910 and to other firings. The augmented image 900 shows graphical images overlaid on the surgical area 918. A sub image 908 includes graphics that predict a complete transection with two staple lines shown graphically as active placement staple line 904 and complete staple line 906.

Figure 25:
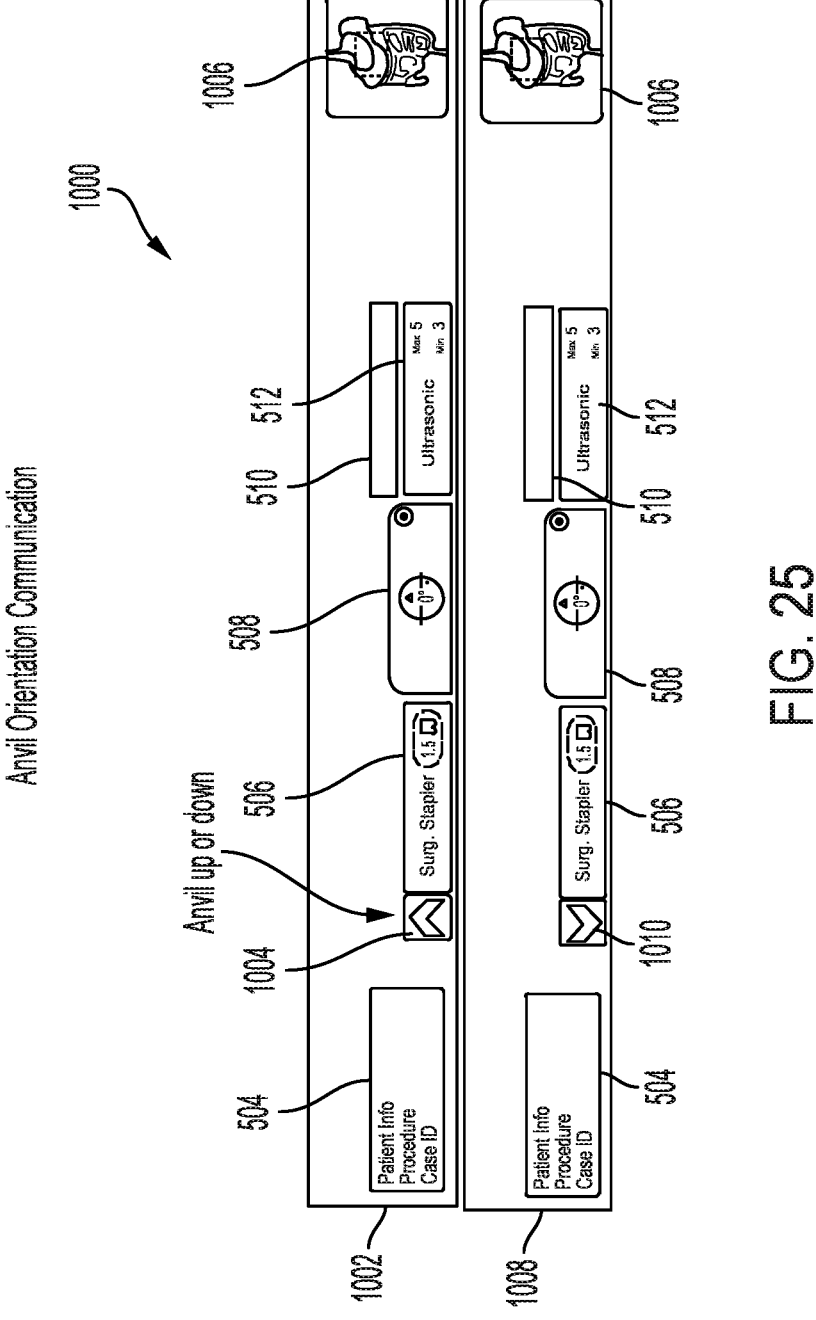
FIG. 25 is an image showing anvil orientation communication as an operational aspect of a surgical instrument, according to one aspect of this disclosure.

FIG. 25 is an image 1000 indicating anvil orientation communication as an operation as an operational aspect of a surgical instrument. A first image 1002 shows all of the graphical overlays 504, 506, 508, 510, 512 of the explained in the description of the first image 502 shown in FIG. 18 with the addition of an anvil up/down indicator graphic 1004. In the illustrated example, the up/down indicator graphic 1004 shows that the anvil is in the up (e.g., open) position. Another image 1006 illustrates the anatomy. A second image 1008 shows all of the graphical overlays 504, 506, 508, 510, 512 of the explained in the description of the first image 502 shown in FIG. 18 and the image 1006 of the anatomy with the addition of an anvil up/down indicator graphic 1010. In the illustrated example, the up/down indicator graphic 1010 shows that the anvil is in the down (e.g., closed) position.

Figure 26:
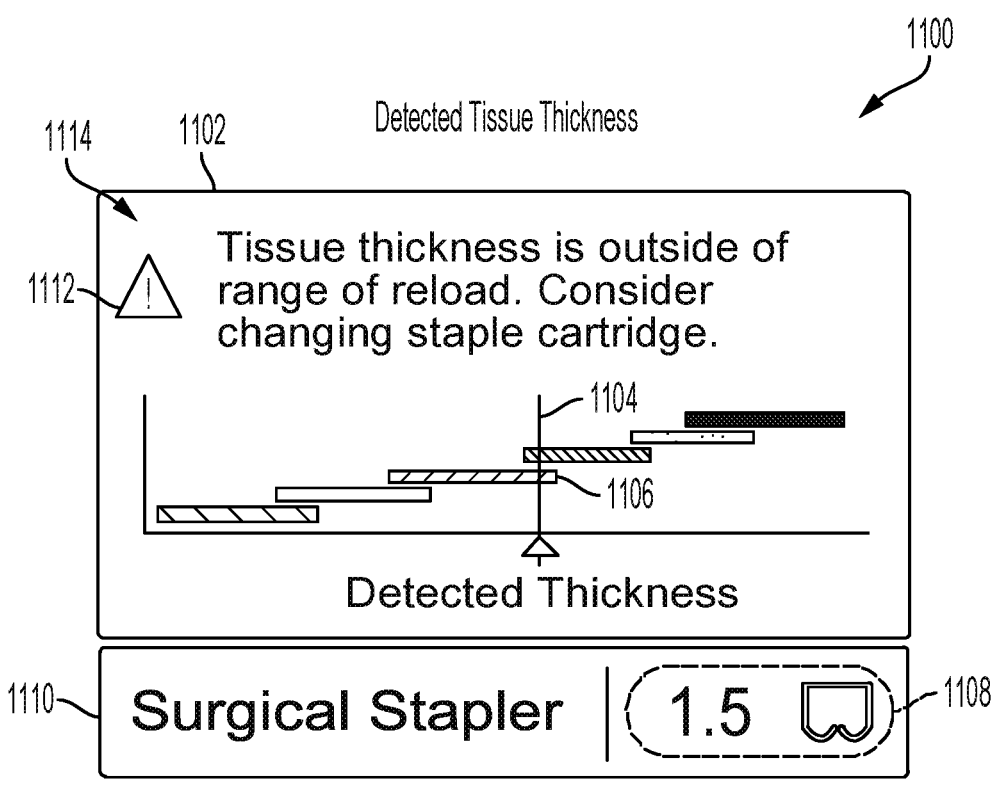
FIG. 26 is an image showing detected tissue thickness in the jaws of a surgical instrument end effector where tissue thickness is a tissue aspect, according to one aspect of this disclosure.

FIG. 26 is an image 1100 indicating detected tissue thickness in the jaws of a surgical instrument end effector where tissue thickness is a tissue aspect. The image 1100 shows a graphic screen 1102 with text 1114 that tissue thickness is outside of range of reload with a recommendation to consider changing staple cartridge ad a warning icon 1112. The graphic screen 1102 shows a detected thickness marker 1104 positioned along a scale 1106 that shows detected tissue thickness. The graphic screen 1102 also shows the type of surgical instrument in use. The type of surgical instrument in use is a surgical stapler 1110 with a closed staple height 1108 of 1.5 mm.

Figures 27, 28, 29:
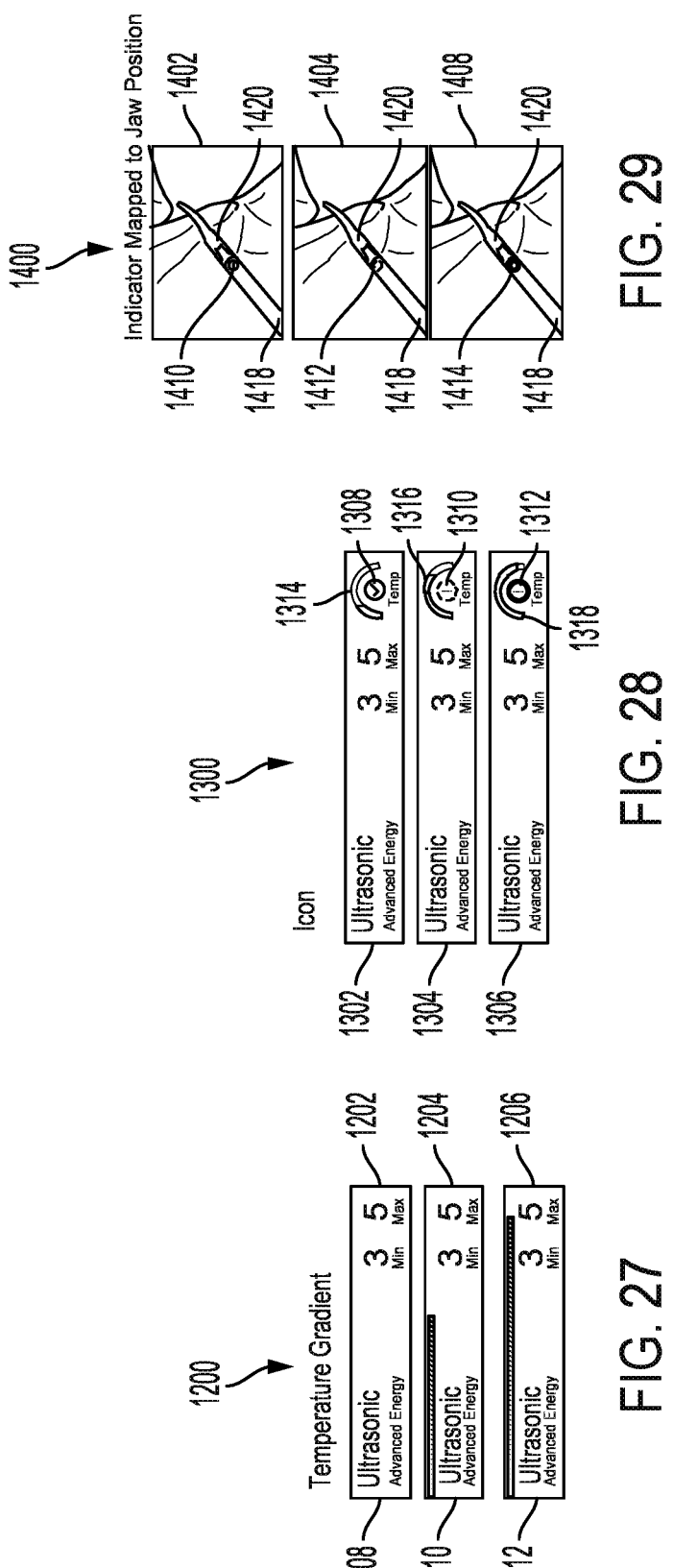
FIG. 27 is an image of temperature gradient display graphics for an ultrasonic instrument, according to one aspect of this disclosure.
FIG. 28 is an image of temperature icon display graphics for an ultrasonic instrument, according to one aspect of this disclosure.
FIG. 29 is an image of an ultrasonic blade temperature graphic elements mapped to an end effector jaw position, according to one aspect of this disclosure.

FIG. 27 is an image 1200 of temperature gradient display graphics 1202, 1204, 1206 for an ultrasonic instrument. The first, second, and third display graphic 1202, 1204, 1206 may be overlaid on a surgical area of a surgical field of view displayed on a display as described in FIGS. 11-26, informs of the instrument type, minimum and maximum output energy levels, and displays temperature gradient elements 1208, 1210, 1212 on a portion of the display graphic 1202, 1204, 1206. In the first display graphic 1202 the ultrasonic instrument is either off or the ultrasonic blade temperature is running at a normal temperature and a "green" gradient bar is not displayed or barely visible. In the second display graphic 1204 a temperature gradient element 1210 "heat map bar" ranging from green to yellow shows that the ultrasonic blade is approaching a temperature above normal. In the third display graphic 1206 a temperature gradient element 1212 "heat map bar" ranging from green to red shows that the ultrasonic blade temperature is above normal in an overheated state.

FIG. 28 is an image 1300 of temperature icon display graphics 1302, 1304, 1306 for an ultrasonic instrument. The first, second, and third display graphics 1302, 1304, 1306 may be overlaid on a surgical area of a surgical field of view displayed on a display as described in FIGS. 11-26, informs of the instrument type, minimum and maximum output energy levels, and displays temperature green, yellow, and red icons 1308, 1310, 1310 on a portion of the display graphic 1302, 1304, 1306. In the first display graphic 1302 the ultrasonic instrument is operating in a normal condition and the temperature of the ultrasonic blade is in a normal range as shown by green icon 1308 and also shown by green semicircular temperature meter element 1314. In the second display graphic 1304 the yellow temperature icon 1310 shows that the ultrasonic blade is approaching a temperature above normal as also shown by the yellow semicircular temperature meter element 1316. In the third display graphic 1306 a red temperature icon 1312 shows that the ultrasonic blade temperature is above normal and is in a overheated state as shown by the red semicircular temperature meter element 1318.

FIG. 29 is an image 1400 of ultrasonic blade temperature graphic elements 1410, 1412, 1414 mapped to an end effector 1418 jaw 1420 position. The first, second, and third display graphic elements 1410, 1412, 1414 may be overlaid on the jaw 1420 of an ultrasonic end effector 1418 in a surgical area of a surgical field of view displayed on a display as described in FIGS. 11-26. The first temperature graphic element 1410 shows that the ultrasonic blade is operating in a normal range as shown by the green temperature graphic element 1410. The second temperature graphic element 1412 shows that the ultrasonic blade is approaching a heated temperature state as shown by the yellow temperature graphic element 1412. The third temperature graphic element 1414 shows that the ultrasonic blade is in an overheated temperature state as shown by the red temperature graphic element 1414.

Figures 30, 31, 32, 33, 34, 35:
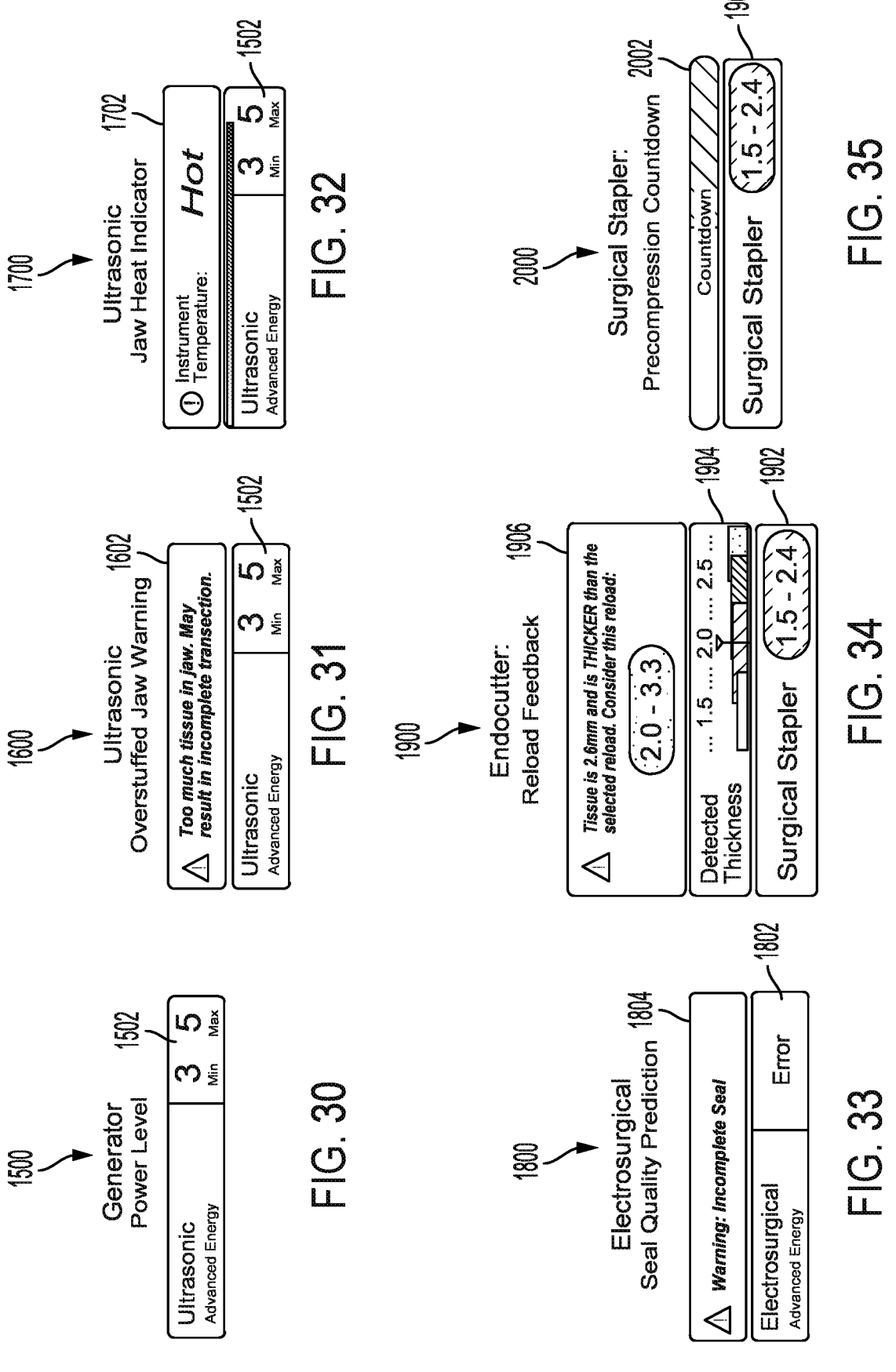
FIG. 30 is an image of an ultrasonic generator power level display graphic, according to one aspect of this disclosure.
FIG. 31 is an image of an ultrasonic generator power level display graphic with a pop-up warning graphic indicating that the ultrasonic end effector jaw is overstuffed, according to at aspect of this disclosure.
FIG. 32 is an image of an ultrasonic generator power level display graphic with a pop-up warning graphic indicating ultrasonic end effector jaw heat, according to one aspect of this disclosure.
FIG. 33 is an image of an electrosurgical generator display graphic with a pop-up warning graphic indicating electrosurgical seal quality prediction, according to one aspect of this disclosure.
FIG. 34 is an image of a surgical stapler reload feedback, according to one aspect of this disclosure.
FIG. 35 is an image of a surgical stapler precompression countdown, according to one aspect of this disclosure.

FIG. 30 is an image 1500 of an ultrasonic generator power level display graphic 1502. The display graphic 1502 informs of the generator type and minimum and maximum power levels. One or more graphic elements of the image 1500 may be overlaid on the jaw of the ultrasonic end effector or anywhere in the surgical area in the surgical field of view displayed on a display as described in FIGS. 11-26.

FIG. 31 is an image 1600 of an ultrasonic generator power level display graphic 1502 with a pop-up warning graphic 1602 indicating that the ultrasonic end effector jaw is overstuffed. The pop-up warning graphic 1602 may include the language to show that too much tissue is in the jaw and may result in an incomplete transection. One or more graphic elements of the image 1600 may be overlaid on the jaw of the ultrasonic end effector or anywhere in the surgical area in the surgical field of view displayed on a display as described in FIGS. 11-26.

FIG. 32 is an image 1700 of an ultrasonic generator power level display graphic 1502 with a pop-up warning graphic 1702 indicating ultrasonic end effector jaw heat. The pop-up warning graphic 1702 may include the language to show that the instrument temperature is hot and in one aspect, the word hot may be shown in red. One or more graphic elements of the image 1700 may be overlaid on the jaw of the ultrasonic end effector or anywhere in the surgical area in the surgical field of view displayed on a display as described in FIGS. 11-26.

FIG. 33 is an image 1800 of an electrosurgical generator display graphic 1802 with a pop-up warning graphic 1802 indicating electrosurgical seal quality prediction. The pop-up warning graphic 1804 may include the language Warning: Incomplete Seal and the electrosurgical generator display graphic 1802 may include the language Error to show that an incomplete seal is predicted. One or more graphic elements of the image 1800 may be overlaid on the jaw of the electrosurgical end effector or anywhere in the surgical area in the surgical field of view displayed on a display as described in FIGS. 11-26.

FIG. 34 is an image 1900 of a surgical stapler reload feedback. The image 1900 comprises a first display graphic 1902 indicating a suitable tissue thickness range for the surgical stapler in use. In the illustrated example, the suitable surgical stapler tissue thickness range is 1.5 mm-2.4 mm. A second display graphic 1904 shows the detected tissue thickness. In the illustrated example, the detected tissue thickness is 2.6 mm. A third pop-up display graphic 1906 shows that the tissue thickness is 2.6 mm and is thicker than the selected reload and provides a suggestion to consider a reload in the range of 2.0 mm-3.3 mm. The image 1800 may be overlaid on the jaw of the electrosurgical end effector or anywhere in the surgical area in the surgical field of view displayed on a monitor or screen. One or more graphic elements of the image 1900 may be overlaid on the jaw/anvil of the surgical stapler end effector or anywhere in the surgical area in the surgical field of view displayed on a display as described in FIGS. 11-26.

FIG. 35 is an image 2000 of a surgical stapler precompression countdown. The image 2000 comprises a first display graphic 1902 as shown in FIG. 34 indicating the surgical stapler tissue thickness range of 1.5 mm-2.4 mm. A second pop-up display graphic 2002 shows a surgical stapler precompression countdown element to show the time remaining in the precompression phase of the surgical stapler operation. One or more graphic elements of the image 2000 may be overlaid on the jaw/anvil of the surgical stapler end effector or anywhere in the surgical area in the surgical field of view displayed on a display as described in FIGS. 11-26.

The following description provides an intraoperative display for surgical systems to provide adaptation and adjustability or overlaid instrument information. One aspect provides functional overlay of instrument critical operations or parameters to clearly represent a surgical stapler or energy device or aspects of each of its interaction with tissue during a surgical procedure. Overlaid data may be adjusted by aspects detected by the surgical hub to modify the overlay from the information merely detected by the source instrument to add context. The displays may be adjusted or modified by the user and as a result also result in modifications of the instrument being monitored operation.

FIGS. 36-68 describe an intraoperative display system for use during a surgical procedure. The system comprises a surgical monitor with an intraoperative data display of a surgical area. An advanced energy generator is coupled to an advanced energy surgical instrument. The advanced energy surgical instrument employs radio frequency (RF) energy and ultrasonic energy during a surgical procedure on a patient. A surgical hub is coupled to the advanced energy generator and to the surgical monitor. The surgical hub provides a live feed of the surgical area to the surgical monitor to display the live feed of the surgical area by the intraoperative data display. The intraoperative data display displays a view of the surgical area including the advanced energy surgical instrument grasping tissue and a panel overlay that displays information specific to the advanced energy surgical instrument.

One aspect, the intraoperative data display shows an end effector of the surgical instrument grasping tissue and a panel overlay displaying case information, systems notifications, or device panels, or any combination thereof, overlaid over the live surgical feed. A location, opacity, size and placement of the panel overlay is customized. The panel overlay is configured to be turned on or off individually or turned on/off as a group. The panel overlay is further configured to change dynamically to show state changes such as device activation or power level adjustment. The panel overlay depicts optimal device performance (ODP) guide images or other instructions for use (IFU)/informational sources.

In various aspects the panel overlay comprises at least one of data input information from capital equipment, generators, insufflator, smoke evacuator, electronic health record, laparoscope, computer, surgical devices, wired and wirelessly connected devices, surgeon profile preferences that may be saved, recalled or edited, or any combination thereof. The panel overlay may include case information including at least one of Patient Name, Surgeon Name, Case Time, or Instrument Activations, or combinations thereof. The panel overlay may include system notifications including at least one of connect instrument status, minor error alert, medium error alert, or major error alert, or any combination thereof. The panel overlay may include information associated with the surgical instrument connected to the system to provide advanced hemostasis. The panel overlay may include a visible patient panel overlay. The panel overlay may include a device panel overlay comprising at least one of device name, device settings, or device supplemental features, or any combination thereof. The panel overlay may include a plurality of panel overlays in a stacked configuration. The panel overlay may include a plurality of panel overlays in an expanded configuration. The panel overlay may display device troubleshooting information. The panel overlay may display at least one of alerts, warnings, device information, or device features, or any combination thereof.

In another aspect, the intraoperative data display comprises a secondary configurable panel. The secondary configurable panel changes dynamically based on the selected customized laparoscopic overlay fields displayed in the surgical field of view of a live surgical feed area of the intraoperative data display. The customized laparoscopic overlay fields comprise at least one of a bottom edge panel, a top left corner panel, a top center panel, or a side edge panel, or any combination thereof.

Figure 36:
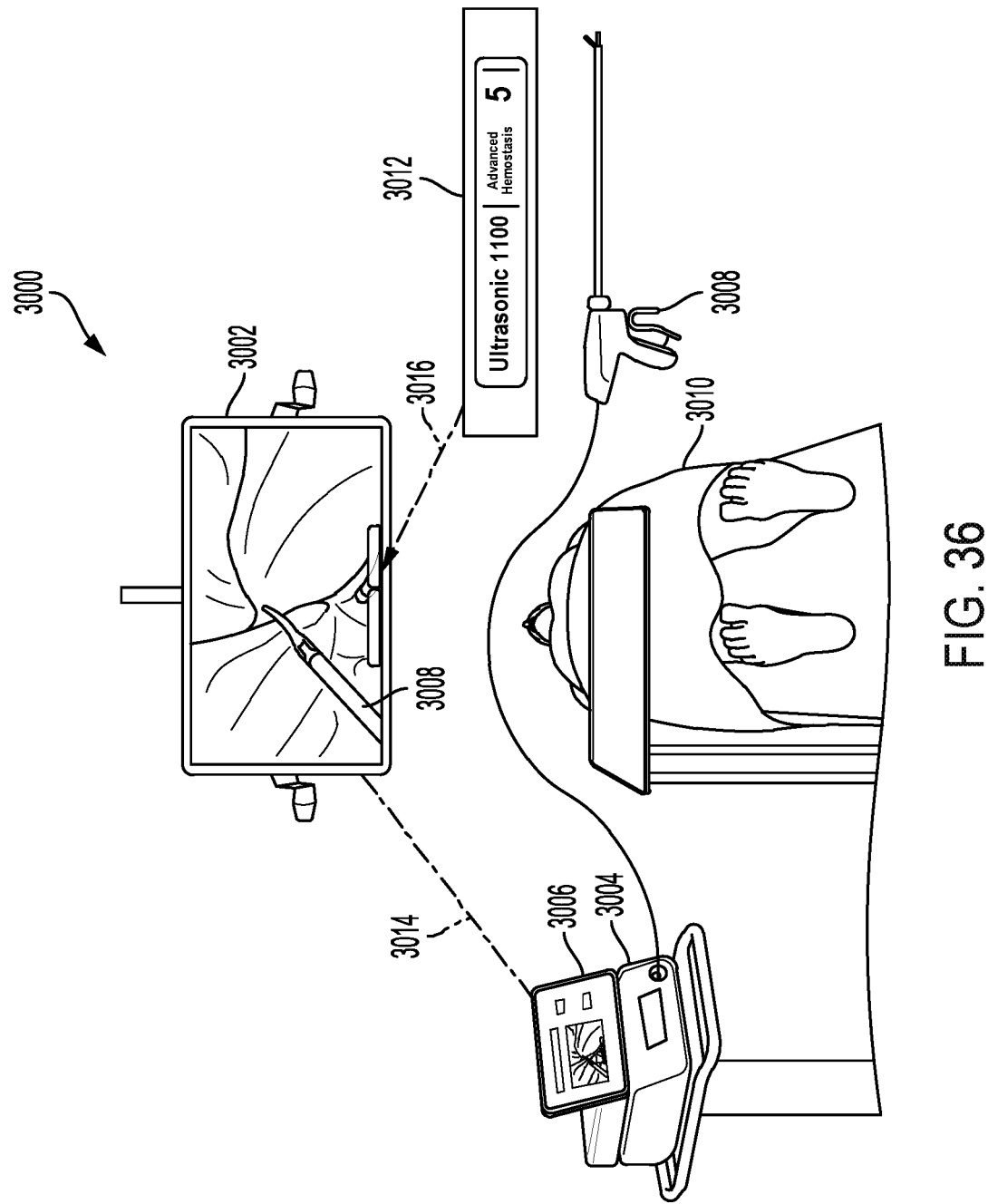
FIG. 36 is a system diagram of a surgical suite comprising a surgical monitor with intraoperative data display of a surgical area, according to one aspect of this disclosure.

FIG. 36 is a system diagram 3000 of a surgical suite comprising a surgical monitor with intraoperative data display 3002 of a surgical area. An advanced energy generator 3004 is coupled to a surgical hub 3006 and to an advanced energy surgical instrument 3008. The advanced energy surgical instrument 3008 employs RF energy and ultrasonic energy during a surgical procedure on a patient 3010. The surgical hub 3006 provides a live feed 3014 of the surgical area, which is displayed by the intraoperative data display 3002. The intraoperative data display 3002 displays a view of the surgical area including the advanced energy surgical instrument 3008 grasping tissue and a panel overlay 3012 that displays information specific to the advanced energy surgical instrument 3008.

Figure 37:
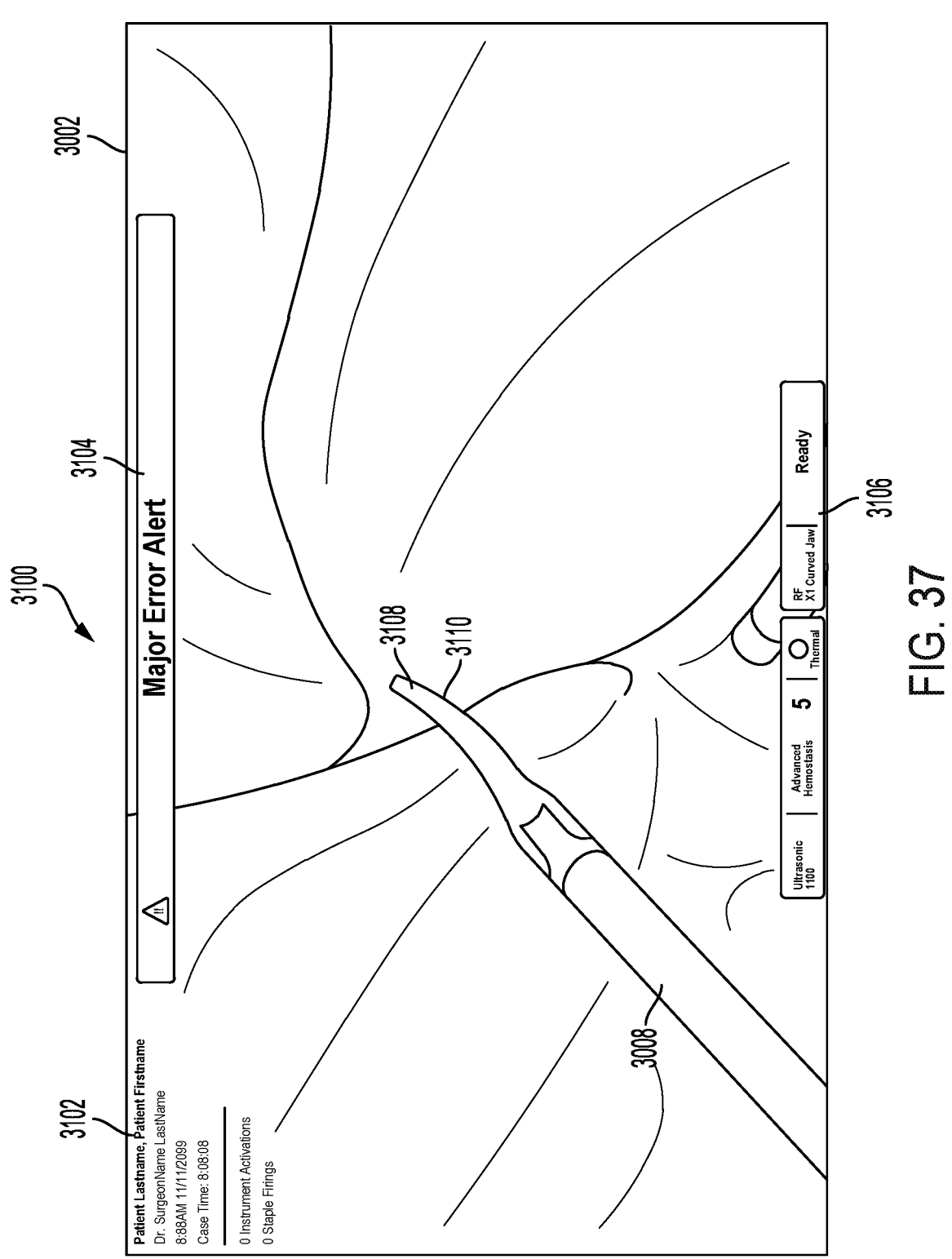
FIG. 37 is an augmented image of a live feed of a surgical area as visualized through a laparoscopic camera during a minimally invasive surgical procedure displayed on an intraoperative data display, according to one aspect of this disclosure.

FIG. 37 is an augmented image 3100 of a live feed of a surgical area as visualized through a laparoscopic camera during a minimally invasive surgical procedure displayed on an intraoperative data display 3002. The laparoscopic field of view shows an end effector 3108 of a surgical instrument 3008 grasping tissue 3110. The augmented image 3100 shows three panel overlays displaying case information 3102, systems notifications 3104, and device panels 3106 overlaid over the live surgical feed.

The panel overlays 3102, 3104, 3106 are displayed on the live surgical feed. The location, opacity, size and placement of the panel overlays 3102, 3104, 3106 can be customized. The panel overlays 3102, 3104, 3106 may be turned on or off individually or turned on/off as a group. The panel overlays 3102, 3104, 3106 may be opaque or have varying levels of transparency. The panel overlays 3102, 3104, 3106 may include data input information from capital equipment, generators, insufflator, smoke evacuator, electronic health record, laparoscope, computer, surgical devices, wired and wirelessly connected devices. Surgeon profile preferences may be saved, recalled or edited. In other aspects, general screen settings including overall screen settings and fonts for panel overlay 3102, 3104, 3106 sizing may be configurable based upon surgeon preferences via a staff console. The panel overlays 3102, 3104, 3106 features on all screen displays may be enables/disabled, or bypassed through a dedicated physical switch, for example.

FIG. 38 is a detailed view of the case information panel overlay 3102 shown in FIG. 37. The case information panel overlay 3102 may be selectively enabled/disabled via the staff console. Specific details of the case information panel overlay 3102 including Patient Name, Surgeon Name, Case Time, Instrument Activations, etc., may be selectively enabled/disabled based on the staff console settings Other aspects of the case information panel overlay 3102 may include, for example, enabling the screen at the start of the surgery and disabling the screen after a specific criteria is met (surgery time elapsed number of device activations, etc.).

Figures 39, 40, 41:
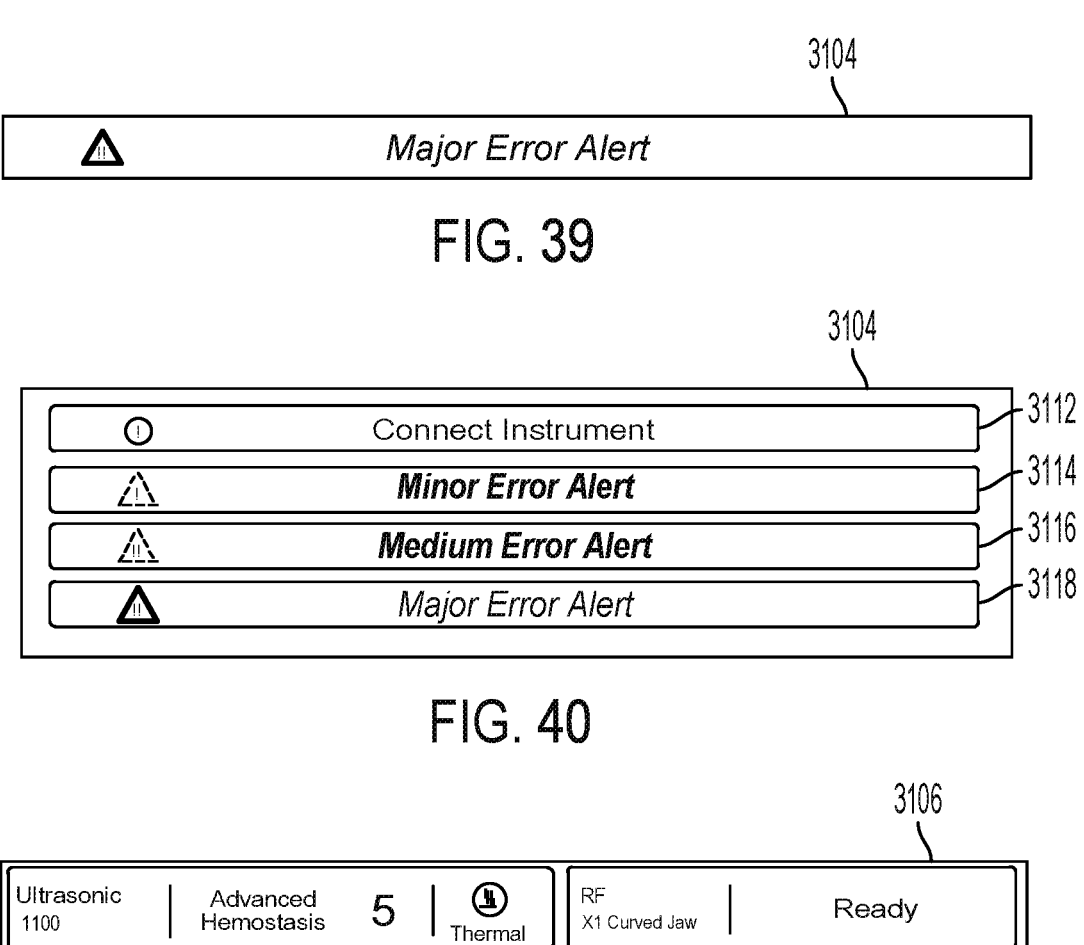
FIG. 39 is a detailed view of the systems notifications panel overlay shown in FIG. 37, according to one aspect of this disclosure.
FIG. 40 is an image of several examples of systems notifications panel overlays, according to one aspect of this disclosure.
FIG. 41 is a detailed view of the device panels overlay shown in FIG. 37, according to one aspect of this disclosure.

FIG. 39 is a detailed view of the systems notifications panel overlay 3104 shown in FIG. 37. The systems notifications panel display overlay 3104 may comprise a warning symbol that may be variable based on the severity of the warning/alert/information. The message may be potentially based on any combination of: connected capital equipment, connected devices (medical, wired, wireless, etc.), or surgical hub device (this device). The notification disappears based on notification dwell time or alert status resolution.

FIG. 40 is an image of several examples of systems notifications panel overlays 3104. The systems notifications panel overlays 3104 may include connect instrument 3112, minor error alert 3114, medium error alert 3116, and major error alert 3118, for example.

FIG. 41 is a detailed view of the device panels overlay 3106 shown in FIG. 37. The example device panels overlay 3106 shown in FIG. 41, displays information associated with a combination ultrasonic/RF instrument connected to the system 3000 (FIG. 36) to provide advanced hemostasis. The device panels overlay 3106 provide a Thermal indication and a Ready indication, for example.

In various aspects, the device panels overlay 3106 provides a visual concept influenced by the Ottava framework and may be selectively enabled/disabled via the staff console. The staff console also can selectively enable/disable individual panels such as, for example, energy and surgical stapler. In one aspect, the device panels overlay 3106 only appears if a relevant instrument is connected to the system 3000 (FIG. 36). The device panels overlay 3106 are not visible if nothing is connected to the system 3000 (FIG. 36). The space occupied by the device panels overlay 3106 is configurable (e.g., left, center, right aligned). The device panels overlay 3106 also may be configured to display connectivity to handheld instruments. In other aspects, the device panels overlay 3106 may be configurable in the space along the top/bottom of the display. The device panels overlay 3106 may display multiple instrument devices connected simultaneously. In one aspect, the device panels overlay 3106 may display information only for devices which are actively being used by the surgeon such that connected, but inactive device displays are hidden.

In one aspect, the size of the device panels overlay 3106 may be configurable based on the features that are enabled, such as the Thermal example described herein. These features may be enabled or disabled based upon intrinsic device design (e.g., future models), as well as enabled/disabled by the surgeon, or paid subscription.

Figure 42:
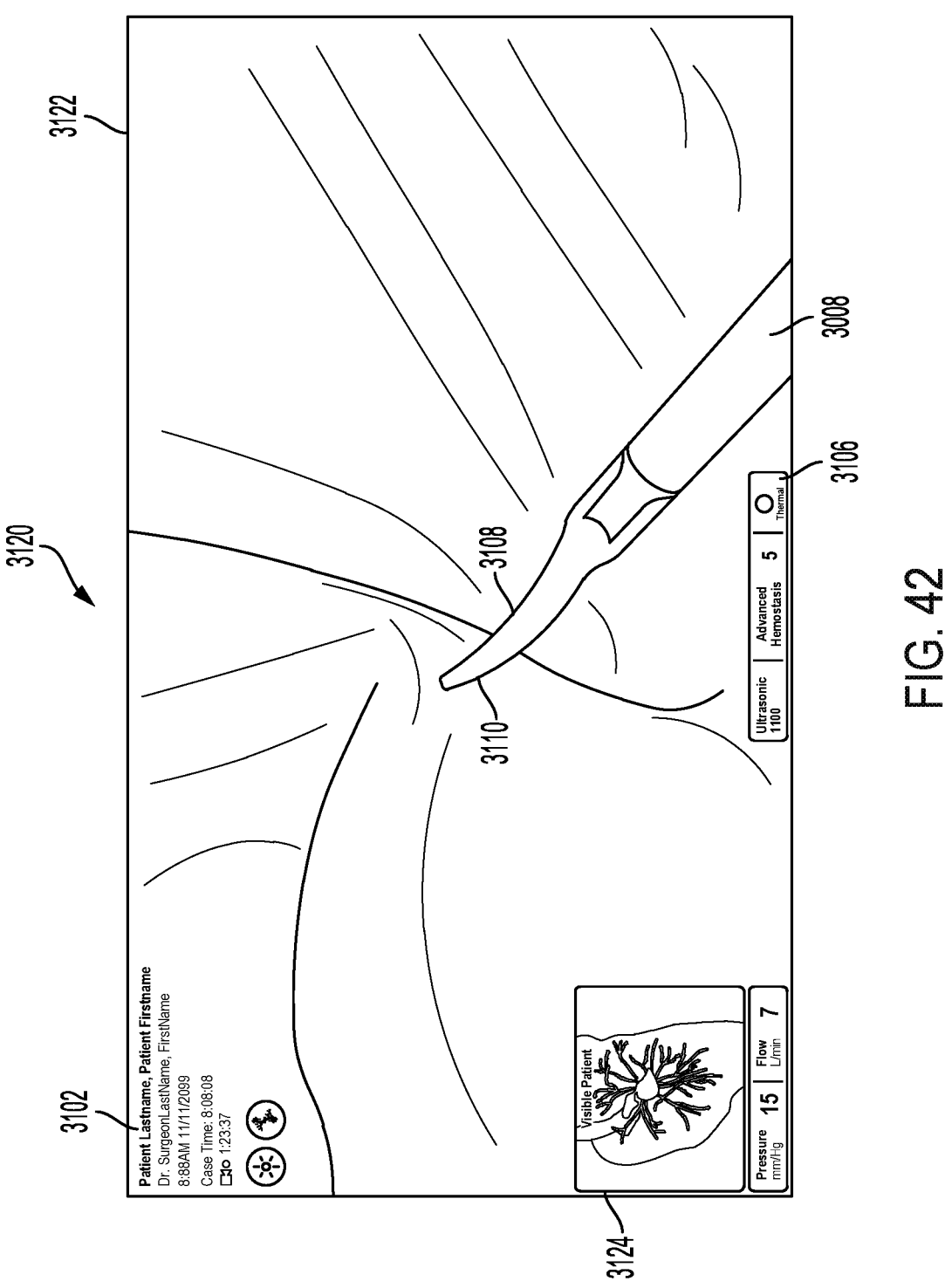
FIG. 42 is an augmented image of a live feed of a surgical area as visualized through a laparoscopic camera during a minimally invasive surgical procedure displayed on an intra-operative data display, according to one aspect of this disclosure.

FIG. 42 is an augmented image 3120 of a live feed of a surgical area as visualized through a laparoscopic camera during a minimally invasive surgical procedure displayed on an intraoperative data display 3122. showing an end effector 3108 of a surgical instrument 3008 grasping tissue 3110 and a screen with a visible patient panel overlay 3124, in accordance with at least one aspect of the present disclosure. The visible patient panel overlay 3124 may require an additional application to display content. The intraoperative data display 3122 also displays the case information panel overlay 3102 and the device panels overlay 3106. In the illustrated example, the systems notifications panel overlay 3104 is hidden.

Figure 43:
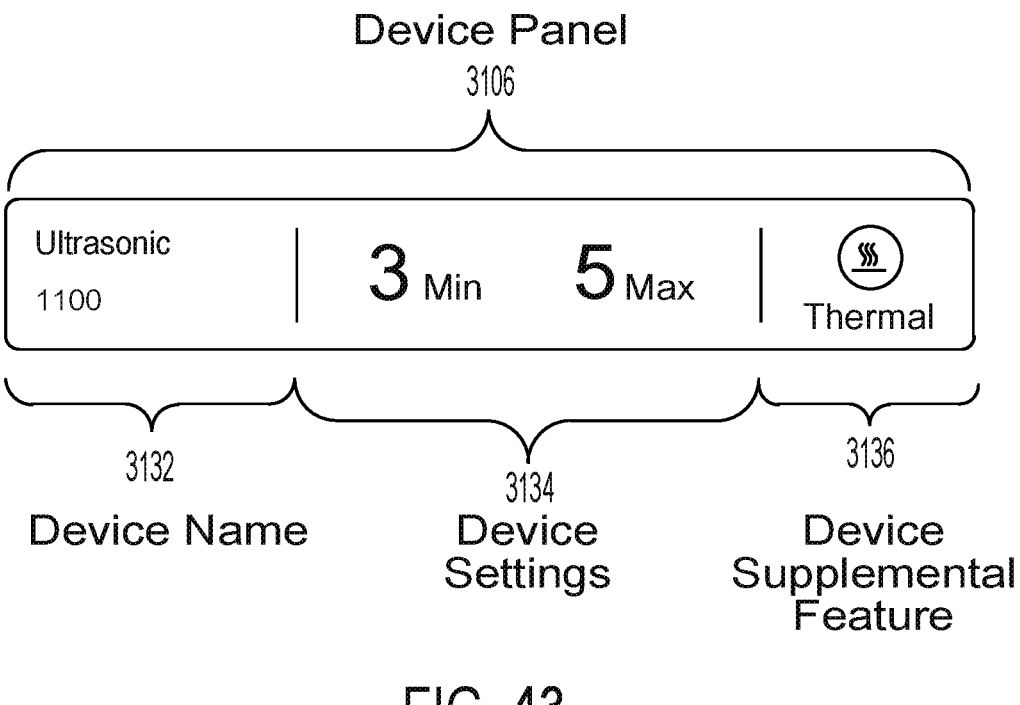
FIG. 43 is a schematic view of an energy device image panel architecture, according to one aspect of this disclosure.

FIG. 43 is a schematic view of an energy device image panel 3106 architecture. In one aspect, the energy device image panel 3106 includes a device name 3132, device settings 3134, and device supplemental features 3136, for example.

Figure 44:
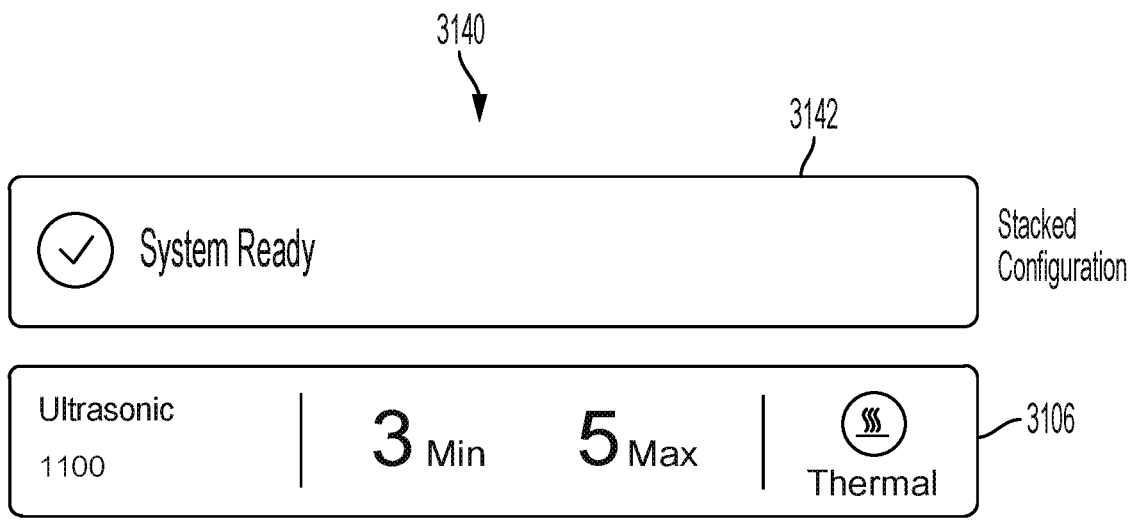
FIG. 44 is an image of supplemental device alerts/warn-ing/information in a stacked configuration, according to one aspect of this disclosure.

FIG. 44 is an image 3140 of supplemental device alerts/warning/information in a stacked configuration. The supplemental device alerts/warnings/information display may be stacked. The supplemental device alerts/warnings/information display also may be stacked vertically to cover the main device panel, or may be expanded horizontally. As shown in the example of FIG. 44, the energy device panel overlay 3106 is stacked vertically below a system ready 3142 display.

Figure 45:
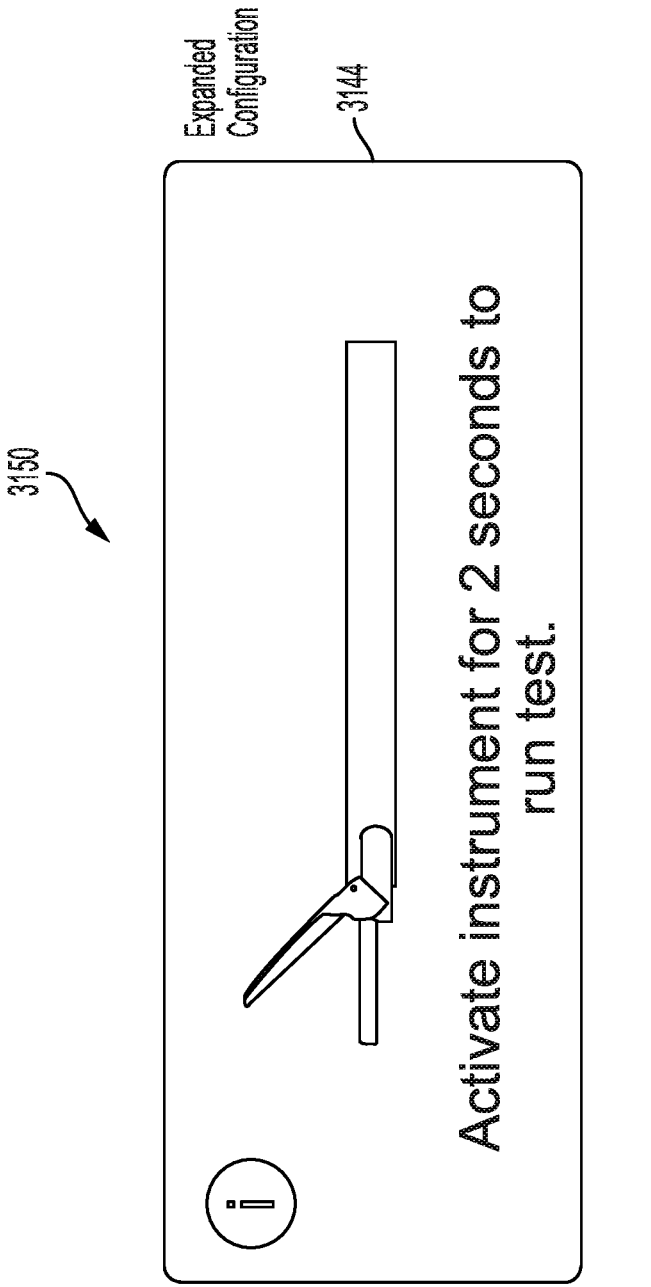
FIG. 45 is an image of supplemental device alerts/warn-ing/information in an expanded configuration, according to one aspect of this disclosure.

FIG. 45 is an image 3150 of supplemental device alerts/warning/information in an expanded configuration. The supplemental device alerts/warnings/information display may be expanded. The expanded display 3144 may be expanded vertically or horizontally. As shown in the example of FIG. 45, the expanded display 3144 provides additional information about the instrument device. As shown in the example is FIG. 45, the expanded display 3144 shows an image of a surgical instrument and the instructions to activate the instrument for 2 seconds t run test.

Figure 46:
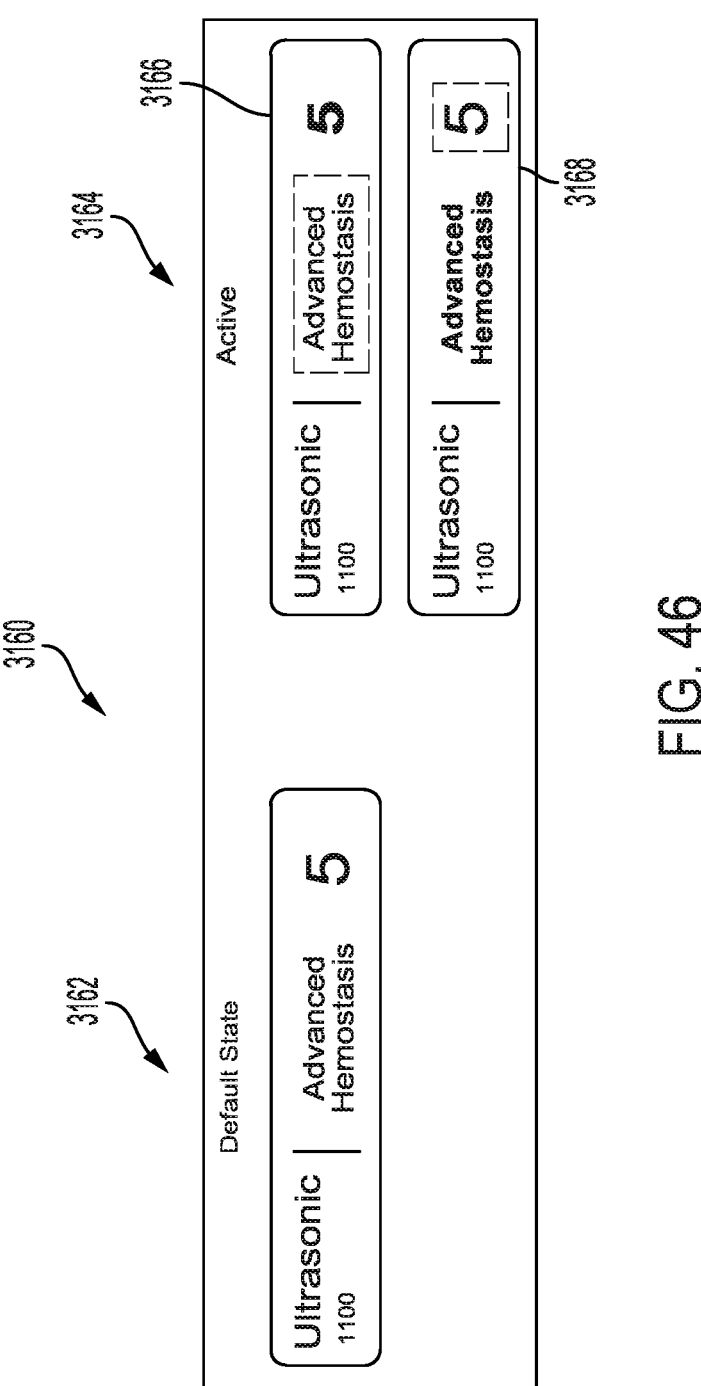
FIG. 46 is an instrument state image panel showing how instrument panel states change dynamically to show state changes such as device activation or power level adjustment, according to one aspect of this disclosure.

FIG. 46 is an instrument state image panel 3160 showing how instrument panel states change dynamically to show state changes such as device activation or power level adjustment. The left side 3162 of the instrument state image panel 3160 shows the default state of the instrument. The right side 3164 of the instrument state image panel 3160 shows the active state of the instrument. In the example shown in FIG. 46, a first panel 3166 on the right side 3164 of the instrument state image panel 3160 shows a dynamic change in the instrument activation and a second panel 3168 of the right side 3164 on the instrument state image panel 3160 shows a dynamic change in the instrument power level.

Figure 47:
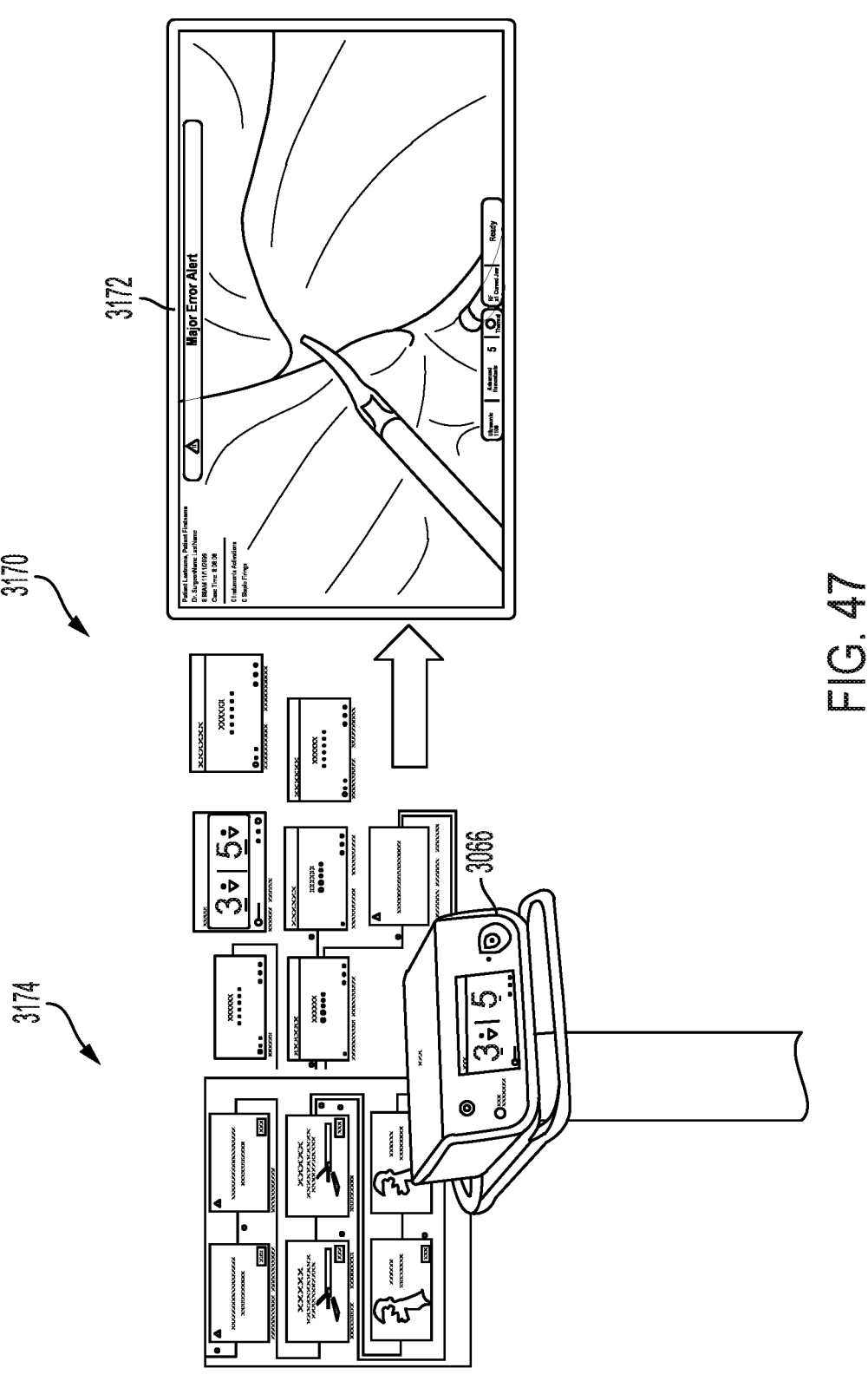
FIG. 47 is a system diagram of translating generator alerts and warnings to a laparoscopic monitor and displayed on a local interface, according to one aspect of this disclosure.

FIG. 47 is a system diagram 3170 of translating generator 3066 alerts and warnings 3174 to a laparoscopic monitor 3172 and displayed on a local interface.

Figure 48:
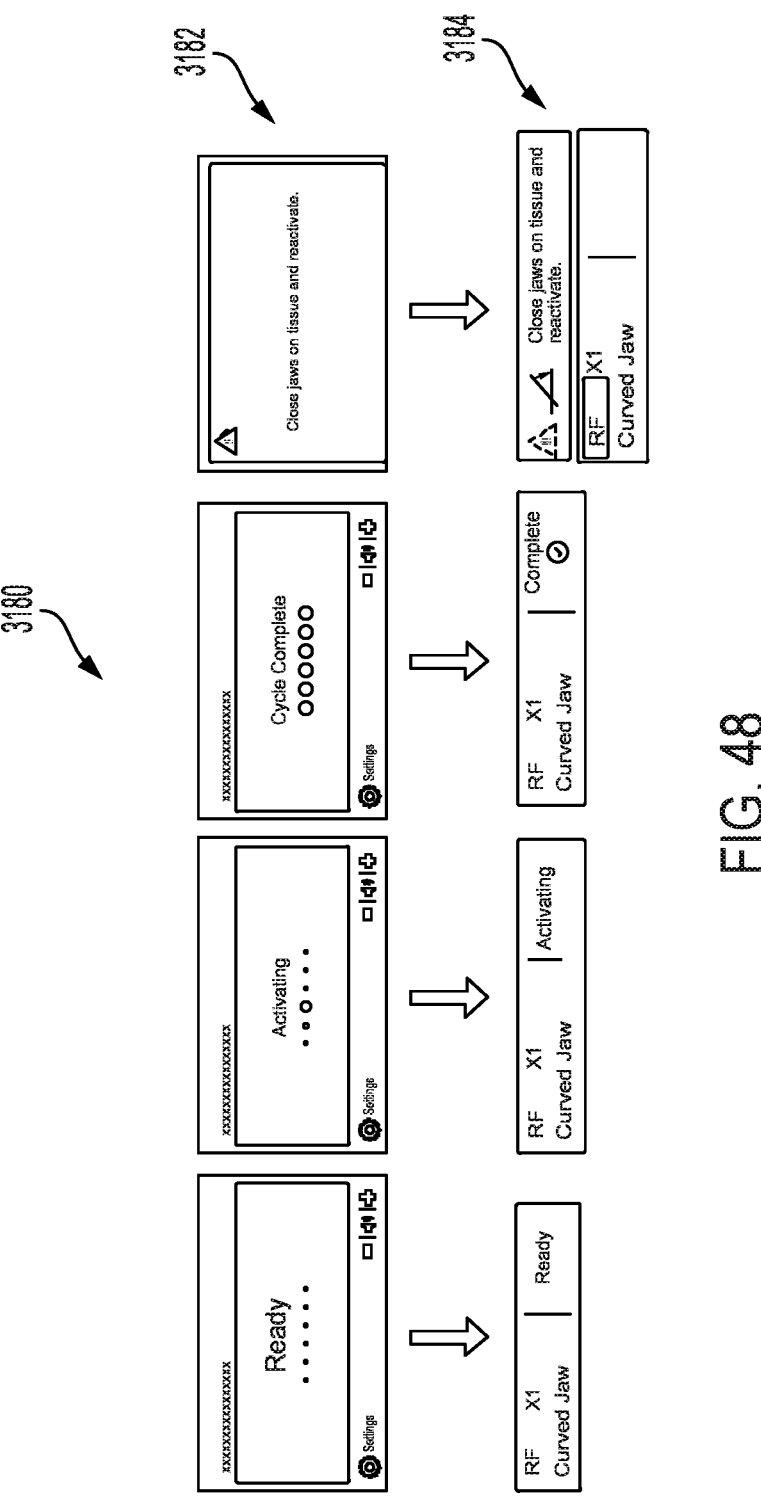
FIG. 48 is a diagram of a series of screens of existing alerts shown on a current generator that are transmitted to a surgical hub, which then displays them as a series of screens on a local interface, according to one aspect of this disclo-sure.

FIG. 48 is a diagram 3180 of a series of screens 3182 of existing alerts shown on a current generator that are transmitted to a surgical hub, which then displays them as a series of screens 3184 on a local interface.

Figure 49:
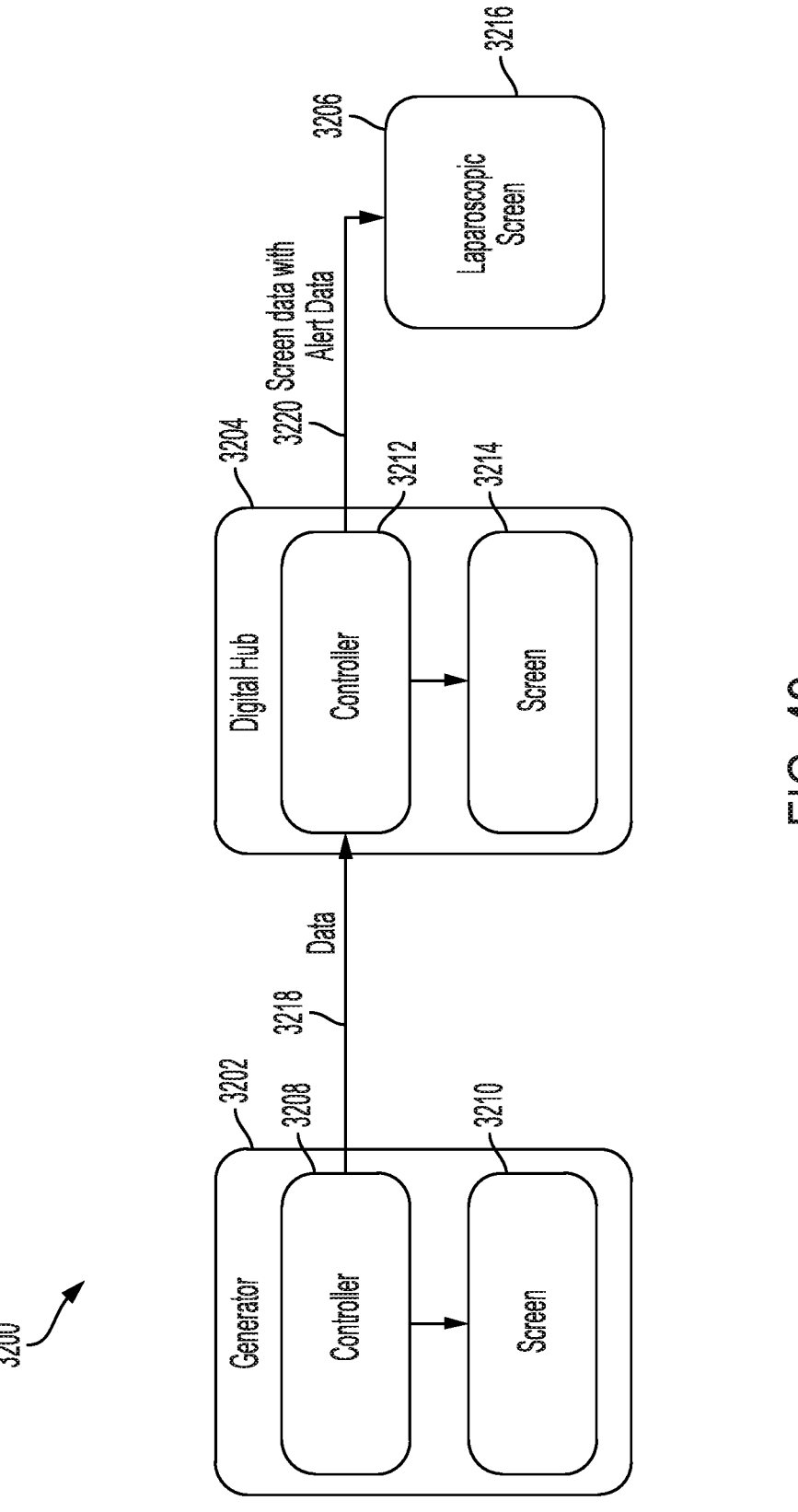
FIG. 49 is a schematic diagram of a system comprising a generator in communication with a digital hub, which then displays screen data and alert data on a local interface such as a laparoscopic screen, according to one aspect of this disclosure.

FIG. 49 is a schematic diagram of a system 3200 comprising a generator 3202 in communication with a digital hub 3204, which then displays screen data and alert data 3220 on a local interface 3206 such as a laparoscopic screen 3216. The generator 3202 comprises a controller 3208 and a screen 3210. The controller 3208 of the generator 3202 transmits data 3218 to a controller 3212 of the digital hub 3204. The digital hub 3204 also comprises a screen 3214. The controller 3212 of the digital hub 3204 transmits screen data and alert data 3220 to the laparoscopic screen 3216 of the local interface 3206.

Figure 50:
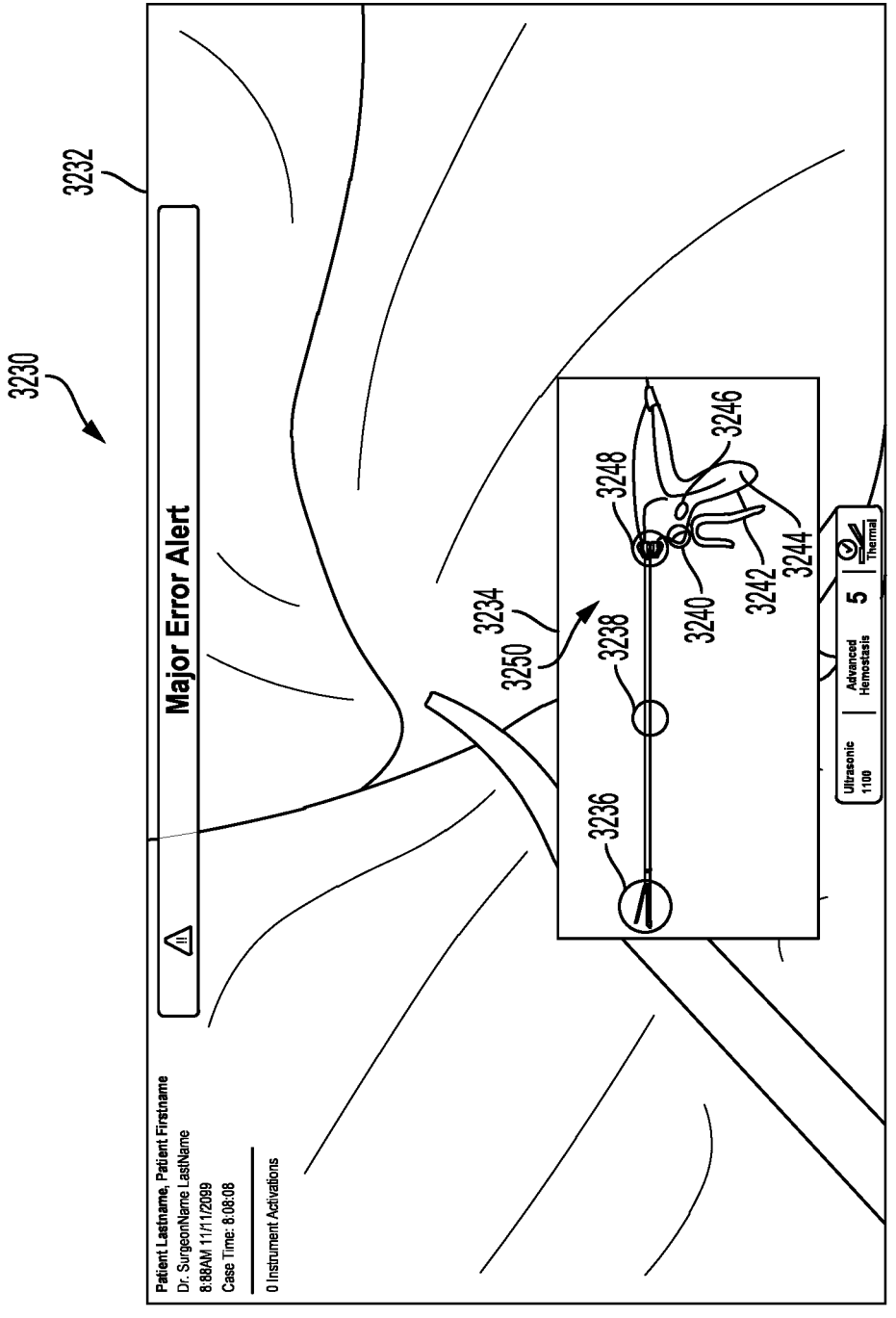
FIG. 50 is an augmented image of a live feed of a surgical area as visualized through a laparoscopic camera during a minimally invasive surgical procedure displayed on an intra-operative data display, according to one aspect of this disclosure.

FIG. 50 is an augmented image 3230 of a live feed of a surgical area as visualized through a laparoscopic camera during a minimally invasive surgical procedure displayed on an intraoperative data display 3232. The laparoscopic field of view of the surgical area shows an overlay panel 3234 depicting optimal device performance (ODP) guide images or other instructions for use (IFU)/informational sources. The augmented image 3230 shows an on-screen display overlay panel 3234 shows a surgical device 3250 comprising a grip housing 3244, trigger 3242, shaft 3238 and blade with tissue pad 3236. The shaft 3238 is rotated by a rotation nob 3248. The surgical device 3250 also includes an energy button 3240 and an energy button 3246 with advanced hemostasis.

The overlay panel 3234 displays an image of a surgical device 3250 and ODP guide images or other IFU/informational sources. The images may be presented to the surgeon with surgical device information. The images may be static or animated images. The images may provide general surgical device 3250 information (as shown), or context specific surgical device information. For example, the bailout door of a surgical device 3250 may include a sensor to detect removal. When the bailout door is removed, the on-screen display overlay panel 3234 shows an image which provides instructions on the proper usage of the bailout mechanism. By way of another example, the surgeon encounters an alert while using the ultrasonic energy mode related to a surgical device technique. The on-screen display overlay panel 3234 shows information specific to how to best use the surgical device 3250 to avoid that alert.

Figure 51:
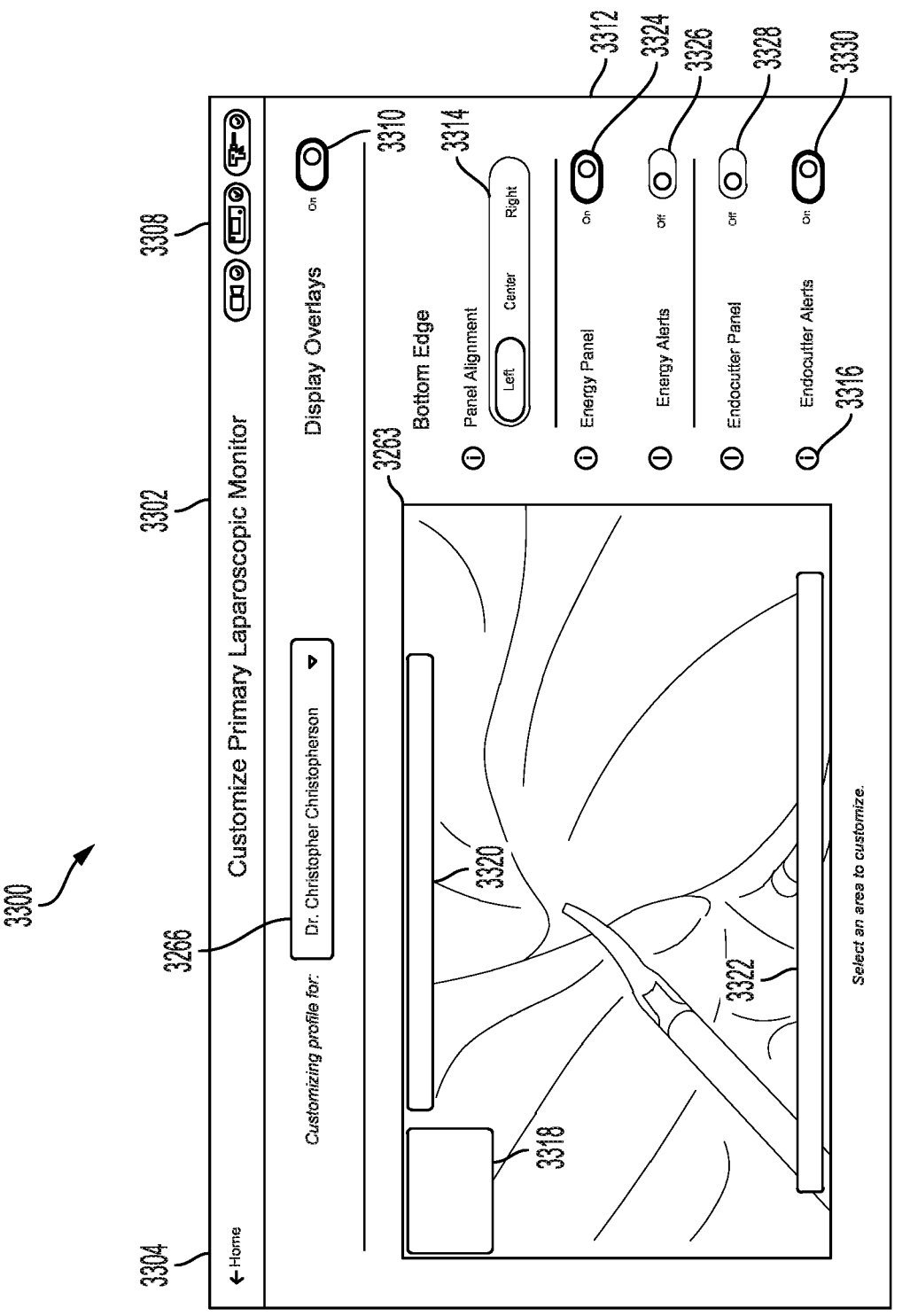
FIG. 51 is a display screen showing an intraoperative data display comprising a secondary bottom edge configurable panel, according to one aspect of this disclosure.

FIG. 51 is a display screen 3300 showing an intraoperative data display 3302 comprising a secondary bottom edge configurable panel 3312. The intraoperative data display 3302 includes a surgical field of view of a live surgical feed 3303 with customized laparoscopic overlay fields 3318, 3320, 3322 and a secondary bottom edge configurable panel 3312. The intraoperative data display 3302 displays a navigation button 3304 to return back to the home screen. The intraoperative data display 3302 also provides a selectable surgeon profile 3306. The surgeon profile preferences may be saved, recalled, or edited. The intraoperative data display 3302 also provides several connectivity status indicators 3308. Overlays associated with the intraoperative data display overlay fields 3318, 3320, 3322 may be toggled with a display overlay toggle button 3310.

The intraoperative data display 3302 also includes a secondary configurable panel that changes dynamically based on the selected customized laparoscopic overlay fields 3318, 3320, 3322 displayed in the surgical field of view of a live surgical feed 3303 area of the intraoperative data display 3302 when the display overlay toggle button 3310 is toggled in the ON position. In the example illustrated in FIG. 51, a bottom edge configurable panel 3312 is displayed by selecting the bottom edge selection field 3322 in the surgical field of view of the live surgical feed 3303 portion of the intraoperative data display 3302. Different portions of the display may be selected including, for example, a top left corner selection field 3318, a top center selection field 3320, and a bottom edge selection field 3322.

The bottom edge configurable panel 3312 includes a panel alignment bar 3314 to align the bottom edge configurable panel 3312 in the left, center, or right position, here shown in the left position. Help indicators 3316 provide contextual information to the associated toggle button 3324, 3326, 3328, 3330. The bottom edge selection field 3322 may be configured using the configurable panel alignment button 3314, which shifts the bottom edge alignment left, center, and right. In other aspects, the bottom edge selection field 3322 may be moved top and bottom, for example. In addition to the configurable panel alignment button 3314, the bottom edge configurable panel 3312 comprises a first toggle button 3324, which enables/disables the energy panel display for ultrasonic/RF energy tool devices, including alerts, here shown in the ON position. A second toggle button 3326 enables/disables display of alerts only for ultrasonic/RF energy tool devices, here shown in the OFF position. A third toggle button 3328 enables/disables display of surgical stapler tool devices, including alerts, here shown in the OFF position. A fourth toggle button 3330 enables/disables display alerts only for surgical stapler tool devices, here shown in the ON position.

Figure 52:
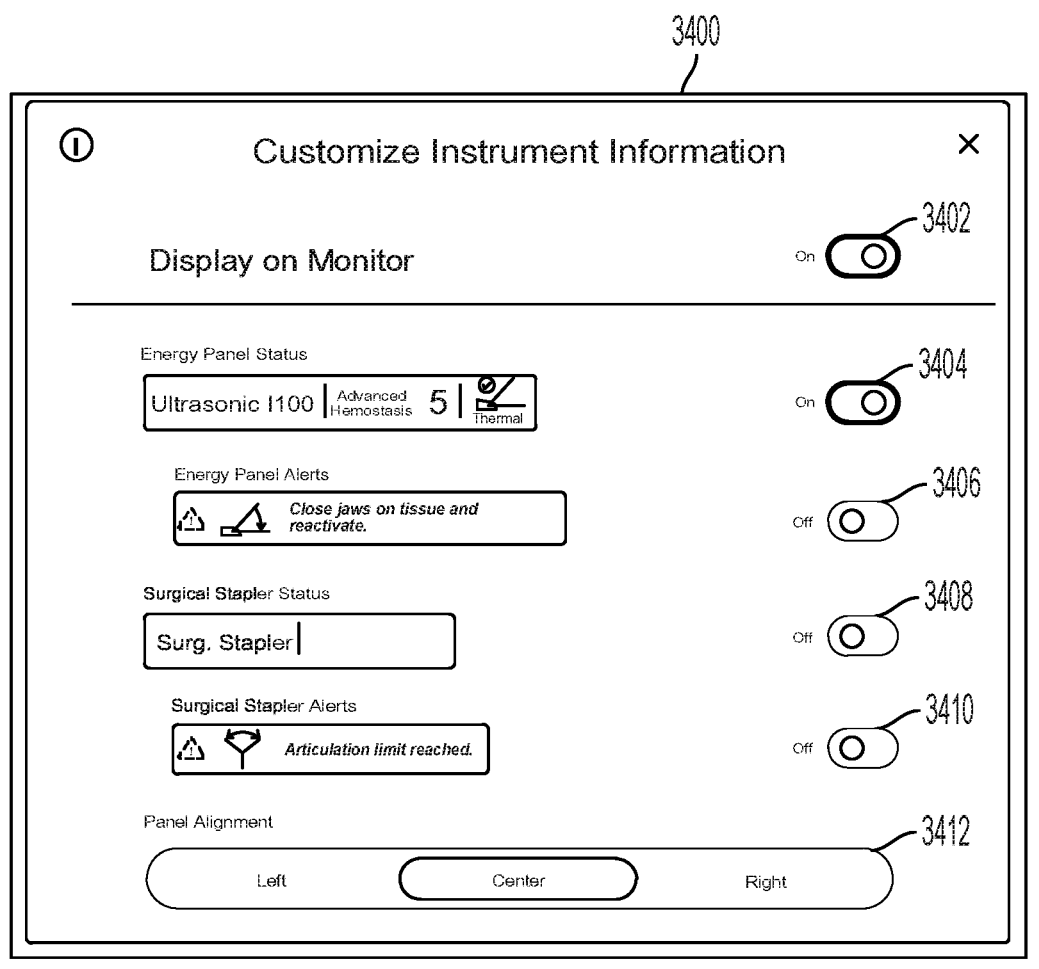
FIG. 52 is an alternative bottom edge configurable panel, according to one aspect of this disclosure.
Figure 53:
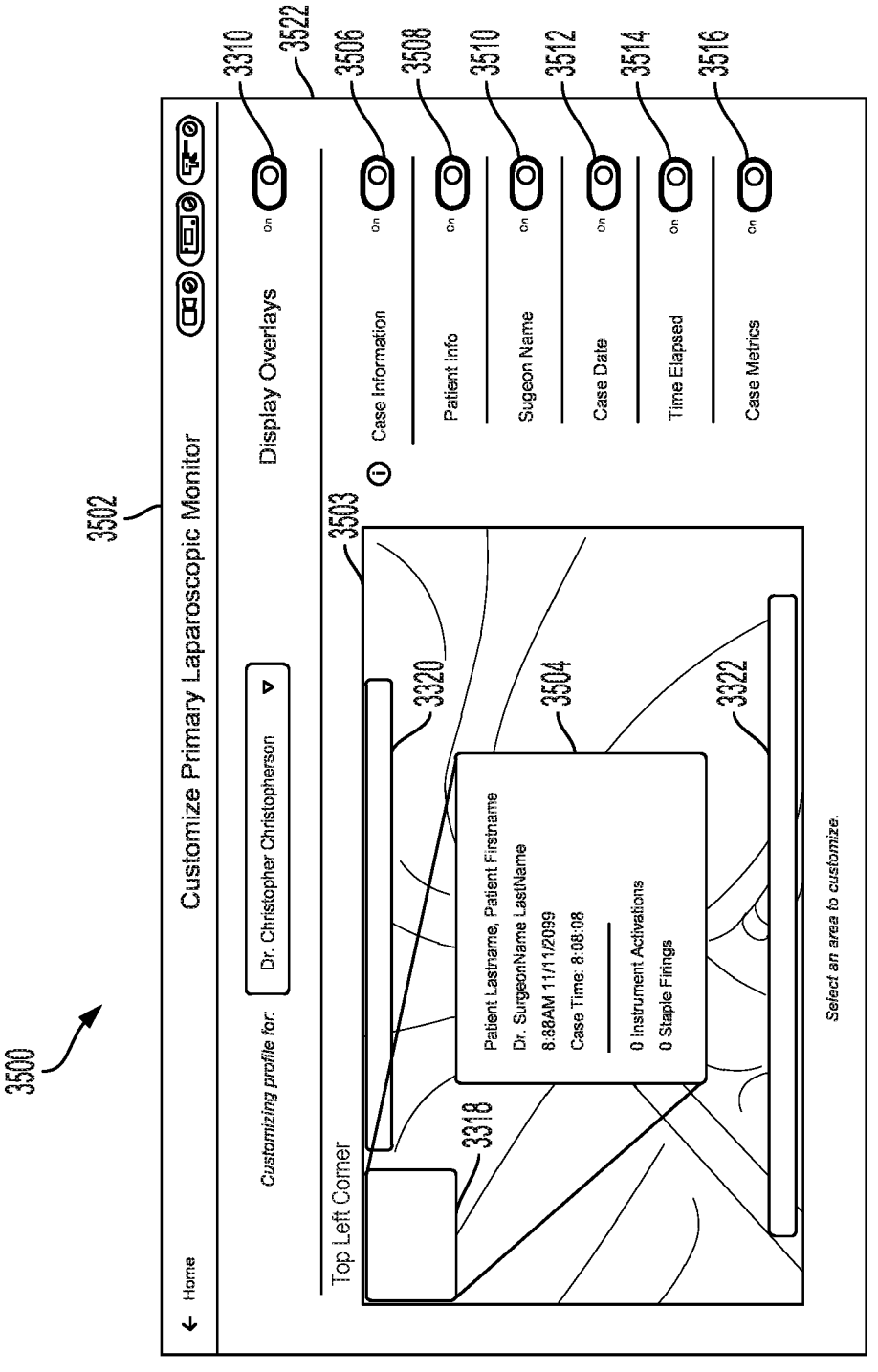
FIG. 53 is a display screen showing an intraoperative data display comprising a secondary top left corner configurable panel, according to one aspect of this disclosure.
Figure 54:
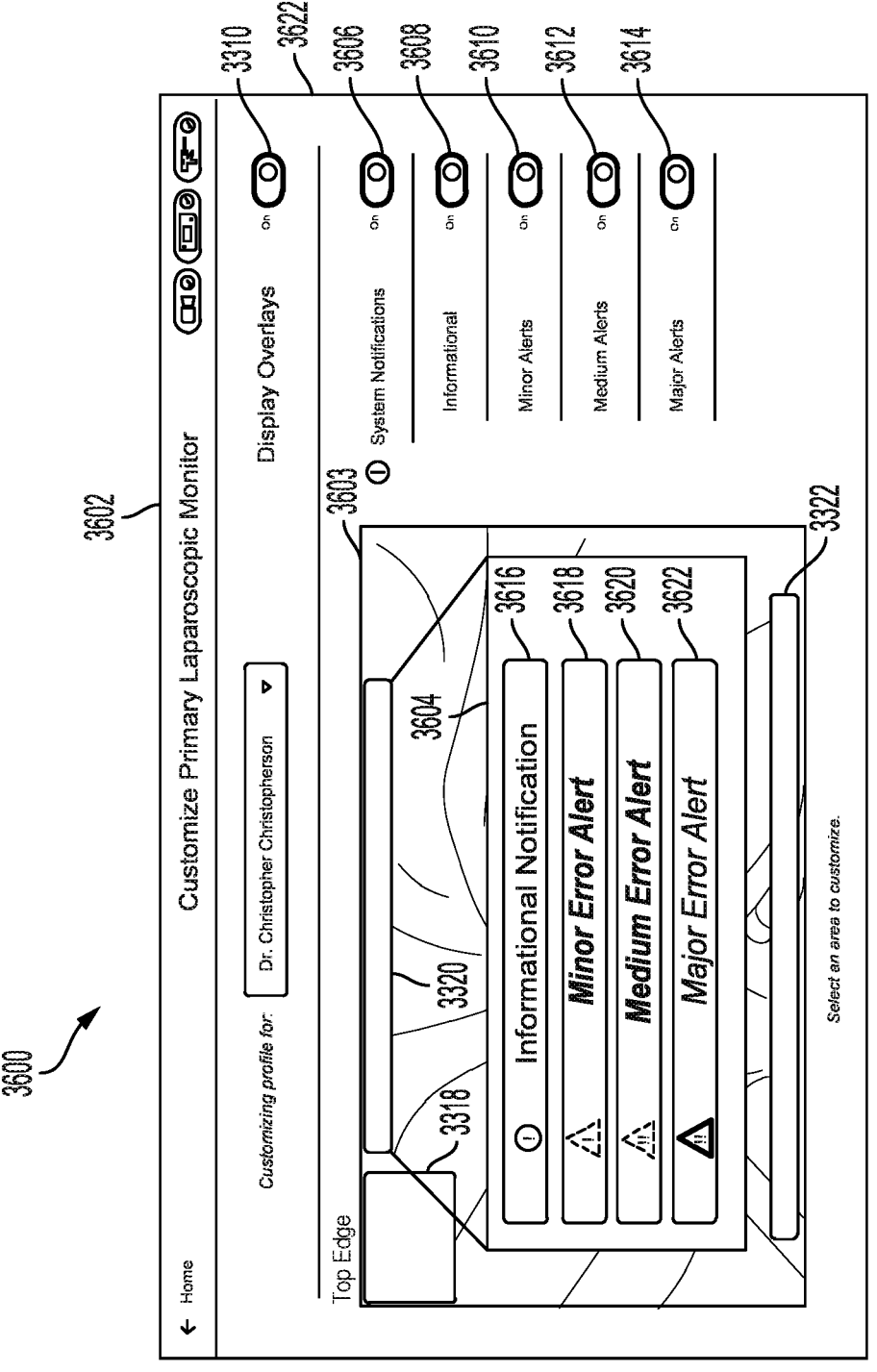
FIG. 54 is a display screen showing an intraoperative data display comprising a secondary top center configurable panel, according to one aspect of this disclosure.
Figure 55:
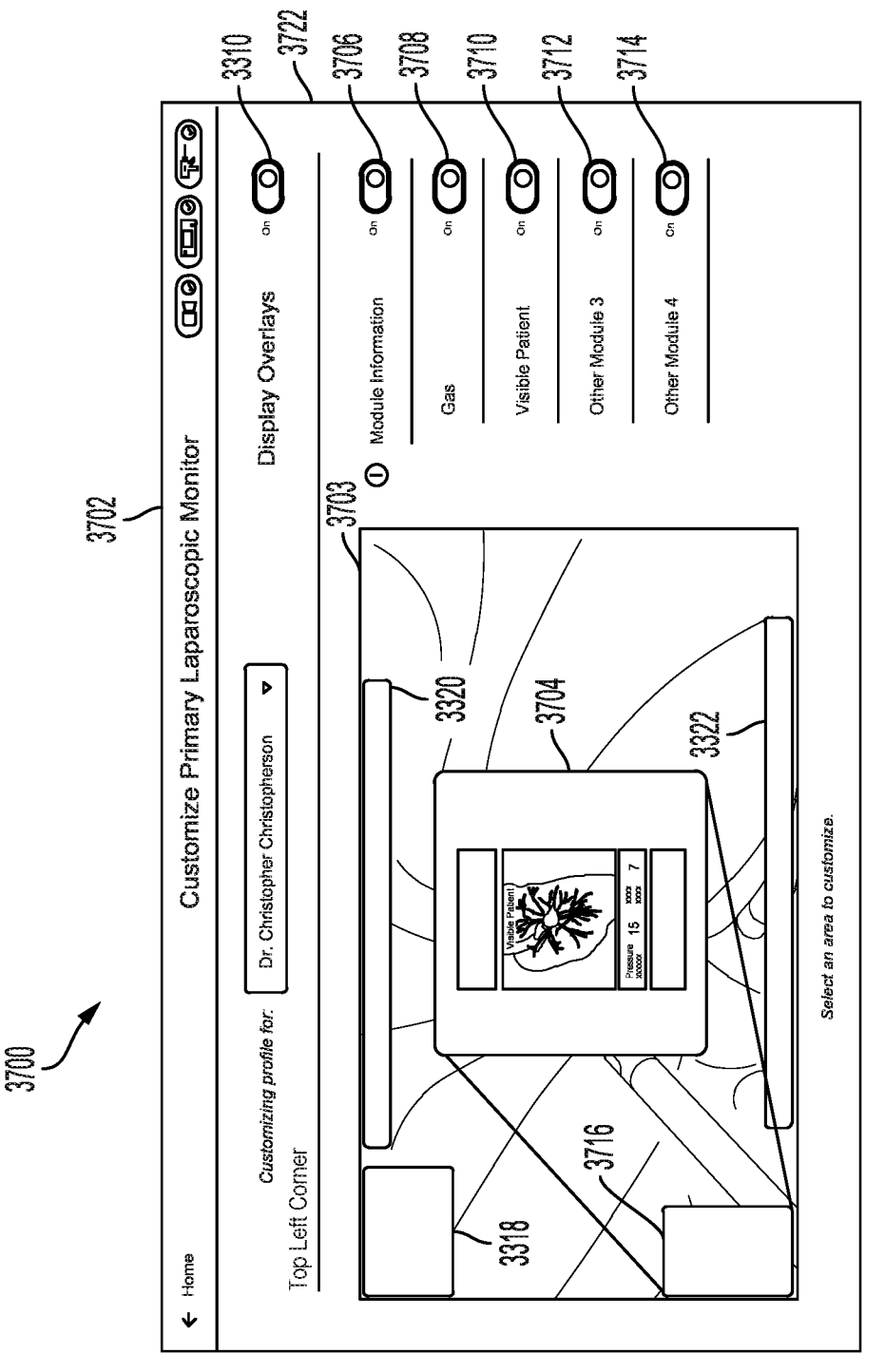
FIG. 55 is display screen showing an intraoperative data display comprising a secondary side edge configurable panel, according to one aspect of this disclosure.

FIG. 52 is an alternative bottom edge configurable panel 3400. The alternative bottom edge configurable panel 3400 is displayed by selecting the bottom edge selection field 3282 in the surgical field of view of a live surgical feed 3263 portion of the intraoperative data display 3262 in FIG. 51. The alternative bottom edge configurable panel 3400 may be configured for customization of energy status and alerts. In the illustrated example, the alternative bottom edge configurable panel 3400 is displayed by toggling the display on monitor toggle button 3402 in the ON position. A first toggle button 3404 enables/disables energy device panel status, here shown in the ON position. A second toggle button 3406 enables/disables energy device panel alerts, here shown in the OFF position. A third toggle button 3408 enables/disables surgical stapler device status, here shown in the OFF position. A fourth toggle button 3410 enables/disables surgical stapler alerts, here shown in the OFF position. The alternative bottom edge configurable panel 3400 includes a panel alignment bar 3412 to align the alternative bottom edge configurable panel 3400 in the left, center, or right position, here shown in the center position. FIGS. 53-55 described hereinbelow describe additional configurable panels displayed by selecting other selection fields in the surgical field of view of a live surgical feed portion of the intraoperative data display.

FIG. 53 is a display screen 3500 showing an intraoperative data display 3502 comprising a secondary top left corner configurable panel 3522. The intraoperative data display 3502 includes a surgical field of view of a live surgical feed 3503 with customized laparoscopic overlay fields 3318, 3320, 3322 and a secondary top left corner configurable panel 3522. The intraoperative data display 3502 includes a navigation button to return back to the home screen, a selectable surgeon profile, and connectivity status indicators as described in connection with FIG. 51. Overlays associated with the intraoperative data display overlay fields 3318, 3320, 3322 may be toggled with a display overlay toggle button 3310.

The intraoperative data display 3502 also includes a secondary configurable panel that changes dynamically based on the selected customized laparoscopic overlay fields 3318, 3320, 3322 displayed in the surgical field of view of a live surgical feed 3503 area of the intraoperative data display 3502 when the display overlay toggle button 3310 is toggled in the ON position. In the example illustrated in FIG. 53, a top left corner configurable panel 3522 is displayed by selecting the top left corner selection field 3318 in the surgical field of view of the live surgical feed 3503 portion of the intraoperative data display 3502.

Selecting the top left corner selection field 3318 dynamically changes the visual display. For example, selecting the top left corner selection field 3318, displays the case information overlay 3504, which, in this example, is the case information panel overlay screen 3102 shown in FIGS. 37 and 38. Various toggle buttons are shown alongside the right vertical portion of the secondary top left corner configurable panel 3522. As previously discussed, the display overlay toggle button 3310 enables/disables the display of the overlay screens such as the case information overlay 3504. A first toggle button 3506 enables/disables all case information from the case information overlay 3504, here shown in the ON position. A second toggle button 3508 enables/disables patient name information from the case information overlay 3504, here shown in the ON position. A third toggle button 3510 enables/disables surgeon name information from the case information overlay 3504, here shown in the ON position. A fourth toggle button 3512 enables/disables case date information from the case information overlay 3504, here shown in the ON position. A fifth toggle button 3514 enables/disables total time for the case information from the case information overlay 3504, here shown in the ON position. A sixth toggle button 3516 enables/disables case metrics, which may include total number of device activations, uses, or other device metrics, from the case information overlay 3504, here shown in the ON position.

FIG. 54 is a display screen 3600 showing an intraoperative data display 3602 comprising a secondary top center configurable panel 3622. The intraoperative data display 3602 includes a surgical field of view of a live surgical feed 3603 with customized laparoscopic overlay fields 3318, 3320, 3322 and a secondary top center configurable panel 3622. The intraoperative data display 3602 includes a navigation button to return back to the home screen, a selectable surgeon profile, and connectivity status indicators as described in connection with FIG. 51. Overlays associated with the intraoperative data display overlay fields 3318, 3320, 3322 may be toggled with a display overlay toggle button 3310.

The intraoperative data display 3602 also includes a secondary configurable panel that changes dynamically based on the selected customized laparoscopic overlay fields 3318, 3320, 3322 displayed in the surgical field of view of a live surgical feed 3603 area of the intraoperative data display 3602 when the display overlay toggle button 3310 is toggled in the ON position. In the example illustrated in FIG. 54, a top center configurable panel 3622 is displayed by selecting the top center selection field 3320 in the surgical field of view of the live surgical feed 3603 portion of the intraoperative data display 3602.

Selecting the top center selection field 3320 dynamically changes the visual display. For example, selecting the top center selection field 3320, displays the systems notifications panel overlay 3604, which, in this example, is the systems notifications panel overlay 3104 shown in FIG. 40. Various toggle buttons are shown alongside the right vertical portion of the secondary top center configurable panel 3622. As previously discussed, the display overlay toggle button 3310 enables/disables the display of the overlay screens such as the systems notifications panel overlay 3604. A first toggle button 3506 enables/disables all alerts for the systems notifications panel overlay 3604, here shown in the ON position. A second toggle button 3608 enables/disables informational alerts for the informational notification bar 3616 of the systems notifications panel overlay 3604, here shown in the ON position. A third toggle button 3610 enables/disables minor alerts for the minor error alert bar 3618 of the systems notifications panel overlay 3604, here shown in the ON position. A fourth toggle button 3612 enables/disables medium alerts for the medium error alert bar 3620 of the systems notifications panel overlay 3604, here shown in the ON position. A fifth toggle button 3614 enables/disables the major alerts for the major error alert bar 3622 of the systems notifications panel overlay 3604, here shown in the ON position. Dynamic shading of the toggle button, e.g., the fifth toggle button 3614 as shown, provides a visual cue based on the selection status.

FIG. 55 is display screen 3700 showing an intraoperative data display 3702 comprising a secondary side edge configurable panel 3722. The intraoperative data display 3702 includes a surgical field of view of a live surgical feed 3703 with customized laparoscopic overlay fields 3318, 3320, 3322, 3716 and a secondary side edge configurable panel 3722. The intraoperative data display 3702 includes a navigation button to return back to the home screen, a selectable surgeon profile, and connectivity status indicators as described in connection with FIG. 51. Overlays associated with the intraoperative data display overlay fields 3318, 3320, 3322, 3716 may be toggled with a display overlay toggle button 3310.

The intraoperative data display 3702 also includes a secondary configurable panel that changes dynamically based on the selected customized laparoscopic overlay fields 3318, 3320, 3322, 3716 displayed in the surgical field of view of a live surgical feed 3703 area of the intraoperative data display 3702 when the display overlay toggle button 3310 is toggled in the ON position. In the example illustrated in FIG. 55, a side edge configurable panel 3722 is displayed by selecting the side edge selection field 3716 in the surgical field of view of the live surgical feed 3703 portion of the intraoperative data display 3702.

Selecting the side edge selection field 3716 dynamically changes the visual display. For example, selecting the side edge selection field 3716, displays the visible patient panel overlay 3704, which, in this example, is the visible patient panel overlay 3124 shown in FIG. 42. Various toggle buttons are shown alongside the right vertical portion of the secondary side edge configurable panel 3722. As previously discussed, the display overlay toggle button 3310 enables/disables the display of the overlay screens such as the visible patient panel overlay 3704. A first toggle button 3706 enables/disables all alerts for the visible patient panel overlay 3704 information, here shown in the ON position. A second toggle button 3708 enables/disables gas information for the visible patient panel overlay 3704, here shown in the ON position. A third toggle button 3710 enables/disables visible patient information for the visible patient panel overlay 3704, here shown in the ON position. A fourth toggle button 3712 enables/disables information from another module (Module 3) for the visible patient panel overlay 3704, here shown in the ON position. A fifth toggle button 3714 enables/disables information from yet another module (Module 4) for the visible patient panel overlay 3704, shown in the ON position.

Figure 56:
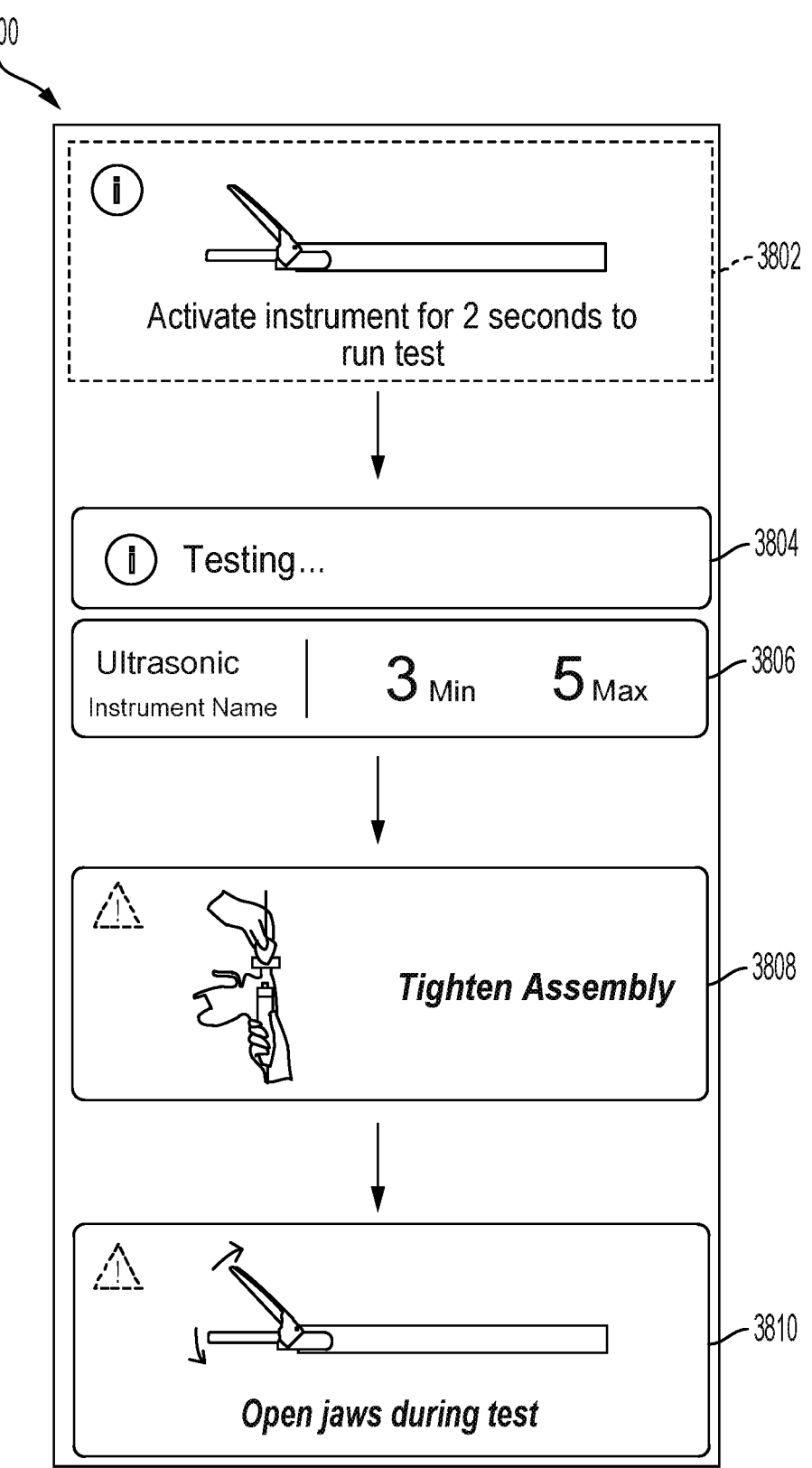
FIG. 56 is a series of image panels displaying device troubleshooting information, according to one aspect of this disclosure.

FIG. 56 is a series of image panels 3800 displaying device troubleshooting information. A first image panel 3802 displays instructions to test the instrument. In the illustrated example, the instruction to the instrument is "Activate instrument for 2 seconds to run test." A second image panel 3804 indicates that testing is in progress and a third image panels 3806 shows the testing status. A fourth image panel 3808 provides instructions for troubleshooting with static images, animations, GIFS, or videos. In the illustrated example, the image panel 3808 displays an animation to "Tighten Assembly." A fifth image panel 3810 indicates an action for the instrument under test and, in the illustrated example, informs to "Open jaws during test."

Figure 57:
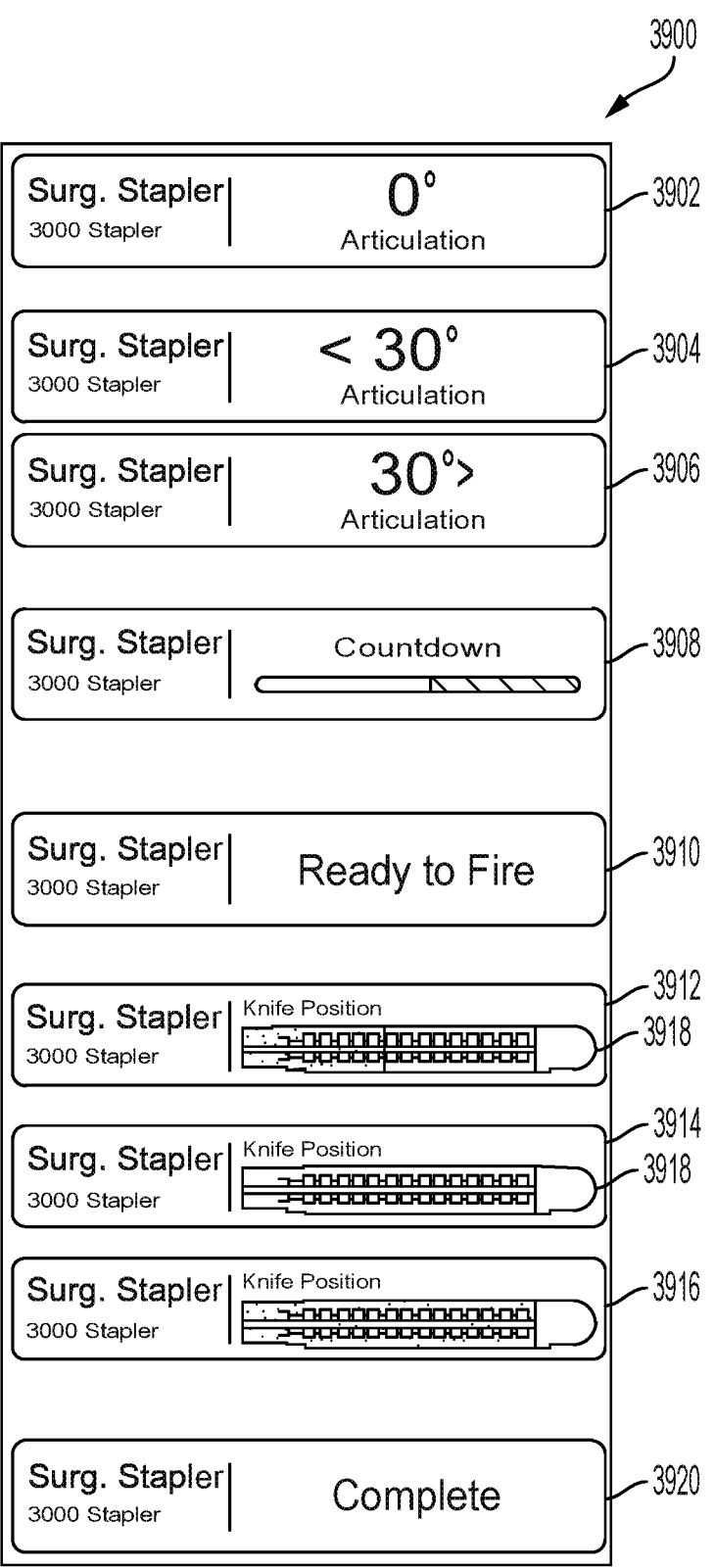
FIG. 57 is a series of image panels displaying articulating surgical stapler features, according to one aspect of this disclosure.

FIG. 57 is a series of image panels 3900 displaying articulating surgical stapler features. A first image panel 3902 indicates surgical stapler articulation angle of the surgical stapler device. The angle may be shown numerically or visually. Second and third image panels 3904, 3906 indicate articulation angle updates based on device status and also show articulation direction. In one aspect, each time the articulation button is pressed or articulation angle changes, an updated measurement is sent to the digital hub 3204 (FIG. 49), 3006 (FIG. 36). The digital hub 3204 (FIG. 49), 3006 (FIG. 36) then uses the updated measurement to update the reflected angle as shown on the image panels 3902, 3904, 3906.

A fourth image panel 3908 is a standardized countdown indicator that appears when the surgical stapler jaw is closed. The countdown dynamically changes based on time. The device may be fired any time during the countdown sequence. A fifth image panel 3910 indicates that the device is ready to fire. Sixth, seventh, and eight image panels 3912, 3914, 3916 indicate the knife position along the sled. The knife position is shown in gray over the an illustration of a cartridge 3918 and dynamically changes based on the device. An illustration of a cartridge 3918 may be generic or specific to the cartridge installed in the surgical stapler. The knife position/surgical stapler image panels 3912, 3914, 3916 may dynamically change based on the type and size of the surgical stapler wirelessly connected. A knife position algorithm executes after or as the firing trigger of the surgical stapler is depressed and as the surgical stapler begins firing, the knife and sled begin to travel down the length of the surgical stapler A ninth image panel 3920 indicates that the operation is complete.

Each of the supplemental features displayed by the corresponding image panels 3902-3920 of the connected device dynamically update based on the current status of the device.

Figure 58:
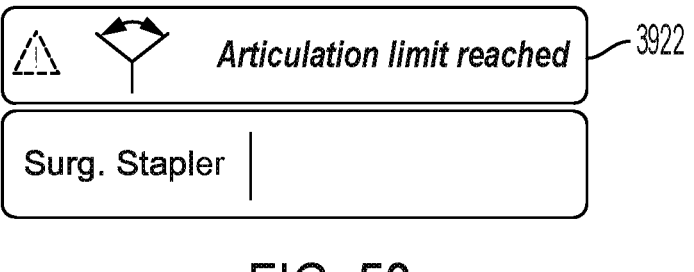
FIG. 58 is an alert/warning/information image panel displaying that the articulation limit has been reached, according to one aspect of this disclosure.

FIG. 58 is an alert/warning/information image panel 3922 displaying that the articulation limit has been reached.

Figure 59:
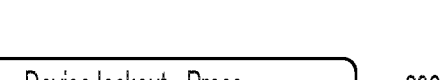
FIG. 59 is an alert/warning/information image panel displaying that the device is in lockout mode, according to one aspect of this disclosure.

FIG. 59 is an alert/warning/information image panel 3924 displaying that the device is in lockout mode.

Figure 60:
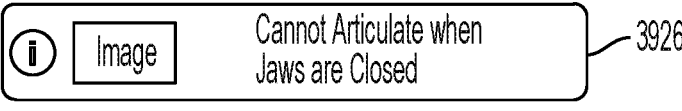
FIG. 60 is an alert/warning/information image panel displaying that the device cannot articulate when jaws are closed, according to one aspect of this disclosure.

FIG. 60 is an alert/warning/information image panel 3926 displaying that the device cannot articulate when jaws are closed.

Figure 61:
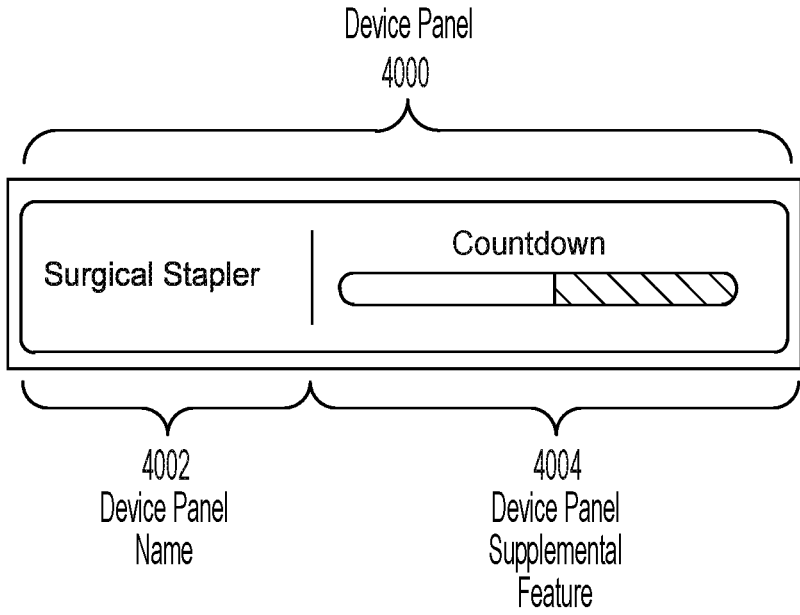
FIG. 61 is a device image panel showing articulating surgical stapler features, according to one aspect of this disclosure.

FIG. 61 is a device image panel 4000 showing articulating surgical stapler features. The device image panel 4000 includes a device panel name 4002, here shown as surgical stapler 3000, and a device panel supplemental feature 4004, here shown as the countdown indicator.

Figure 62:
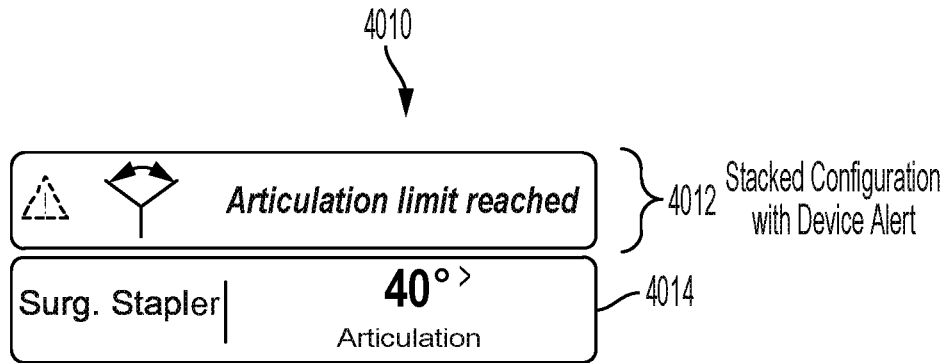
FIG. 62 is a stacked alert/warning/information image panel displayed in a stacked configuration with device alert displaying that the articulation limit has been reached, according to one aspect of this disclosure.

FIG. 62 is a stacked alert/warning/information image panel 4010 displayed in a stacked configuration with device alert displaying that the articulation limit has been reached. The stacked image panel 4010 includes a top image panel 4012 indicating that the articulation limit has been reached. The stacked image panel 4010 includes a bottom image panel 4014 that indicates the name and type of the device, articulation angle, and articulation direction.

Figure 63:
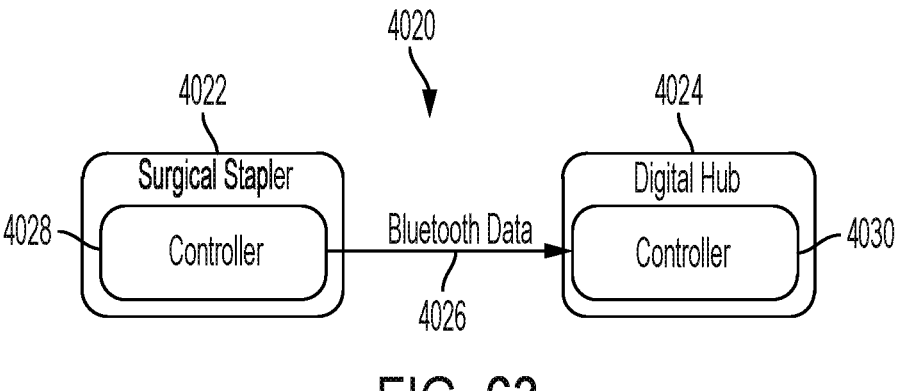
FIG. 63 is a schematic diagram of a system comprising a surgical stapler in communication with a digital hub over Bluetooth to execute an algorithm for the countdown timer image panel shown in FIGS. 57 and 61, according to one aspect of this disclosure.

FIG. 63 is a schematic diagram of a system 4020 comprising a surgical stapler in communication with a digital hub over Bluetooth to execute an algorithm for the countdown timer image panel 4000 shown in FIGS. 57 and 61. The surgical stapler 4022 is in communication with the digital hub 4024 over a wireless network, such as Bluetooth, for example. The surgical stapler comprises a controller 4028 and the digital hub 4024 comprises a controller 4030. The surgical stapler controller 4028 transmits wireless data 4026 to the digital hub controller 4030. When the surgical stapler 4022 clamps and sends a clamp status message to the digital hub 4024, the digital hub 4024 uses the clamp status message as a start command to initiate a countdown timer. If an unclamp message is received, the timer restarts to 0 and stop incrementing. If the timer reaches a set time, the timer is stopped and a flag is set.

Figure 64:
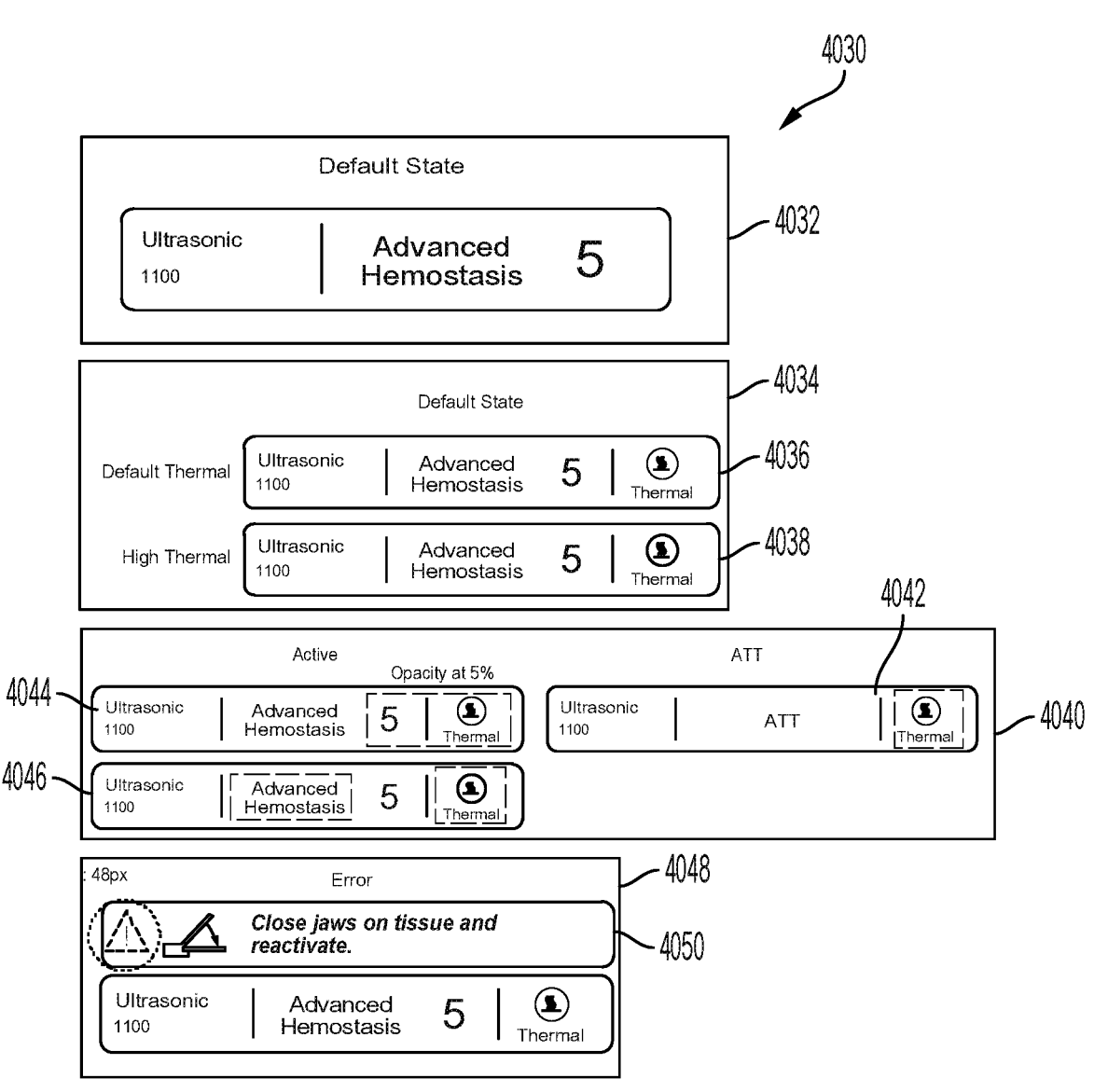
FIG. 64 is a series of device image panels/alerts display-ing ultrasonic instrument features, according to one aspect of this disclosure.

FIG. 64 is a series of device image panels/alerts 4030 displaying ultrasonic instrument features. The device image panels are expandable or collapsible depending upon the features that are enabled or disabled by the user and/or the features that are enabled or disabled by the device connected. By way of example, a first device image panel 4032 can be expanded into the second device image panel 4034, which displays a default thermal image panel 4036 and a high thermal image panel 4038. The high thermal image panel 4038 displays the status of the device temperature by direct means (temperature sensing) or indirectly via other methods (algorithm based on time or other means). With reference to the default thermal image panel 4036, the thermal algorithm may be based on device activation status and total time elapsed, as well as time elapsed since the last activation. In other implementations, the thermal algorithm may be based on device characteristics and/or status such as resonant frequency, inferred state of the device, or direct measurement. Thermal status is displayed only while the device is not currently activating. While the device is inactive, the display is grayed out. The thermal status is displayed at all times in the high thermal image panel 4038 and corresponds to the current state of the device. In the illustrated example, the device is an ultrasonic instrument.

A third device image panel 4040 changes color as the device is being used to illustrate the mode of device operation as shown by internal image panels 4042, 4044, 4046. A fourth device image panel 4048 displays instrument alerts and associated images and text for that alert as shown in the alert image panel 4050. The alert image panel 4050 may provide visual indicator for the alert. Alerts may be composed of only text, only images, or a combination of text and images.

FIG. 65 is a chart 4060 describing pairing a surgical stapler instrument. The surgical stapler pairing may be implemented as user selectable pairing, connect on powerup, connect on powerup with button press, or RFID token. For user selectable pairing, the user would start a pairing mode on the capital equipment via a touchscreen. The capital equipment would then attempt to identify all valid devices of that type within a region, and the user would simply select the devices that they would like to connect to. Broadcasting would continue even after time has elapsed. Connect on powerup pairing may enable Bluetooth radio on powerup, and may be turned off if it is not connected to the client within a predetermined time. The capital equipment constantly scans for new devices and connects to them. Connect on powerup with button press requires the Bluetooth radio to be enabled on powerup and if it is not connected to the client within a predetermined time, turn the radio off. The capital equipment has a pairing button that once pressed scans/connects to the device. In RFID token pairing, the user utilizes an RFID card, packaged with each device, as a method for scanning in the new device and pairing with the capital equipment.

Figure 66:
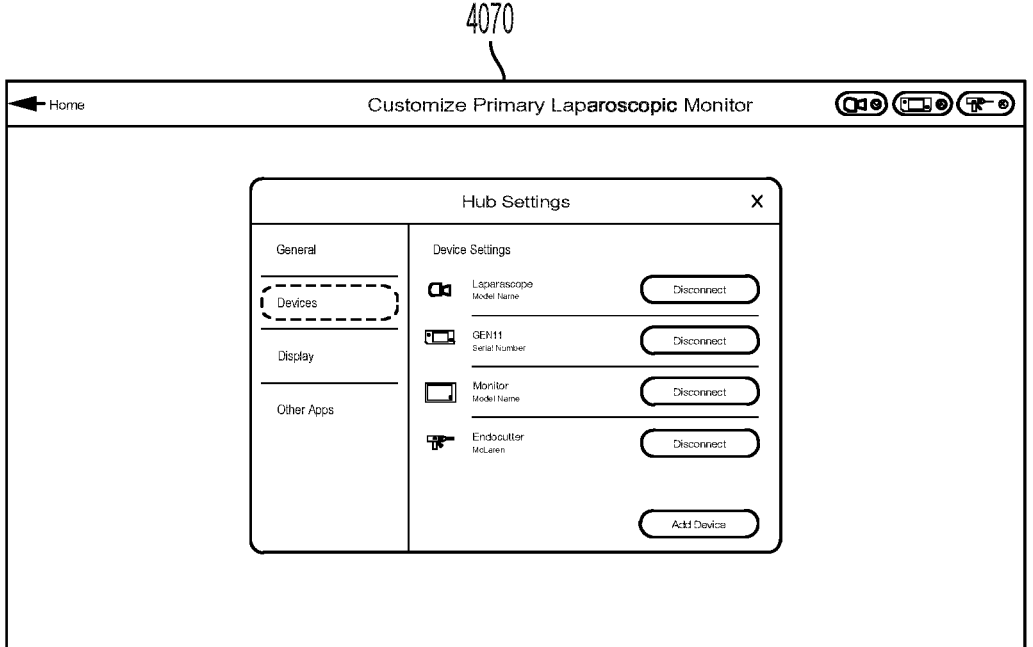
FIG. 66 is an image of a screen displaying pairing devices information, according to one aspect of this disclosure.

FIG. 66 is an image of a screen 4070 displaying pairing devices information. The screen 4070 provides system wide ability to connect/disconnect a variety of wired and wireless devices/equipment.

Figure 67:
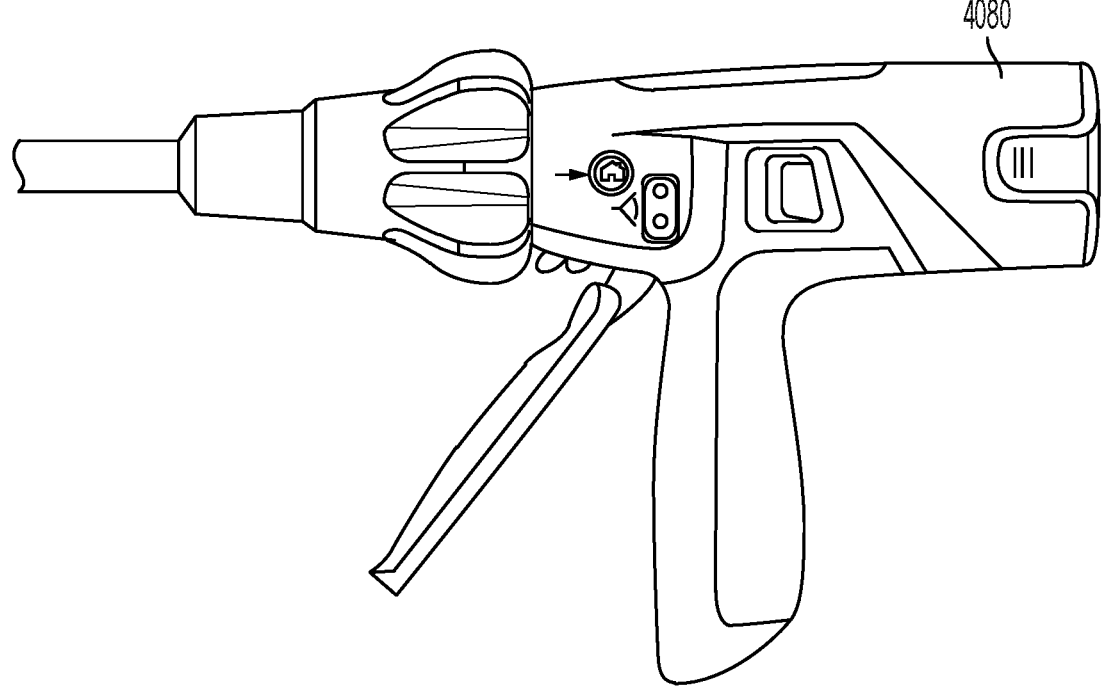
FIG. 67 is an image of a wireless surgical device com-prising a unique identifier for pairing wireless devices, according to one aspect of this disclosure.

FIG. 67 is an image of a wireless surgical device 4080 comprising a unique identifier for pairing wireless devices.

Figure 68:
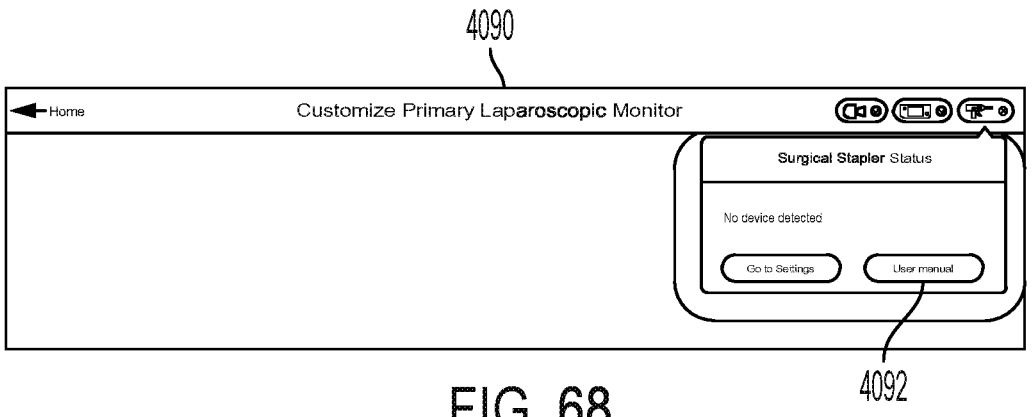
FIG. 68 is an image of a screen displaying a link to optimal device performance (ODP) guide images or other electronic instructions for use (e-IFU), according to one aspect of this disclosure.

FIG. 68 is an image of a screen 3090 displaying a link to optimal device performance (ODP) guide images or other electronic instructions for use (e-IFU). The user manual 4092 may link to e-IFU or ODP.

With reference also to FIGS. 1-68, FIG. 69 is a diagram of an augmented reality method 5000 employing a surgical instrument 77 and an augmented reality display 89 for use during a surgical procedure, according to one aspect of this disclosure. The method 5000 may be employed in conjunction with any of the augmented displays shown in FIGS. 11-48, 50-62, 64-66, and 68 and may be implemented with any of the systems shown in FIGS. 1-10, 49, and 63. In one aspect, the method 500 provides overlay of operational aspects or functions of a surgical instrument 77 onto the surgical laparoscopic video stream. The overlay may be related to the operation of one of the surgical instruments 77 being actively visualized and the overlay combines aspects of the tissue/organ interaction with functional data received from the surgical instrument 77. In another aspect, the surgical instrument 77 may be grasper or clamp and the aspect of the tissue could be incomplete capture of the tissue along with the clamp status or magnitude of the clamp. In another aspect, the surgical instrument 77 may be a surgical stapler and the aspect of the tissue may be tissue capture location or tissue compression and the aspect of the surgical stapler may be clamping or firing sufficiency, or other parameters. In another aspect, the surgical instrument 77 may be an advanced energy device and the tissue parameter may be impedance, cautery status, bleeding magnitude and the function of the surgical instrument 77 could be energy level, timing, clamp pressure, among other parameters.

In one aspect, the method 5000 is directed to overlay of data according to surgical instrument 77 utilization. According to the method 5000, an imaging device 38 captures 5002 a real image of a surgical area during a surgical procedure. A processor 85 receives 5004 functional data from the surgical instrument 77, determines 5006 an overlay related to an operational aspect of the surgical instrument 77, and combines 5008 an aspect of tissue in the surgical area with the functional data received from the surgical instrument 77. The augmented reality display 89, or local display 67, presents 5010 the overlay of the operational aspect of the surgical instrument 77 onto the real image of the surgical area. The functional data for the surgical instrument 77 may be received from the surgical instrument 77 directly or a surgical hub coupled processor or server.

Figure 70:
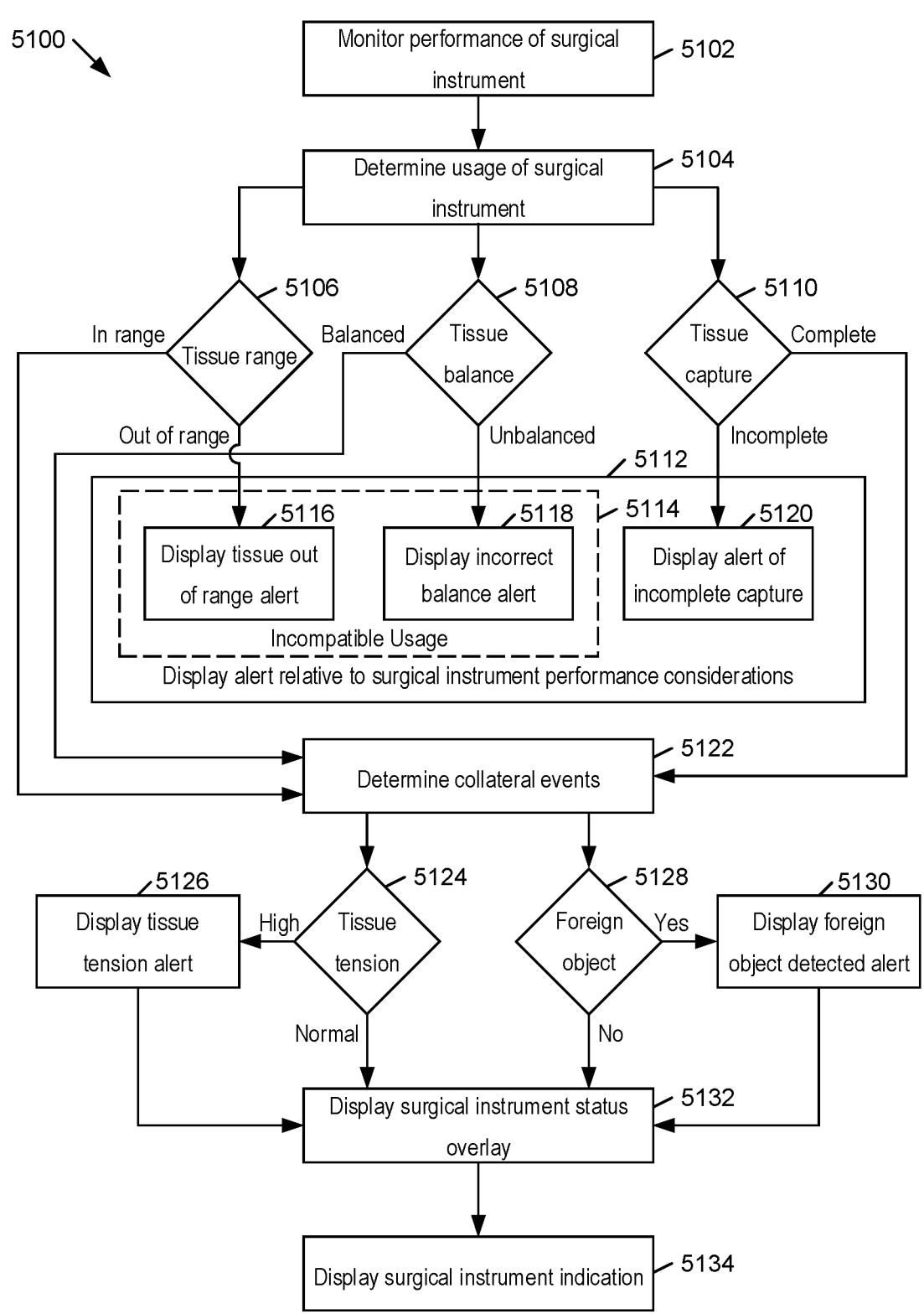
FIG. 70 is a diagram of an augmented reality method employing a surgical instrument and an augmented reality display for use during a surgical procedure, according to one aspect of this disclosure.

With reference also to FIGS. 1-68, FIG. 70 is a diagram of an augmented reality method 5100 employing a surgical instrument 77 and an augmented reality display 89 for use during a surgical procedure, according to one aspect of this disclosure. The method 5100 may be employed in conjunction with any of the augmented displays shown in FIGS. 11-48, 50-62, 64-66, and 68 and may be implemented with any of the systems shown in FIGS. 1-10, 49, and 63.

In one aspect, the method 5100 is directed to overlay of data according to surgical instrument 77 utilization. The processor 85 monitors 5102 the performance of the surgical instrument 77 during a surgical procedure. The processor 85 determines 5104 the usage of the surgical instrument 77. The augmented reality display 89 displays 5112 alerts relative to the surgical instrument 77 performance considerations. The processor 85 determines 5122 collateral events, displays 5132 a status overlay of the surgical instrument 77, and displays 5134 an indication of the surgical instruments 77 on the augmented reality display 89.

According to the method 5100, an imaging device 38 captures 5002 a real image of a surgical area during a surgical procedure. A processor 85 receives 5004 functional data for the surgical instrument 77, determines 5006 an overlay related to an operational aspect of the surgical instrument 77, and combines 5008 an aspect of tissue in the surgical area with the functional data received from the surgical instrument 77. The augmented reality display 89, or local display 67, presents 5010 the overlay of the operational aspect of the surgical instrument 77 onto the real image of the surgical area. The functional data for the surgical instrument 77 may be received from the surgical instrument 77 directly or a surgical hub coupled processor or server.

Once the processor 85 determines 5104 the usage of the surgical instrument 77, the processor 85 determines 5106 whether the tissue grasped in the jaws of the surgical instrument 77 is within a range of the jaws and determines 5108 whether the tissue is properly balanced within the jaws of the surgical instrument 77 and displays 5118 incompatible usage alerts according to the state of the usage of the surgical instrument 77. If the tissue is out of range, the processor 85 displays 5116 a tissue out of range alert on the augmented reality display 8. If the tissue is incorrectly balanced within the jaws of the surgical instrument 77, the processor 85 displays 5118 an incorrect balance alert on the augmented reality display 89. As part of determining 5104 the usage of the surgical instrument 77, the processor 85 determines if the tissue capture between the jaws of the surgical instrument 77 is complete and if not displays 5110 an alert of incomplete tissue capture.

According to the method 5100, the processor 85 determines 5122 collateral events such as tissue tension and foreign object detection. If the processor 85 determines 5124 that the tissue tension is too high, the augmented reality display 89 displays 5126 a tissue tension alert. If the processor 85 detects 5128 a foreign object in the jaws of the surgical instrument 77, the augmented reality display 89 displays 5130 a foreign object detected alert. In any case, the augmented reality display 89 displays 5132 the surgical instrument 77 status overlay according to the results of the above mentioned determinations of tissue tension and foreign object detection. Finally, the augmented reality display 89 displays 5134 the surgical instrument 77 indication.

With reference also to FIGS. 1-68, FIG. 71 is a diagram of an augmented reality method 5150 employing a surgical instrument 77 and an augmented reality display 89 for use during a surgical procedure, according to one aspect of this disclosure. The method 5100 may be employed in conjunction with any of the augmented displays shown in FIGS. 11-48, 50-62, 64-66, and 68 and may be implemented with any of the systems shown in FIGS. 1-10, 49, and 63.

In one aspect, the method 5150 is directed to a functional overlay of surgical instrument 77 critical operations or parameters to clearly represent the surgical instrument 77 (e.g., surgical the stapler, energy device) or any aspect of the interaction between the surgical stapler 77 and tissue in the surgical area. In on aspect, the overlaid data may be adjusted by an aspect detected by the surgical hub 6 to modify the overlay from the information merely detected by the source surgical instrument 77 to add context. In another aspect, the augmented displays may be further adjusted or modified by the user and as a result also result in modifications of the surgical instrument 77 being monitored during the surgical procedure.

In one aspect, the method 5150 is directed to overlay of data according to surgical instrument 77 functionality of critical operations or parameters. According to the method 5150, an imaging device 38 captures 5152 a real image of a surgical area during a surgical procedure. A processor 85 receives 5154 functional data from the surgical instrument 77, determines 5156 an overlay related to a functional aspect of the surgical instrument 77, and combines 5158 an aspect of tissue in the surgical area with the functional data received from the surgical instrument 77. The augmented reality display 89, or local display 67, presents 5160 the overlay of the functional aspect of the surgical instrument 77 or an aspect of the interaction of the surgical instruments 77 with the tissue onto the real image of the surgical area. The functional data for the surgical instrument 77 may be received from the surgical instrument 77 directly or a surgical hub coupled processor or server. In one aspect, the processor 85 may modify 5162 the overlaid data by an aspect detected by a surgical hub to provide context regarding the surgical procedure. In another aspect, the processor 85 may modify 5164 the function of the surgical instrument based on the user modification 5162.

In accordance with the methods 5000, 5100, 5150 shown in FIGS. 69-71, the processor configures the data overlay to be displayed by the augmented reality display 89 as shown in FIGS. 36-68 above. Also, the augmented reality display 89 displays the dynamic status of the surgical instrument 77 function as shown in FIGS. 36-68.

With reference to FIGS. 1-71 above, the disclosure now turns to a description of a visual overlay of data specific to conditions or instruments used that need data feed to the user for context. Adaptation and adjustability of overlaid instrument information includes functional overlay of instrument critical operations or parameters to clearly represent a surgical stapler, energy device, or aspects of its interaction. In one aspect, the overlaid data is adjusted by an aspect detected by the surgical hub to modify the overlay from the information merely detected by the source instrument to add context. In another aspect, the displays may be adjusted or modified by the user and as a result also result in modifications of the instrument being monitored operation. The visual overlay provides information associated with procedural step or plan interaction, calculated or processed feedback or forecasting, adjustments of the visual overlay based on detected parameters, control of the overlay of the data onto a surgical site visualization stream including options for controlling location, size, placement, and coupling to moving objects within the field of view, and an overview visual overlay of instruments within the filed of view of the overlying device (i.e., AR device, AR glasses, etc.).

In one aspect, the visual overlay includes a procedural step or plan interaction according to one aspect of this disclosure includes utilization of the visual overlay onto the AR device 66 such as AR glasses or other augmented screen or local display 67 to display next or missing elements for the next procedural step based on the system's situational awareness as described in FIG. 76 below. The visual overlay provides highlights for surgeons. The visual overlay also provides highlighting for OR nurses or other staff. Virtual instrument templates for OR set up and the use of AR devices 66 such as AR glasses with AR device cameras 79 for scanning and introduction and removal of product. The visual overlay also highlights product that is necessary for the next surgical step and the way an instrument was handed to a nurse for reloading. The AR device 66 looks at the status of the current procedure with the next logical cartridge for use based on the procedure and understanding of the situational awareness and identifies and highlights it within the field of vision of the user.

Additional aspects of procedural step or plan interactions are described in U.S. patent application Ser. No. 16/729,740, filed Dec. 30, 2019, titled Visualization System Quantitative Data Overlaid With Data From At Least One Instrument Function Of A Powered Instrument In Communication With The System, which is incorporated herein by reference in its entirety. In particular reference is made to FIGS. 24, 25A-B, 30, 32A-D, 34, 35, and 36A-C and associated description, for example. Additional examples may be found in U.S. Pat. No. 9,788,907B1, filed Apr. 24, 2017, titled Automated Provision Of Real-Time Custom Procedural Surgical Guidance; US20190279524A1, filed Mar. 6, 2019, titled Techniques For Virtualized Tool Interaction; U.S. Ser. No. 10/758,309B1, filed Jul. 15, 2019, titled Methods And Systems For Using Computer-Vision To Enhance Surgical Tool Control During Surgeries; U.S. Ser. No. 10/729,502B1, filed Feb. 21, 2019, titled Intraoperative Surgical Event Summary; each of which is herein incorporated by reference in its entirety.

The visual overlay includes a calculated, processed feedback, or forecasting technique according to one aspect of this disclosure. In one aspect, the visual overlay includes projecting the path of the surgical instrument 77. For example, endoscopic assisted overlay to laparoscopic view and overlay laparoscopic to endoscopic view. Another aspect includes projecting the position of a robotic arm.

In one aspect, the calculated, processed feedback, or forecasting technique provides a separate visual overlay to an assistant at bedside of the manual motion needed for assistance in a robotic case. This may include providing a separate visual overlay to assist liver retractor repositioning needs, micromanipulator portion of manual handles up down or left right, or stapler position of manual handles up down or left right.

In one aspect, the calculated, processed feedback, or forecasting technique provides a projected overlay of a surgical stapler. For example, the system may provide a projected cut line overlay, a firing delay countdown timer, force on the knife, or forecast the articulation angle. The projected cut line overlay may include path overlay, cut length overlay, or staple cartridge length.

In one aspect, the calculated, processed feedback, or forecasting technique provides a projected overlay of an energy device. The projected overlay of the energy device may include impedance calculations, straight jaw or curved jaw, or forecast articulation angle. Additional aspects, include providing an overlay of a surgical stapler countdown timer and impedance calculations.

Additional examples of calculated, processed feedback, or forecasting techniques may be found in US20200237452A1 filed Feb. 20, 2020, titled Timeline Overlay On Surgical Video; US20200268469A1 filed Feb. 27, 2020, titled Image-Based System For Estimating Surgical Contact Force; US20200268472A1 filed Feb. 27, 2020, titled Estimating A Source And Extent Of Fluid Leakage During Surgery; US20190201102A1 field Nov. 6, 2018, titled Hub Recommendations From Real Time Analysis Of Procedure Variables Against A Baseline Highlighting Differences From The Optimal Solution (in particular FIGS. 17-19 and associated description); and U.S. Ser. No. 10/878, 966B2 filed Aug. 13, 2018, titled System And Method For Analysis And Presentation Of Surgical Procedure Videos; each of which is herein incorporated by reference in its entirety.

In one aspect, the visual overlay provides a method for adjusting the visual overlay based on detected parameters. One method for adjusting the visual overlay based on detected parameters includes detecting an aspect of a procedure or instrument to trigger adaptations of the data overlaid. One aspect provides an algorithm for aligning the optical axis of the camera to the orientation of the instrument. The algorithm may include automating angle change based on surgical task.

Another method for adjusting the visual overlay based on detected parameters includes an algorithm for compensating the AR depth. In one aspect, the algorithm includes adjusting a superimposed image by monitoring the surgeon 73 focus to auto adjust the depth of the augmented information. The algorithm also may include adjusting the focus, depth, or zoom by adjusting the missing elements algorithmically. The algorithm also may include using a structured light surface 3D model to augment onto.

Another method for adjusting the visual overlay based on detected parameters includes displaying base information when a device is active or connected. For all devices, the display may include device name, device manufacturer, device status such as, for example, ready or faulted. For surgical stapler devices, the display may include cartridge installation status or cartridge firing status. For energy devices, the display my include energy settings such as power level settings, mode of operation such as advanced hemostasis, minimum power, maximum power, and current mode of operation being used.

Another method for adjusting the visual overlay based on detected parameters includes an algorithm for handling alerts that appear in portions of the display screen that are out of focus. In one aspect, the algorithm includes adjusting the focus or resolution of the portion of the display where the alert is occurring even if it is outside the direct in-situ portion. In the case of tissue tension issues that are detected during colon mobilization, for example, macro tissue tension is due to pulling on the colon causing the detected tension to occur away from the in-situ interaction visualization of the laparoscope. The tension indication may create an adjustment in the focus, clarity, or breadth of the view or it could indicate in which direction the event is occurring outside of the field currently being viewed.

Another method for adjusting the visual overlay based on detected parameters includes an algorithm for overlaying information that has not been adjusted or modified. The information may include device name and serial number. The overlaid information may be in the form of static or dynamic data.

Another method for adjusting the visual overlay based on detected parameters includes an algorithm to enhance instrument performance by requiring more focus in the short term to ensure a complete task. For example, while a surgical stapler is cutting through thick tissue. Cutting through thick tissue causes the surgical stapler to slow down. The system detects this slow down and adjusts the overlay to highlight the surgical stapler, specifically, the knife location and the knife speed. This highlighting is to pull the surgeon's focus to the surgical stapler. The surgeon may determine that with the current circumstances, a cutting pause is the best course of action.

Another method for adjusting the visual overlay based on detected parameters includes an algorithm to improve the view when smoke fills the peritoneal cavity making the view from the laparoscopic camera difficult to see. The algorithm may include overlaying an infrared view while smoke is clouding the image.

In one aspect, the visual overlay provides a method for controlling the visual overlay of data onto a surgical site visualization stream. The method includes options for controlling location, size, placement, and coupling to moving objects within the field of view. The visual display also provides adaptability of aspects of the overlaid data to enable customization of the overlay.

One method for controlling the visual overlay of data onto a surgical site visualization stream includes a Simultaneous Localization and Mapping (SLAM) technique. The SLAM technique provides a framework for building a map of unknown location and unknown environment and determining an actual position within the map. The SLAM technique localizes sensors with surroundings (sensor signal processing) and maps environment structure (pose-graph optimization). Sensors provide a digital map of unknown environment and optimize the digital map based on continuous input of data and optimization of data as the wearer moves around the space.

A visual SLAM acquires images from cameras/images sensors using sparse and dense methods. A sparse method matches feature points. A dense method controls the brightness of images.

A light detection and ranging (LiDAR) SLAM employs a laser/distance sensor and is more precise and faster than a visual SLAM but not as detailed. Matching point clouds provide an iterative closest point and normal distributions transform. For example, Google's driverless cars uses LiDAR to acquire information on its local surroundings and (coupled with Google map information) makes determinations on driving based on mapping of surroundings.

A fused method adds in other data sources such as inertial measurement unit (IMU), global positioning system (GPS), etc. In accordance with a fused method, additional known information and mapping can be overlaid with the created mapping to provide additional information to the wearer.

One method for controlling the visual overlay of data onto a surgical site visualization stream includes controlling an overlay through a dedicated device. A single function device may be configured to provide dedicated control of the overlay (and only the overlay). As shown in FIG. 36, a touchscreen interface may be employed to control features of the display.

One method for controlling the visual overlay of data onto a surgical site visualization stream includes controlling an overlay through a multifunction device. A multifunctional device may be configured to support multiple different applications or functions that, in addition, enable control of the display.

One method for controlling the visual overlay of data onto a surgical site visualization stream includes controlling specific features within an overlay. One example includes controlling overlay transparency. Another example includes controlling overlay size to enable the clinical user to change the size of the images or elements that may be overlaid onto the screen to accommodate user preferences. Another example includes controlling font size to enable the clinical user to change the size of any text that may be overlaid onto the display to accommodate user preferences. Another example includes contextual control features. This method includes employing a configurable panel that changes dynamically based on the selected area of a window on the display. Another example includes controlling alerts and warnings. This method employs buttons to select the alignment and location of where the alerts and warnings may be presented as shown in FIG. 50. Additional features include information and case metrics that may be controlled within the overlay.

One method for controlling the visual overlay of data onto a surgical site visualization stream includes controlling elements of an overlay to provide contextualized help. The overlay includes user selected buttons and automatic prompting based on user actions. This may be helpful when a user incorrectly attempts to select a feature.

One method for controlling the visual overlay of data onto a surgical site visualization stream includes controlling and interacting with the overlay from surgeon audio commands. The surgeon may call out the desired visual overlay to be overlaid onto the main display monitor. For example, the surgeon may call out a command such "patient vitals overlay," "surgical stapler overlay," or "ultrasonic overlay" to cause these overlays to be overlaid onto the main display. In one aspect, the system may employ personal tracking aspects to distinguish between the different users in the operating room.

In one aspect, the visual overlay provides a method for providing an overview visual overlay of instruments within the filed of the overlaying device such as the AR device 66, for example. The visual overlay may be configured to provide an overview status of the devices, main configurations or users, and identification of devices to the user. The visual overlay also may be configured to provide intractable controls of the overview data that enables interactive setup of the device or reconfiguration.

Figure 72:
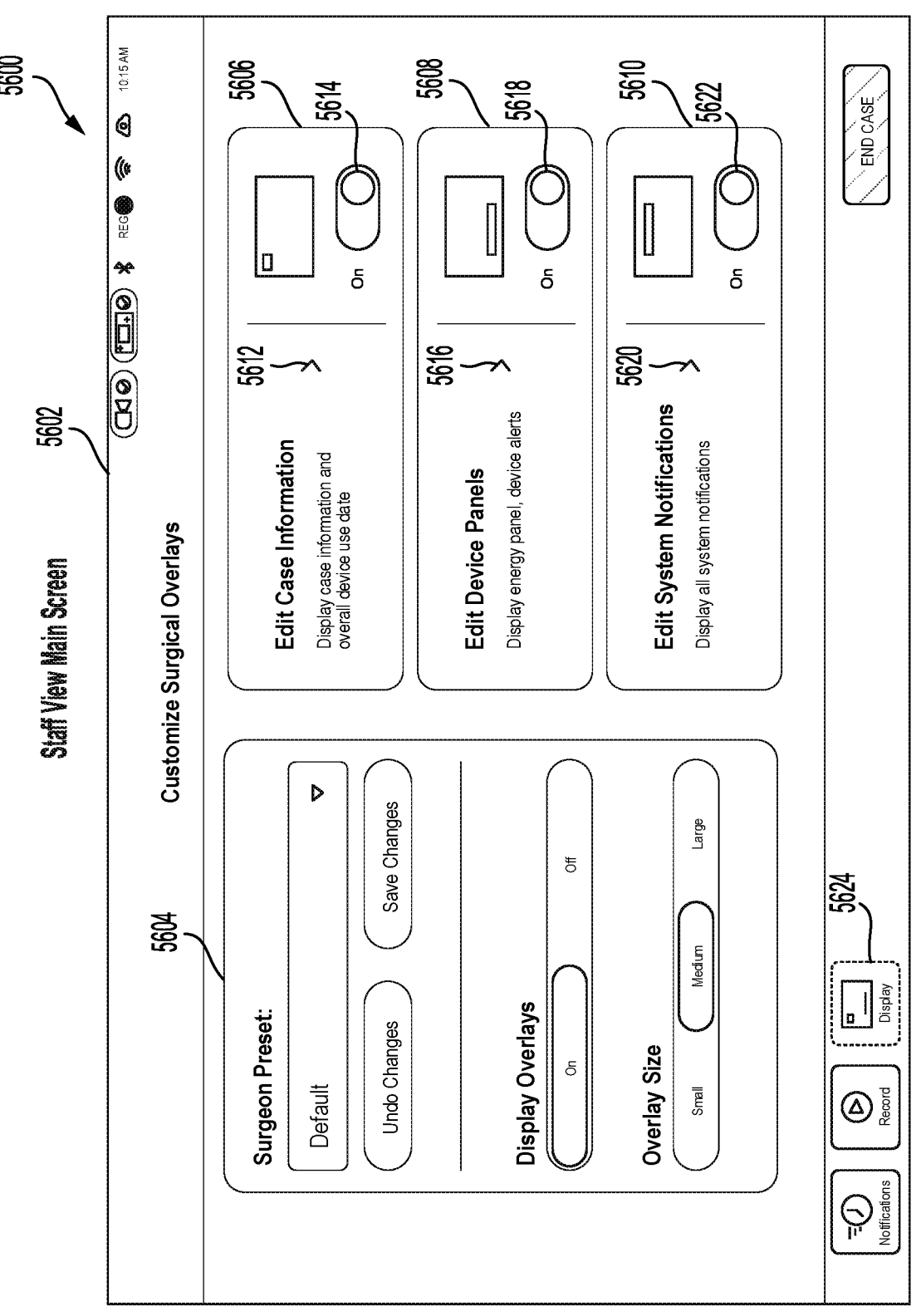
FIG. 72 is an image of a staff view screen displaying customized overlays information, according to one aspect of this disclosure.

FIG. 72 is an image of a staff view screen 5600 displaying customized overlays information. The staff view screen 5600 displays primary surgical display 5602 that enables customization of surgical overlays and includes three main screen portions. A first screen portion 5604 displays a surgeon preset to enable entering surgeon presets or default settings that can be saved, changed, or deleted. The first screen portion 5604 also includes a section that enables display overlays to turned On or Off and an overlay size portion that enables the adjustment of the primary surgical display 5602 from smaller to larger in three settings of Small, Medium, and Large.

A second screen portion 5606 of the primary surgical display 5602 is display to the right of the first screen portion. The second screen portion 5606 displays case information and overall device use date and enables editing the display of the case information. A right chevron 5612 can be tapped to access more granular ability to turn on/off individual overlays. A virtual switch slider button 5612 is used to turn on/off a group of overlays.

A third screen portion 5608 of the primary surgical display 5602 is displayed below the second screen portion 5606. The third screen portion 5608 displays energy panels and device alerts, and enables editing the display of the device panels. Similar to the second screen portion 5606, the third screen portion 5608 includes a right chevron 5616 that can be tapped to access more granular ability to turn on/off individual overlays and a virtual switch slider button 5618 to turn on/off a group of overlays.

A fourth screen portion 5610 of the primary surgical display 5602 is displayed below the third screen portion 5608. The fourth screen portion 5610 displays all system notifications and enables editing of the system notifications. Similar to the second and third screen portions 5606, 5608, the fourth screen portion 5610 includes a right chevron 5620 that can be tapped to access more granular ability to turn on/off individual overlays and a virtual switch slider button 5622 to turn on/off a group of overlays.

Tappable icons are provide at the bottom of the primary surgical display 5602 to provide additional functionality. For example, one tappable icon 5624 enables navigation to staff view screens.

Figure 73:
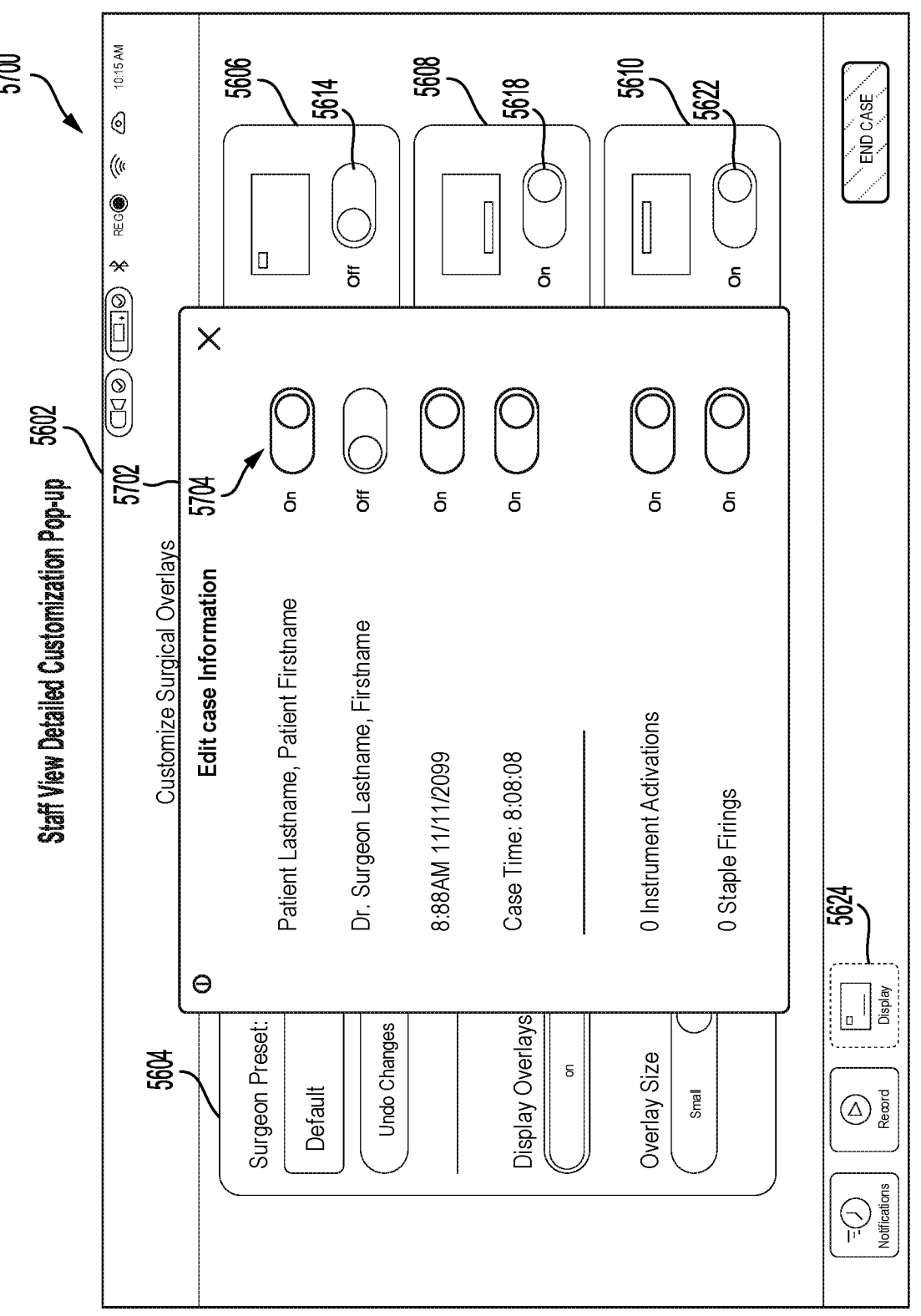
FIG. 73 is an image of a staff view screen displaying detailed customization pop-up information, according to one aspect of this disclosure.

FIG. 73 is an image of a staff view screen 5700 displaying detailed customization pop-up information. The staff view screen 5700 displays an edit case overlay screen 5702 over the primary surgical display 5602 screen. The edit case information overlay screen 5702 allows the ability to turn on/off individual overlay components. The edit case information overlay screen 5702 includes a series of virtual switch slider buttons 5704 to enable editing the patient first and last name, the surgeon first and last name, the time and date of the case (e.g., surgical procedure), the case time, number of instrument activations, or staple firings, for example.

Figure 74:
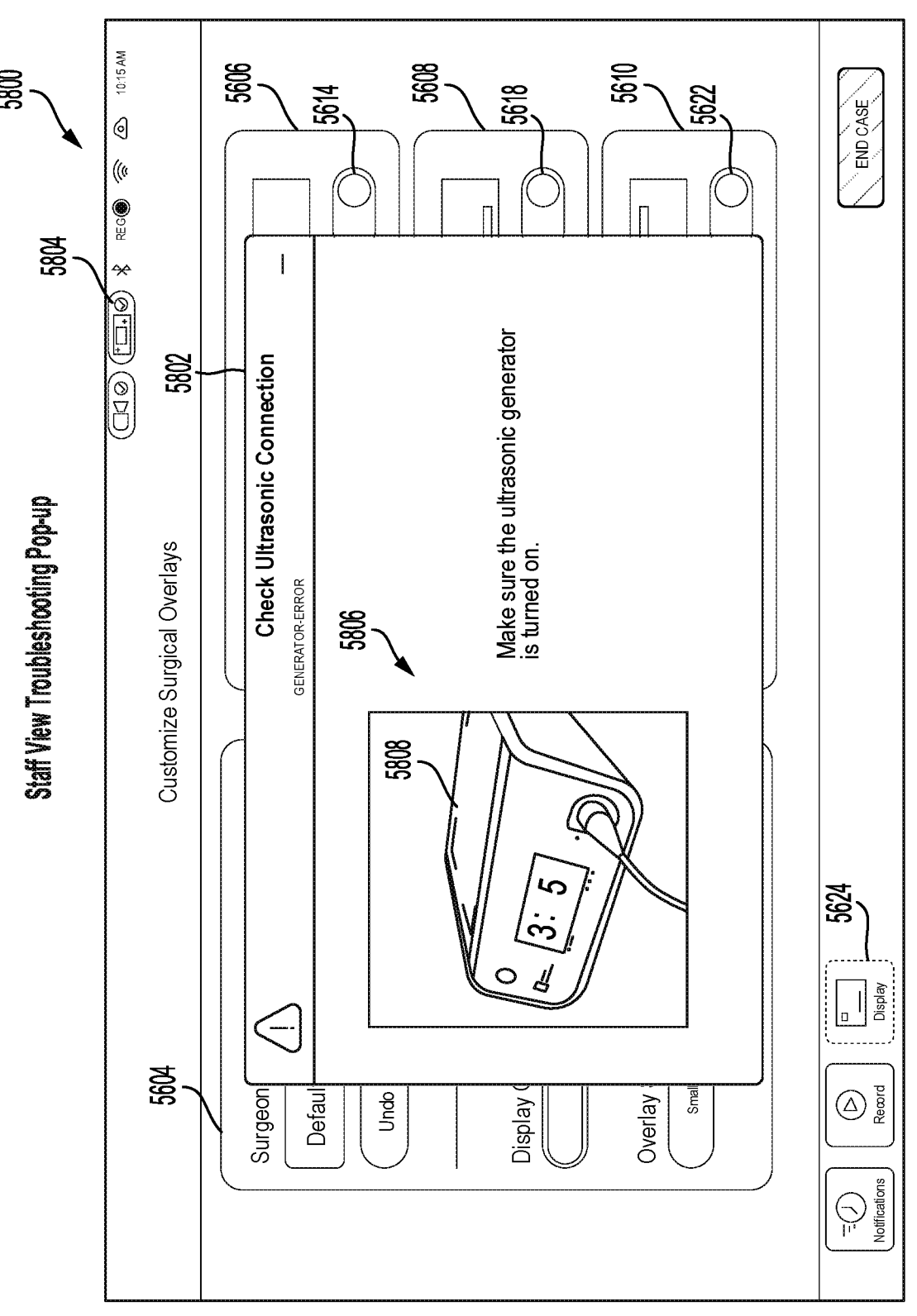
FIG. 74 is an image of a staff view screen displaying staff view troubleshooting pop-up information, according to one aspect of this disclosure.

FIG. 74 is an image of a staff view screen 5800 displaying staff view troubleshooting pop-up information. The staff view screen 5800 displays a staff view troubleshooting pop-up screen 5802 to provide troubleshooting information about system devices and components. A tappable icon 5084 provides device connection status and indicates if the system is properly connected to other capital equipment or devices. The troubleshooting pop-up screen 5802 shows a check ultrasonic connection generator error screen with a static image 5806 of an ultrasonic generator 5808. Additional troubleshooting screens with static images, gifs or animations may be provided. Troubleshooting screens may have multiple steps or multiple screens that a user can advance (not illustrated).

FIG. 75 is an image of a primary surgical display interactions screen 5900 displaying primary surgical display interactions. The primary surgical display interactions screen 5900 shows an instruments panel behavior screen 5902 with an overlay screen 5904 comprising three sections. A first section of the overlay screen 5904 shows device activation information including an instrument activation default panel 5906 and an instrument minimum active panel 5908. Information includes panel background changes from dark to light in activated state and active mode shown in dark text and inactive mode shown in faded opacity, for example.

A second section of the overlay screen 5904 shows instrument disable activation information including an instrument disable activation panel 5910, an alarm status panel 5912, and a disabled instrument panel 5914. When certain alarms are triggered, the instrument panel is grayed out to indicate that activation is disabled. This may apply only when the user is locked out of the device due to alarm status.

A third section of the overlay screen 5904 shows minimize information including a generic instrument default panel 5916 and a minimized panel 5918. The panels are minimized to a predetermined size after a predetermined period. The instrument type remains on the panel and the panel returns to default view when activation or notification occurs.

Situational awareness is the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g., a robotic arm and/or robotic surgical tool) that are connected to it and provide contextualized information or suggestions to the surgeon during the course of the surgical procedure.

Figure 76:
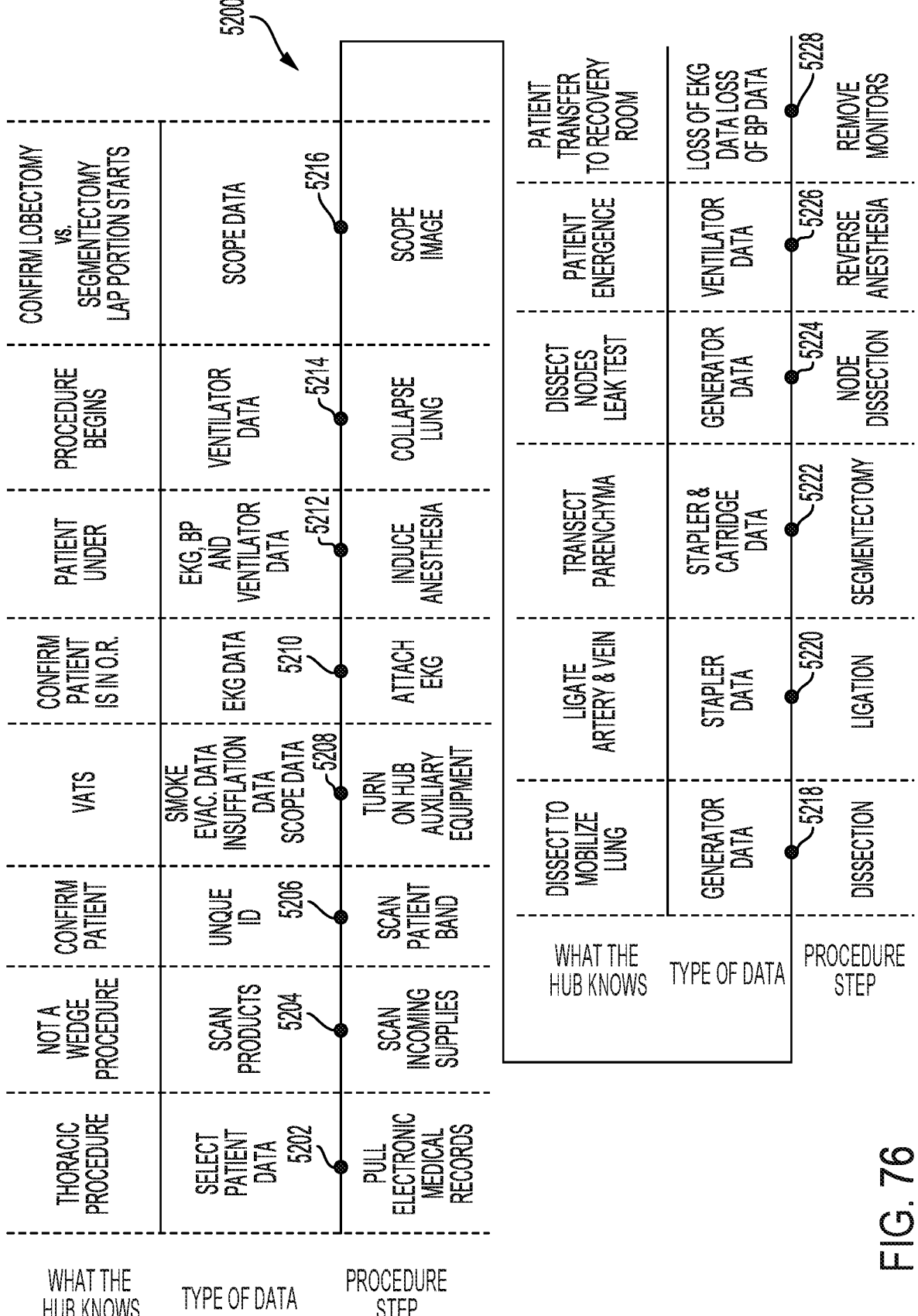
FIG. 76 illustrates a timeline of a situational awareness surgical procedure, according to one aspect of this disclo-sure.

FIG. 76 illustrates a timeline of a situational awareness surgical procedure. FIG. 72 illustrates a timeline 5200 of an illustrative surgical procedure and the contextual information that a surgical hub 5104 can derive from the data received from the data sources 5126 at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 receives data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 is able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described above.

First 5202, the hospital staff members retrieve the patient's EMR from the hospital's EMR database. Based on select patient data in the EMR, the surgical hub 5104 determines that the procedure to be performed is a thoracic procedure.

Second 5204, the staff members scan the incoming medical supplies for the procedure. The surgical hub 5104 cross-references the scanned supplies with a list of supplies that are utilized in various types of procedures and confirms that the mix of supplies corresponds to a thoracic procedure. Further, the surgical hub 5104 is also able to determine that the procedure is not a wedge procedure (because the incoming supplies either lack certain supplies that are necessary for a thoracic wedge procedure or do not otherwise correspond to a thoracic wedge procedure).

Third 5206, the medical personnel scan the patient band via a scanner 5128 that is communicably connected to the surgical hub 5104. The surgical hub 5104 can then confirm the patient's identity based on the scanned data.

Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that is located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 determines that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing.

Fifth 5210, the staff members attach the EKG electrodes and other patient monitoring devices 5124 to the patient. The EKG electrodes and other patient monitoring devices 5124 are able to pair with the surgical hub 5104. As the surgical hub 5104 begins receiving data from the patient monitoring devices 5124, the surgical hub 5104 thus confirms that the patient is in the operating theater.

Sixth 5212, the medical personnel induce anesthesia in the patient. The surgical hub 5104 can infer that the patient is under anesthesia based on data from the modular devices 5102 and/or patient monitoring devices 5124, including EKG data, blood pressure data, ventilator data, or combinations. Upon completion of the sixth step 5212, the pre-operative portion of the lung segmentectomy procedure is completed and the operative portion begins.

Seventh 5214, the patient's lung that is being operated on is collapsed (while ventilation is switched to the contralateral lung). The surgical hub 5104 can infer from the ventilator data that the patient's lung has been collapsed. The surgical hub 5104 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth 5216, the medical imaging device 5108 (e.g., a scope) is inserted and video from the medical imaging device is initiated. The surgical hub 5104 receives the medical imaging device data (i.e., still image data or live streamed video in real time) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized.

For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team begins the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step.

Tenth 5220, the surgical team proceeds to the ligation step of the procedure. The surgical hub 5104 can infer that the surgeon is ligating arteries and veins because it receives data from the surgical stapling and cutting instrument indicating that the instrument is being fired. Similarly to the prior step, the surgical hub 5104 can derive this inference by cross-referencing the receipt of data from the surgical stapling and cutting instrument with the retrieved steps in the process.

Eleventh 5222, the segmentectomy portion of the procedure is performed. The surgical hub 5104 infers that the surgeon is transecting the parenchyma based on data from the surgical instrument, including data from a staple cartridge. The cartridge data may correspond to size or type of staple being fired by the instrument. The cartridge data can indicate the type of tissue being stapled and/or transected for different types of staples utilized in different types of tissues. The type of staple being fired is utilized for parenchyma or other tissue types to allow the surgical hub 5104 to infer that the segmentectomy procedure is being performed.

Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure begins.

Thirteenth 5226, the patient's anesthesia is reversed. The surgical hub 5104 can infer that the patient is emerging from the anesthesia based on the ventilator data (i.e., the patient's breathing rate begins increasing), for example.

Lastly, fourteenth 5228, the medical personnel remove the various patient monitoring devices 5124 from the patient. The surgical hub 5104 can thus infer that the patient is being transferred to a recovery room when the hub loses EKG, BP, and other data from the patient monitoring devices 5124. The surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step 5202 of the timeline 5200 depicted in FIG. 76, the patient data can also be utilized by a situationally aware surgical hub 5104 to generate control adjustments for the paired modular devices 5102.

Various additional aspects of the subject matter described herein are set out in the following numbered examples:

Example 1: An augmented reality display system for use during a surgical procedure, the augmented reality display system comprising: an imaging device to capture a real image of a surgical area during the surgical procedure; an augmented reality display to present a functional data overlay associated with critical operations of a surgical instrument being actively visualized and interactions of the surgical instrument with tissue in the surgical area, wherein the functional data is overlaid onto the real image of the surgical area, and wherein the functional data overlay is a combination of aspects of the critical operations of the surgical instrument and the interaction of the surgical instrument with the tissue in the surgical area; and a processor to:

receive functional data from the surgical instrument; determine the overlaid data related to the functional aspect of the surgical instrument; and combine the aspect of the tissue in the surgical area with the functional data received from the surgical instrument.

Example 2: The augmented reality system of Example 1, further comprising a surgical hub coupled to the augmented reality display, wherein the overlaid data is adjusted by an aspect detected by the surgical hub to modify the overlaid data from information detected by the surgical instrument to add context.

Example 3: The augmented reality system of any one of Examples 1-2, wherein the augmented reality display is modifiable by a user.

Example 4: The augmented reality system of Example 3, wherein the surgical instrument function being monitored is modified based on user modification of the augmented reality display.

Example 5: An augmented reality display system for use during a surgical procedure, the augmented reality display system comprising: an imaging device to capture a real image of a surgical area during the surgical procedure; an augmented reality display to present a functional data overlay associated with parameters of a surgical instrument being actively visualized and interactions of the surgical instrument with tissue in the surgical area, wherein the functional data is overlaid onto the real image of the surgical area, and wherein the functional data overlay is a combination of aspects of the parameters of the surgical instrument and the interaction of the surgical instrument with the tissue in the surgical area; and a processor to: receive functional data from the surgical instrument; determine the overlaid data related to the functional aspect of the surgical instrument; and combine the aspect of the tissue in the surgical area with the functional data received from the surgical instrument.

Example 6: The augmented reality system of Example 5, further comprising a surgical hub coupled to the augmented reality display, wherein the overlaid data is adjusted by an aspect detected by the surgical hub to modify the overlaid data from information detected by the surgical instrument to add context.

Example 7: The augmented reality system of any one of Examples 5-6, wherein the augmented reality display is modifiable by a user.

Example 8: The augmented reality system of Example 7, wherein the surgical instrument function being monitored is modified based on user modification of the augmented reality display.

Example 9: A system, comprising: an augmented reality display system for use during a surgical procedure, the augmented reality display system comprising: an imaging device to capture a real image of a surgical area during the surgical procedure; an augmented reality display to present a functional data overlay associated with a surgical instrument; an energy generator coupled to the surgical instrument, wherein the surgical instrument employs radio frequency (RF) energy and ultrasonic energy during a surgical procedure; a surgical hub coupled to the energy generator and to the augmented reality display, wherein the surgical hub provides a live feed of the surgical area to the augmented reality display to display the live feed of the surgical area; wherein the augmented reality display displays a view of the surgical area, the surgical instrument, and a panel overlay to display information specific to critical operations or parameters of the surgical instrument and interactions of the surgical instrument with tissue if the surgical area.

Example 10: The system of Example 9, wherein the augmented reality display shows an end effector of the surgical instrument grasping tissue and a panel overlay displaying case information, systems notifications, or device panels, or any combination thereof, overlaid over the live feed of the surgical area.

Example 11: The system of Example 10, wherein a location, opacity, size, and placement of the panel overlay is customizable.

Example 12: The system of Example 11, wherein the panel overlay is configured to be turned on or off individually or turned on/off as a group.

Example 13: The system of any one of Examples 10-12, wherein the panel overlay comprises at least one of data input information from capital equipment, generators, insufflator, smoke evacuator, electronic health record, laparoscope, computer, surgical devices, wired and wirelessly connected devices, surgeon profile preferences that may be saved, recalled or edited, or any combination thereof.

Example 14: The system of any one of Examples 10-13, wherein the panel overlay comprises case information including at least one of Patient Name, Surgeon Name, Case Time, or Instrument Activations, or combinations thereof.

Example 15: The system of any one of Examples 10-14, wherein the panel overlay comprises system notifications including at least one of connect instrument status, minor error alert, medium error alert, or major error alert, or any combination thereof.

Example 16: The system of any one of Examples 10-15, wherein the panel overlay comprises information associated with the surgical instrument connected to the system to provide advanced hemostasis.

Example 17: The system of any one of Examples 10-16, wherein the panel overlay comprises a visible patient panel overlay.

Example 18: The system of any one of Examples 10-17, wherein the panel overlay comprises a device panel overlay comprising at least one of device name, device settings, or device supplemental features, or any combination thereof.

Example 19. The system of any one of Examples 10-18, wherein the panel overlay comprises a plurality of panel overlays in a stacked configuration.

Example 20: The system of any one of Examples 10-19, wherein the panel overlay comprises a plurality of panel overlays in an expanded configuration.

Example 21: The system of Example 20, wherein the panel overlay is configured to change dynamically to show state changes such as device activation or power level adjustment.

Example 22: The system of Example 10, wherein the panel overlay depicts optimal device performance (ODP) guide images or other instructions for use (IFU)/informational sources.

Example 23: The system of Example 9, wherein the intraoperative data display comprises a secondary configurable panel.

Example 24: The system of Example 23, wherein the secondary configurable panel changes dynamically based on the selected customized laparoscopic overlay fields displayed in the surgical field of view of a live surgical feed area of the intraoperative data display.

Example 25: The system of Example 24, wherein the customized laparoscopic overlay fields comprise at least one of a bottom edge panel, a top left corner panel, a top center panel, or a side edge panel, or any combination thereof.

Example 26: The system of any one Examples 10-25, wherein the panel overlay displays device troubleshooting information.

Example 27: The system of any one of Examples 10-26, wherein the panel overlay displays at least one of alerts, warnings, device information, or device features, or any combination thereof.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of this disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a control circuit, computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A system, comprising:
an imaging device to capture a real image of a surgical area during the surgical procedure;
an augmented reality display to present a functional data overlay associated with a surgical instrument;
an energy generator coupled to the surgical instrument, wherein the surgical instrument employs radio frequency (RF) energy and ultrasonic energy during a surgical procedure, wherein the surgical instrument is configured to provide hemostasis to tissue of the surgical area;
a surgical hub coupled to the energy generator and to the augmented reality display, wherein the surgical hub is configured to:
provide a live feed of the surgical area to the augmented reality display to display the live feed of the surgical area;
generate overlay information associated with operations of the surgical instrument and interactions of the surgical instrument with tissue of the surgical area;
detect a surgical parameter associated with the surgical procedure; and
adjust the overlay information based on the detected surgical parameter,
wherein the augmented reality display is configured to display a view of the surgical area, the surgical instrument, and a panel overlay to display the adjusted overlay information.

2. The system of claim 1, wherein the augmented reality display shows an end effector of the surgical instrument grasping tissue and a panel overlay displaying case information, systems notifications, or device panels, or any combination thereof, overlaid over the live feed of the surgical area.

3. The system of claim 2, wherein a location, opacity, size, and placement of the panel overlay is customizable.

4. The system of claim 3, wherein the panel overlay is configured to be turned on or off individually or turned on/off as a group.

5. The system of claim 2, wherein the panel overlay comprises at least one of data input information from capital equipment, generators, insufflator, smoke evacuator, electronic health record, laparoscope, computer, surgical devices, wired and wirelessly connected devices, surgeon profile preferences that may be saved, recalled or edited, or any combination thereof.

6. The system of claim 2, wherein the panel overlay comprises case information including at least one of Patient Name, Surgeon Name, Case Time, or Instrument Activations, or combinations thereof.

7. The system of claim 2, wherein the panel overlay comprises system notifications including at least one of connect instrument status, minor error alert, medium error alert, or major error alert, or any combination thereof.

8. The system of claim 2, wherein the panel overlay comprises information associated with the surgical instrument connected to the system to provide advanced hemostasis.

9. The system of claim 2, wherein the panel overlay comprises a visible patient panel overlay.

10. The system of claim 2, wherein the panel overlay comprises a device panel overlay comprising at least one of device name, device settings, or device supplemental features, or any combination thereof.

11. The system of claim 2, wherein the panel overlay comprises a plurality of panel overlays in a stacked configuration.

12. The system of claim 2, wherein the panel overlay comprises a plurality of panel overlays in an expanded configuration.

13. The system of claim 12, wherein the panel overlay is configured to change dynamically to show state changes such as device activation or power level adjustment.

14. The system of claim 2, wherein the panel overlay depicts optimal device performance (ODP) guide images or other instructions for use (IFU)/informational sources.

15. The system of claim 1, wherein the intraoperative data display comprises a secondary configurable panel.

16. The system of claim 15, wherein the secondary configurable panel changes dynamically based on the selected customized laparoscopic overlay fields displayed in the surgical field of view of a live surgical feed area of the intraoperative data display.

17. The system of claim 16, wherein the customized laparoscopic overlay fields comprise at least one of a bottom edge panel, a top left corner panel, a top center panel, or a side edge panel, or any combination thereof.

18. The system of claim 2, wherein the panel overlay displays device troubleshooting information.

19. The system of claim 2, wherein the panel overlay displays at least one of alerts, warnings, device information, or device features, or any combination thereof.

* * * * *